US007915238B2

(12) United States Patent
Hawkins et al.

(10) Patent No.: US 7,915,238 B2
(45) Date of Patent: *Mar. 29, 2011

(54) IMMUNOMODULATORY COMPOUNDS AND METHODS OF USE THEREOF

(75) Inventors: Lynn D. Hawkins, Andover, MA (US); Sally T. Ishizaka, Andover, MA (US)

(73) Assignee: Eisai R & D Management Co., Ltd., Tokyo (JP)

( * ) Notice: Subject to any disclaimer, the term of this patent is extended or adjusted under 35 U.S.C. 154(b) by 408 days.

This patent is subject to a terminal disclaimer.

(21) Appl. No.: 11/411,564

(22) Filed: Apr. 26, 2006

(65) Prior Publication Data

US 2007/0027111 A1 Feb. 1, 2007

Related U.S. Application Data

(63) Continuation-in-part of application No. 11/077,344, filed on Mar. 9, 2005, now Pat. No. 7,833,993, which is a continuation of application No. 10/157,791, filed on May 28, 2002, now abandoned, which is a continuation-in-part of application No. 09/918,849, filed on Jul. 31, 2001, now Pat. No. 6,551,600, which is a continuation-in-part of application No. 09/496,152, filed on Feb. 1, 2000, now Pat. No. 6,290,973.

(60) Provisional application No. 60/118,131, filed on Feb. 1, 1999.

(51) Int. Cl.
*A61K 31/6615* (2006.01)
*A61K 31/683* (2006.01)
*A61K 31/14* (2006.01)

(52) U.S. Cl. ........ 514/103; 514/104; 514/114; 514/119; 514/121; 514/642; 558/159; 558/160

(58) Field of Classification Search .................. None
See application file for complete search history.

(56) References Cited

U.S. PATENT DOCUMENTS

| | | | |
|---|---|---|---|
| 5,484,911 A | | 1/1996 | Hong et al. |
| 5,635,188 A * | | 6/1997 | Bystryn ............ 424/277.1 |
| 5,681,824 A | | 10/1997 | Christ et al. |
| 5,895,653 A | | 4/1999 | Eibl et al. |
| 5,904,925 A | | 5/1999 | Exner |
| 5,961,970 A | | 10/1999 | Lowell et al. |
| 5,985,284 A | | 11/1999 | Lowell |
| 6,136,797 A | | 10/2000 | Zilch et al. |
| 6,146,632 A | | 11/2000 | Momin et al. |
| 6,146,659 A * | | 11/2000 | Rahman ............ 424/450 |
| 6,165,502 A | | 12/2000 | Oleske et al. |
| 6,172,049 B1 | | 1/2001 | Dwyer et al. |
| 6,180,111 B1 | | 1/2001 | Stein et al. |
| 6,284,267 B1 | | 9/2001 | Aneja |
| 6,290,973 B1 * | | 9/2001 | Hawkins et al. ........ 424/278.1 |
| 6,306,404 B1 | | 10/2001 | LaPosta et al. |
| 6,355,257 B1 | | 3/2002 | Johnson et al. |
| 6,437,165 B1 | | 8/2002 | Mandala et al. |
| 6,461,637 B1 | | 10/2002 | Rahman |
| 6,521,776 B2 * | 2/2003 | Hawkins et al. ............ 558/159 |
| 6,551,600 B2 * | 4/2003 | Hawkins et al. ......... 424/278.1 |
| 6,630,161 B1 | 10/2003 | Leesman |
| 6,835,721 B2 * | 12/2004 | Hawkins et al. ............ 514/120 |
| 7,416,726 B2 | 8/2008 | Ravetch |
| 7,560,584 B2 * | 7/2009 | Hawkins et al. ............ 558/166 |
| 7,683,200 B2 | 3/2010 | Fang et al. |
| 2002/0049314 A1 | 4/2002 | Hawkins et al. |
| 2002/0176861 A1 | 11/2002 | Hawkins et al. |
| 2003/0153532 A1 | 8/2003 | Hawkins et al. |
| 2004/0006242 A1 | 1/2004 | Hawkins et al. |
| 2005/0123566 A1 | 6/2005 | Hawkins et al. |
| 2005/0164988 A1 * | 7/2005 | Hawkins et al. .............. 514/78 |
| 2007/0020232 A1 * | 1/2007 | Rossignol et al. ......... 424/85.1 |
| 2007/0027111 A1 | 2/2007 | Hawkins et al. |
| 2007/0292418 A1 * | 12/2007 | Fields et al. ............. 424/133.1 |

FOREIGN PATENT DOCUMENTS

| | | |
|---|---|---|
| EP | 0 390 216 A2 | 3/1990 |
| JP | 02-261866 | 10/1990 |
| WO | WO 93/04672 A1 | 3/1993 |
| WO | WO 95/11700 A1 | 5/1995 |
| WO | WO 98/57659 A1 | 12/1998 |
| WO | WO 00/44758 A1 | 8/2000 |
| WO | WO 00/73263 A1 | 12/2000 |
| WO | WO 01/46127 A1 | 6/2001 |
| WO | WO 01/90129 A2 | 11/2001 |
| WO | WO 02/09752 A2 | 2/2002 |
| WO | WO03/003985 * | 1/2003 |
| WO | WO 03/011223 A2 | 2/2003 |

OTHER PUBLICATIONS

Gokhale et al., "An improved method of encapsulation of doxorubicin in liposomes: pharmacological, toxicological, and therapeutic evaluation" British Journal of Cancer (1996) vol. 74, pp. 43-48.*
The Merck Manual of Diagnosis and Therapy, seventeenth edition, 1999, Published by Merck Research Laboratories, pp. 397-398, 948-949, 1916, and 1979-1981.*
The Oxford Textbook of Oncology, 1995, published by Oxford University Press, pp. 447-453.*
Merriam-Webster's Collegiate Dictionary, Tenth Edition, published 1998 by Merriam-Webster, Incorporated, p. 924.*
Przetak et al., "Novel synthetic LPS receptor agonists boost systemic and mucosal antibody responses in mice" Vaccine (2003) vol. 21 pp. 961-970.*
Braga et al., "Making crystals from crystals: a green route tocrystal engineering and polymorphism" Chemical Communications (2005) pp. 3635-3645.*
Jain et al., "Polymorphism in Pharmacy" Indian Drugs (1986) vol. 23, No. 6, pp. 315-329.*
Vippagunta et al., "Crystalline Solids" Advanced Drug Delivery Reviews (2001) vol. 48 pp. 3-26.*

(Continued)

Primary Examiner — Eric S Olson
(74) Attorney, Agent, or Firm — Myers Bigel Sibley & Sajovec P.A.

(57) ABSTRACT

The present invention is directed to methods of treating diseases and disorders related to immune responses by administering one or more immunomodulatory compounds. In particular, the invention is directed to methods of stimulating and reducing immune responses, therapeutic and prophylactic treatment of cancer, treating autoimmune conditions, treating allergic reactions and asthma, and preventing ischemic damage and asthma by administering one or more immunomodulatory compounds.

11 Claims, 10 Drawing Sheets

OTHER PUBLICATIONS

Pharmaceutical Dosage Forms: Tablets, vol. 2, Published 1990 by Marcel Dekker, Inc., ed. By Lieberman, Lachman, and Schwartz, pp. 462-472.*

Berzoksky and Berkower, "Chapter 8: Immunogenicity and Antigen Structure," *Fundamental Immunology*, William E. Paul, ed., Raven Press NY, p. 242 (1993).

Bhattacharya et al., "Synthesis and Vesicle Formation from Novel Pseudoglyceryl Dimeric Lipids. Evidence of Formation of Widely Different Membrane Organizations with Exceptional Thermotropic Properties," *Chem. Commun.* 23:2287-2288 (1997).

Cespedes et al., "Mouse Models in Oncogenesis and Cancer Therapy," *Clin. Transl. Oncol.* 8(5):318-329 (2006).

Chatterjee et al., "Idiotypic Antibody Immunotherapy of Cancer," *Cancer Immunol. Immunother.* 38:75-82 (1994).

Cheung and Paterson, "American Chemical Society—226th National Meeting: New Drug Highlights," *IDRUGS* 6(10):939-942 (2003).

Defoort et al., "Macromolecular Assemblage in the Design of a Synthetic AIDS Vaccine," *Proc. Natl. Acad. Sci. USA* 89:3879-3883 (1992).

Dennis, "Off by a Whisker," *Cancer News Feature* 442:739-741 (2006).

Dermer, "Another Anniversary for the War on Cancer," *Biotechnology* 12:320 (1994).

Dullenkopf et al., "Synthesis of a Structurally Defined Antigen-Immunostimulant Combination for Use in Cancer Vaccines," *Chem. Euro. J.* 5(8):2432-2438 (1999).

Duralski et al., "Synthesis of Isotopically Labelled Cardiolipins," *Tetrahedron Lett.* 1607-1610 (1998).

Eustache et al., "New Acyclic Analogues of Lipid A: Synthesis of 4-Phosphonoxybutyl and 3-Phosphonoxypropyl Glycosides of 2-Amino-2-Deoxy-D-Glucose," *Carbohydrate Res.* 251:251-267 (1994).

Gregoriadis et al., "Liposomes as Immunological Adjuvants and Vaccine Carriers," *J. Controlled Release* 41(1/02):49-56 (1996).

Gura, "Systems for Identifying New Drugs are Often Faulty," *Science* 278:1041-1042 (1997).

Hawkins et al., "A Novel Class of Endotoxin Receptor Agonists with Simplified Structure, Toll-Like Receptor 4-Dependent Immunostimulatory Action, and Adjuvant Activity," *J. Pharmacol. Exp. Ther.* 300(2):655-661 (2002).

Hawkins et al., "Inhibition of endotoxins response by synthetic TLR4 antagonists," *Curr. Topics Med. Chem.* 4:1147-71 (2004).

Hoffmann et al., "Induction of Tumor Cytotoxicity in Murine Bone Marrow-Derived Macrophages by Two Synthetic Lipopeptide Analogues," *Biol. Chem.* 370:575-582 (1989).

Homma et al., "Structural Requirements of Lipid A Responsible for the Functions: A Study with Chemically Synthesized Lipid A and its Analogues," *J. Biochem.* 98:395-406 (1985).

Inoue and Nojima, "Immunochemical Studies of Phospholipids. I. Reactivity of Various Synthetic Cardiolipin Derivatives with Wassermann Antibody," *Chem. Phys. Lipids* 1(4):360-367 (1967).

Inoue and Nojima, "Immunochemical Studies of Phospholipids. II. Syntheses of Cardiolipin and its Analogues," *Chem. Pharm. Bull.* 16(1):76-81 (1968).

Inoue and Nojima, "Immunochemical Studies of Phospholipids IV: The Reactivities of Antisera Against Natural Cardiolipin and Synthetic Cardiolipin Analogues-Containing Antigens," *Chem. Phys. Lipids (CPLIA4)* 3(1):70-77 (1969).

Jain, "Barriers to Drug Delivery in Solid Tumors," *Scientific American* pp. 58-65 (1994).

Jain et al., "Effect of the Structure of Phospholipid on the Kinetics of Intravesicle Scooting of Phospholipase $A_2$," *Biochim. Biophys. Acta* 860(3):462-474 (1986).

Jiang and Koganty, "Synthetic Vaccines: The Role of Adjuvants in Immune Targeting," *Curr. Med. Chem.* 10:1423-1439 (2003).

Kamitakahara et al., "A Lysoganglioside/poly-L-glutamic Acid Conjugate as a Picomolar Inhibitor of Influenza Hemagglutinin," *Angew. Chem. Int Ed.* 37(11):1524-1528 (1998).

Lien et al., "A Novel Synthetic Acyclic Lipid A-Like Agonist Activates Cells Via the Lipopolysaccharide/Toll-Like Receptor 4 Signaling Pathway," *J. Biol. Chem.* 276(3):1873-1880 (2001).

Matsuura et al., "Activity of Monosaccharide Lipid A Analogues in Human Monocytic Cells as Agonists or Antagonists of Bacterial Lipopolysaccharide," *Infect. Immun.* 67(12):6286-6292 (1999).

Mitchell, "Immunotherapy as Part of Combinations for the Treatment of Cancer," *Int. Immunopharmacol.* 3:1051-1059 (2003).

Przetak et al., "Novel Synthetic LPS Receptor Agonists Boost Systemic and Mucosal Antibody Responses in Mice," *Vaccine* 21:961-970 (2003).

Reichel et al., "Synthetic Carbohydrate-Based Vaccine: Synthesis of an L-Glycero-D-Manno-Heptose Antigen-T-Epitope-Lipopeptide Conjugate," *Chem. Commun.* pp. 2087-2088 (1997).

Roitt et al., "Adjuvants," *Immunology* 8.9 Gower Medical Publishing, London (1985).

Rossignol and Lynn, "TLR4 antagonists for endotoxemia and beyond," *Curr. Opin. Invest. Drugs* 6:295-502 (2005).

Schuster et al., "Cancer Immunotherapy," *Biotechnol. J.* 1:138-147 (2006).

Seaver, "Monoclonal Antibodies in Industry: More Difficult Than Originally Thought," *Genet. Eng. News* 14(14):10 and 21 (1994).

Seydel et al., "The Generalized Endotoxic Principle," *Eur. J. Immunol.* 33:1586-1592 (2003).

The Merck Manual of Diagnosis and Therapy, 17th Edition, 1999, published by Merck Research Laboratories, pp. 1420-1421.

Toyokuni et al., "Synthetic Vaccines: Synthesis of a Dimeric Tn Antigen-Lipopeptide Conjugate that Elicits Immune Responses Against Tn-Expressing Glycoproteins," *J. Am. Chem. Soc.* 116:395-396 (1994).

Vogel, "Immunologic Adjuvants for Modern Vaccine Formulations," *Ann. NY Acad. Sci.* 754:153-160 (1995).

Voskoglou-Nomikos et al., "Clinical Predictive Value of the in Vitro Cell Line, Human Xenograft, and Mouse Allograft Preclinical Cancer Models," *Clin. Cancer Res.* 9:4227-4239 (2003).

Weissig et al., "Functionalized Liposomes with Immunological Adjuvant Effects," *Wiss Z. Martin Luther Univ. Halle-Wittenberg, Math. Naturwiss. Reihe* 39(6):101-109 (1990) (German Language Only).

Wiesmuller et al., "Novel Low-Molecular-Weight Synthetic Vaccine Against Foot-and-Mouth Disease Containing a Potent B-Cell and Macrophage Activator," *Vaccine* 7:29-33 (1989).

Wiesmuller et al., "Solid Phase Peptide Synthesis of Lipopeptide Vaccines Eliciting Epitope-Specific B-, T-Helper and T-Killer Cell Response," *Int. J. Peptide Protein Res.* 40:255-260 (1992).

Wikipedia, online encyclopedia. "Toll-Like Receptor" Definition from Wikipedia.org, (http://en.wikipedia.org/wiki/Toll_Like_Receptor) Accessed Jul. 12, 2006 (5 pages).

U.S. Appl. No. 10/157,791, filed May 28, 2002; Office Action Mailed: Sep. 9, 2004.

U.S. Appl. No. 10/157,791, filed May 28, 2002; Office Action Mailed: Jun. 16, 2005.

U.S. Appl. No. 11/077,344, filed Mar. 9, 2005; Office Action Mailed: Oct. 4, 2007.

U.S. Appl. No. 11/077,344, filed Mar. 9, 2005; Office Action Mailed: Jul. 3, 2008.

U.S. Appl. No. 11/024,328, filed Dec. 28, 2004; Office Action Mailed: Sep. 17, 2007.

U.S. Appl. No. 11/024,328, filed Dec. 28, 2004; Office Action Mailed: Mar. 6, 2008.

U.S. Appl. No. 11/411,332, filed Apr. 26, 2006; Office Action Mailed: Oct. 25, 2007.

U.S. Appl. No. 11/411,332, filed Apr. 26, 2006; Office Action Mailed: Jul. 14, 2008.

U.S. Appl. No. 11/605,557, filed Nov. 28, 2006; Office Action Mailed: Jun. 26, 2008.

Baldridge et al., "Taking a Toll on human disease: Toll-like receptor 4 agonists as vaccine adjuvants and monotherapeutic agents," *Exp. Opin. Biol. Ther.* 4:1129-1138 (2004).

Baselga et al., "Recombinant Humanized Anti-HER2 Antibody (HercaptinTM) Enhances the Antitumor Activity of Paclitaxel and Doxorubicin against HER2/neu Overexpressing Human Breast Cancer Xenografts," *Cancer Res.* 58:2825-2831 (1998).

Belimezi et al., "Growth inhibiton of breast cancer cell lines overexpressing Her2/neu by a novel internalized fully human Fab antibody fragment," Cancer Immunol. Immunother. 55:1091-1099 (2006).

Clynes et al., "Inhibitory Fc receptors modulate in vivo cytoxicity against tumor targets," Nature Med. 6:443-446 (2000).

Coelho et al., "Isolation and characterisation of a human anti-idiotypic scFv used as a surrogate tumour antigen to elicit an anti-HER-2/neu humoral response in mice," British J. Cancer 90:2032-2041 (2004).

Cooper et al., "CPG 7909, an Immunostimulatory TLR9 Agonist Oligodeoxynucleotide, as Adjuvant to Engerix-B® HBV Vaccine in Healthy Adults: A Double-Blind Phase I/II Study," J. Clin. Immunol. 24:693-701 (2004).

Cragg et al., "Antibody specificity controls in vivo effector mechanisms of anti-CD20 reagents," Blood 103:2738-2743 (2004).

Dalpke et al., "CpG DNA in the Prevention and Treatment of Infections," Biodrugs 16:419-431 (2002).

EISAI Research Inst. Product Datasheet for E6020 or ER-804057 (pp. 1-5; Mar. 1999).

Overholser et al., "Epidermal Growth Factor Receptor Blockade by Antibody IMC-C225 Inhibits Growth of a Human Pancreatic Carcinoma Xenograft in Nude Mice," Cancer 89:74-82 (2000).

Ross et al., "The HER-2/neu Gene and Protein in Breast Cancer 2003: Biomarker and Target of Therapy," Oncologist 8:307-325 (2003).

Skinner et al., "Imiquimod" Dermatol. Clin. 21:291-300 (2003).

Zhang et al., "FCGR2A and FCGR3A Polymorphisms Associated With Clinical Outcome of Epidermal Growth Factor Receptor-Expressing Metatastic Colorectal Cancer Patients Treated With Single-Agent Cetuximab," J. Clin. Oncol. 25:3712-3718 (2007).

U.S. Appl. No. 11/411,332, filed Apr. 26, 2006; Office Action Mailed: Mar. 10, 2009.

U.S. Appl. No. 11/605,557, filed Nov. 28, 2006; Office Action Mailed: Feb. 26, 2009.

U.S. Appl. No. 11/077,344, filed Mar. 9, 2005; Office Action Mailed: Jun. 30, 2009.

U.S. Appl. No. 11/077,344, filed Mar. 9, 2005; Office Action Mailed: Jun. 30, 2009.

U.S. Appl. No. 11/411,332, filed Apr. 26, 2006; Office Action Mailed: Sep. 24, 2009.

U.S. Appl. No. 11/605,557, filed Nov. 28, 2006; Office Action Mailed: Sep. 4, 2009.

U.S. Appl. No. 11/077,344, filed Mar. 9, 2005; Office Action Mailed: Jan. 14, 2010.

Beckman et al., "Antibody Constructs in Cancer Therapy: Protein Engineering Strategies to Improve Exposure in Solid Tumors," Cancer 109:170-179 (2007).

Berenbaum, "Synergy, additivism and antagonism in immunosuppression," Clin. Exp. lmmunol. 28:1-18 (1977).

Berenbaum, "What is Synergy?," Pharmacol. Rev. 41:93-141 (1989).

Fujimori et al., "A Modeling Analysis of Monoclonal Antibody Percolation Through Tumors: A Binding-Site Barrier," J. Nuc. Med. 31:1191-1198 (1990).

Lederman et al., "A Single Amino Acid Substitution in a Common African Allele of the CD4 Molecule Ablates Binding of the Monoclonal Antibody, OKT4," Mol. Immunol. 28:1171-1181 (1991).

Li et al., "β-Endorphin omission analogs: Dissociation of immunoreactivity from other biological activities," Proc. Natl. Acad. Sci. USA 77:3211-3214 (1980).

Rudnik et al., "Affinity and Avidity in Antibody-Based Tumor Targeting," Can. Biotherp. Radiopharm. 24:155-162 (2009).

Tallarida, "Drug Synergism and Dose-Effect Data Analysis," Ed. Chapman & Hall, pp. 1-8, 10-13 and 57-71 (2000).

Talmadge et al., "Murine Models to Evaluate Novel and Conventional Therapeutic Strategies for Cancer," Am. J. Pathol. 170:793-804 (2007).

Thurber et al., "Antibody tumor penetration: Transport opposed by systemic and antigen-mediated clearance," Adv. Drug Deliv. Rev. 60:1421-1434 (2008).

U.S. Appl. No. 11/411,332, filed Apr. 26, 2006; Office Action Mailed: Jan. 22, 2010.

U.S. Appl. No. 11/605,557, filed Nov. 28, 2006; Office Action Mailed: Jan. 22, 2010.

U.S. Appl. No. 11/411,332, filed Apr. 26, 2006; Office Action Mailed: Jul. 26, 2010.

* cited by examiner

Intraperitoneal (i.p.)TLR agonists enhance therapeutic efficacy of B16-GM-CSF vaccine Local TLR agonists enhance therapeutic efficacy of B16-GM-CSF vaccine

IMMUNOMODULATORY COMPOUNDS AND METHODS OF USE THEREOF

This application is a continuation-in-part application of U.S. Ser. No. 11/077,344, filed Mar. 9, 2005, which is a continuation of U.S. Ser. No. 10/157,791 filed May 28, 2002, which is a continuation in part of the U.S. Ser. No. 09/918,849, filed Jul. 31, 2001, now issued as U.S. Pat. No. 6,551,600, which is a continuation-in-part of U.S. Ser. No. 09/496,152, filed Feb. 1, 2000, now issued as U.S. Pat. No. 6,290,973, which is a non-provisional application of U.S. provisional Ser. No. 60/118,131, filed Feb. 1, 1999.

BACKGROUND OF THE INVENTION

The immune system provides vital defenses against invading pathogens, such as bacteria, viruses, parasites, helminthes, and other foreign invaders, as well as providing protection against the proliferation of neoplastic cells. The elimination of pathogens and neoplastic cells requires stimulation of the immune system. However, in certain cases immune responses and immune stimulation can also cause or contribute to diseases and pathologies such as autoimmune disease, inflammation, allergy, anaphylaxis, and septic shock.

The generation of effective treatments for these diseases and pathologies has proved elusive. For example, broad spectrum immunosuppressants such as cyclosporine A and steroids can be used to treat autoimmune diseases, allergies, and other pathologies, but these treatments can present severe side effects. Similarly, current treatments for inflammatory conditions such as chronic adrenocortical disorder and hyperfunction, allergies, rheumatoid arthritis, lupus, inflammatory bowel disease, pneumonia, bronchial asthma, hematological disorders, dermatitis and eczema can present undesired side effects of these agents including hypertension, atherosclerosis, diabetes, hyperglycemia, bone thinning and electrolyte imbalance.

Improved treatments for diseases and pathologies associated with the immune system and immune responses requires the ability to modulate and redirect certain immune responses so as to suppress harmful responses without compromising an individual's ability to eliminate infections.

SUMMARY OF THE INVENTION

In one aspect, the present invention provides a method for inducing or stimulating an immune response by administering an effective amount of a compound of the formulae (I), (II), (III), (IV), and (V).

In another aspect, the invention provides a method for upregulating an immune response by administering an effective amount of a compound of the formulae (I), (II), (III), (IV), and (V).

In another aspect, the invention provides a method for reducing an immune response in a subject, the method comprising administering to the subject a compound of the formulae (I), (II), (III), (IV), and (V).

In another aspect, the invention provides a method for desensitizing a subject against the occurrence of an allergic reaction in response to contact with a particular allergen or antigen, comprising administering to the subject an effective amount of a compound of the formulae (I), (II), (III), (IV), and (V).

In another aspect, the invention provides a method for treating a subject having an autoimmune disease, comprising administering to the subject an effective amount of a compound of the formulae (I), (II), (III), (IV), and (V).

In another aspect, the invention provides a method for treating a subject having an inflammatory condition, comprising administering to the subject an effective amount of a compound of the formulae (I), (II), (III), (IV), and (V).

In another aspect, the invention provides a method for preventing or reducing ischemic damage in a subject requiring surgery, comprising administering to the subject an effective amount of a compound of the formulae (I), (II), (III), (IV), and (V).

In another aspect, the invention provides a method for preventing, ameliorating, or delaying the onset of asthma in a subject, comprising administering to the subject an effective amount of a compound of the formulae (I), (II), (III), (IV), and (V).

In another aspect, the invention provides an immunostimulatory remedy containing as the active ingredient a compound of the formulae (I), (II), (III), (IV), and (V).

DETAILED DESCRIPTION OF THE PREFERRED EMBODIMENTS

Figure 1:
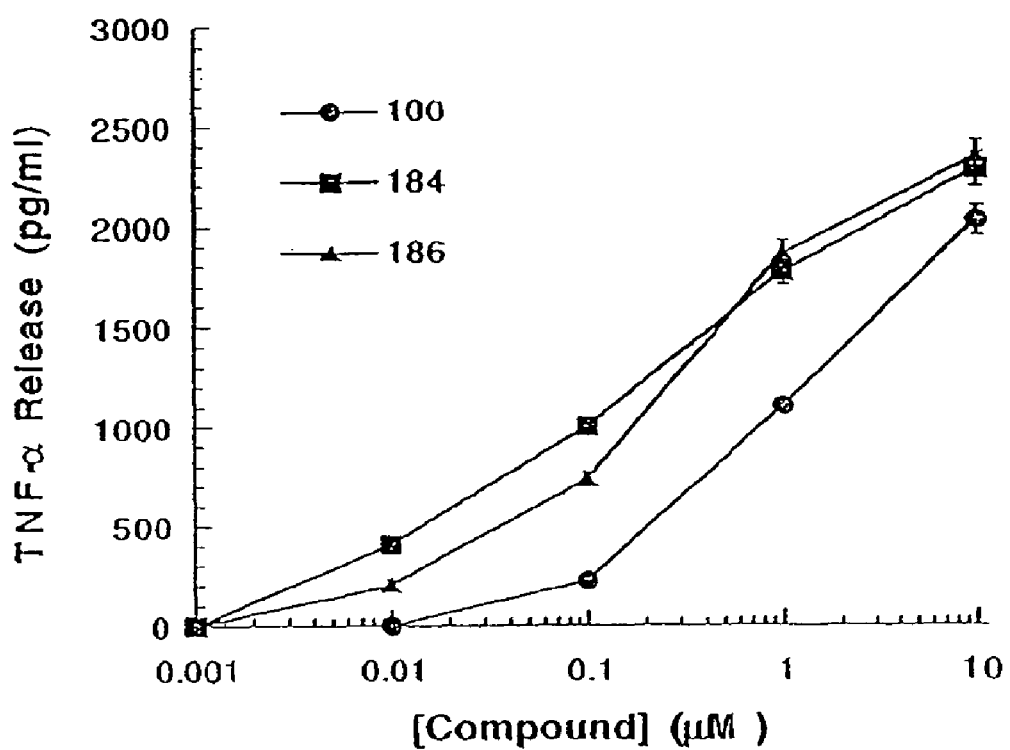
FIG. 1 is a graph that shows the results of an in vitro assay for induction of TNF-alpha cytokine release by compounds 100, 184 or 186 of the invention.

The present invention is directed to methods of using immunomodulatory compounds of the formulae (I), (II), (III) (IV), and (V) and/or a pharmaceutically acceptable salt, hydrate, solvate, stereoisomer, amorphous solid thereof, or any combination thereof. The compounds of Formula (I), (II), (III), (IV) and (V) can function as adjuvants and/or as immunostimulatory compounds depending on the application in which they are used.

Methods of Modulating Immune Responses

The present invention is directed to methods of modulating immune responses by administering immunomodulatory compounds that elicit cytokines and activate immune cells. In particular, the present invention is directed to methods of using immunomodulatory compounds to stimulate immune responses directed against pathogens or neoplastic cells, or to suppress immune responses associated with inflammation, allergy, and anaphylaxis.

As used herein "immunomodulatory compounds" describes compounds which, when administered to a subject, stimulate the production of cytokines and elicit particular responses by immune cells. The stimulation of cytokines is known to enhance the activity of some immune cells and to suppress the activity of other immune cells.

The immunomodulatory compounds used in the methods of the invention are ligands for the TLR4 receptor. TLR4 is a member of the Toll-like receptor (TLR) family of receptors. In humans, the TLR family comprises ten known receptors, designated TLR1-10. TLR receptors are associated with innate immune recognition of pathogens, and known TLR ligands are associated with pathogens or tissue damage. For example, other known TLR4 ligands include bacterial endotoxin (also known as lipopolysaccharide, or LPS), parasite lipoproteins, human heat shock protein 70, and human necrotic cell debris. Ligands to other known TLRs are also associated with pathogens and tissue damage, and include peptidoglycan, which is recognized by TLR2, flagellin, which is recognized by TLR5, and unmethylated bacterial CpG DNA sequences, which are recognized by TLR9.

Recognition of ligand by TLR4 results in the secretion of cytokines and activation of various pathways and behaviors in immune cells. TLR4 ligands typically elicit a set of cytokines that includes IL-$\beta$, IL-6, IL-10, IL-12, and TNF$\alpha$. Many of the cytokines elicited by TLR4 ligands have known immunomodulatory or immunoprotective effects. At least two of these cytokines, IL-10 and IL-12, play a role in regulating inflammatory responses. For example, IL-10 has anti-inflammatory properties, and is associated with T cell populations that down-regulate inflammatory reactions. IL-10 may also be involved in down-regulating responses mediated by the Th1 subset of T helper cells, which are associated with many forms of inflammatory disease such as rheumatoid arthritis and Crohn's disease. Thus, TLR4 ligands can be useful for modulating responses mediated by Th1 cells. As another example, IL-12 is associated with Th1 related functions involved in suppressing certain aspects of allergic disease, including B cell synthesis of IgE, which are mediated through the Th2 subset of T helper cells. Thus, TLR4 agonists and related compounds may be useful for down-regulating Th2 responses and resolving conditions dependent on IL-4 or other Th2 associated cytokines.

As described in more detail in the Examples provided below, the immunomodulatory compounds used in the methods of the invention can elicit production of cytokines, including IL-1$\alpha$, IL-1$\beta$, IL-6, IL-10, IL12, interferon-$\alpha$, interferon-$\gamma$, and GM-CSF.

Thus, in one aspect, the invention provides a method of inducing or stimulating an immune response in a subject individual by administering a compound of the formulae (I), (II), (III), (IV), and (V). As used herein, inducing or stimulating an immune response means stimulating the production of cytokines, stimulating the proliferation of immune cells, stimulating the activation of immune cells, or stimulating the lytic activity of immune cells. Examples of immune responses stimulated by the methods of the invention are the secretion of cytokines, the activation of NK cells, the proliferation of B cells, T cells, macrophages, monocytes, and other immune cells, and other immune responses. These responses may in turn enhance or down-regulate other immune functions.

The methods of the invention can be used to stimulate immune responses to treat a variety of infections, including, but not limited to, gram-positive and gram-negative bacterial infections, viral infections, fungal infections, and parasitic infections. Infection from certain viruses are known to lead to the development of different types of cancers, for example, human papilloma virus (HPV), hepatitis viral infections, Epstein-Barr virus (EBV), human herpes virus 8 (HHV-8), human T-cell leukemia virus-1 (HTLV-1) and human T-cell leukemia virus-2 (HTLV-2). The methods of the invention can be used to treat these viruses associated with cancer.

The methods of the invention can also be used to treat neoplastic conditions, including, but not limited to biliary tract cancers, brain cancer, breast cancer, cervical cancer, choriocarcinoma, colon cancer, endometrial cancer, esophageal cancer, gastric cancer, intraepithelial neoplasms, lymphomas, liver cancer, lung cancer, melanoma, neuroblastomas, oral cancer, ovarian cancer, pancreatic cancer, prostate cancer, rectal cancer, sarcomas, skin cancer, testicular cancer, thyroid cancer, renal cancer, and other carcinomas and sarcomas.

The compounds may be used therapeutically, that is, the compounds are administered to treat an existing cancer, or to prevent the recurrence of a cancer, or prophylactic, that is, the compounds are administered to prevent or delay the development of cancer. When the compounds are used therapeutically, they are administered to cancer patients and are designed to elicit an immune response to stabilize a tumor by preventing or slowing the growth of the existing cancer, to prevent the spread of a tumor or of metastases, to reduce the tumor size, to prevent the recurrence of treated cancer, or to eliminate cancer cells not killed by earlier treatments. A compound used as a prophylactic treatment is administered to individuals who do not have cancer, and are designed to elicit an immune response to target potential cancer cells or to target an antigen derived from a virus associated with cancer.

The methods of the invention can be used to treat a subject invidual at risk for developing cancer, diagnosed with a cancer, in treatment for cancer, or in post-therapy recovery from cancer or the compounds of the invention can be administered as a prophylactic to a subject individual to prevent or delay the development of cancer.

As used herein, the term "stimulate an immune response" includes stimulating, eliciting, increasing, enhancing, sustaining, and/or improving the stimulation of new immune response or of a preexisting immune response. Thus, "stimulating an immune response" as an immunotherapy refers to enhancing the therapeutic efficacy, increasing survival time, slowing the progression of a cancerous tumor or shrinking the cancerous tumor size, preventing the spread of a tumor or of metastases, preventing or slowing the recurrence of treated cancer, eliminating cancer cells not killed by earlier treatments, targeting potential cancer cells or targeting antigens derived from a virus associated with cancer. In the methods of this invention, one or more compounds selected from formulae (I), (II), (III), (IV) and (V) are administered in an amount effective to stimulate an immune response in the subject individual at a dose sufficient to generate an effective immune response without unacceptable toxicity. As will be understood by one of skill in the art, the magnitude of the immune response and the maintenance of that response may have varying degrees which will be recognized a having a potential therapeutic or prophylactic benefit.

In some instance, these treatments can be used in combination with conventional cancer therapies or pharmaceutical formulations useful for treating cancer or infectious diseases. These treatments can include surgical procedures, radiation therapy and/or ablation therapy (e.g., laser therapy, infrared therapy and the like).

Cancer therapies including dendritic cell therapy, chemokines, cytokines, tumor necrosis factors (e.g., TNF-α), chemotherapeutic agents (e.g., adenosine analogs (e.g., cladribine, pentostatin), alkyl sulfanates (e.g., busulfan)), anti-tumoral antibiotics (e.g., bleomycin, dactinomycin, daunorubicin, doxorubicin, epirubicin, idarubicin, mitoxantrone, mitomycin), aziridines (e.g., thiotepa), camptothecin analogs (e.g., irinotecan, topotecan), cryptophycins (e.g., cryptophycin 52, cryptophicin 1), dolastatins (e.g., dolastatin 10, dolastatin 15), enedyine anticancer drugs (e.g., esperamicin, calicheamicin, dynemicin, neocarzinostatin, neocarzinostatin chromophore, kedarcidin, kedarcidin chromophore, C-1027 chromophore, and the like), epipodophyllotoxins (e.g., etoposide, teniposide), folate analogs (e.g., methotrexate), maytansinoids (e.g., maytansinol and maytansinol analogues), microtubule agents (e.g., docetaxel, paclitaxel, vinblastine, vincristine, vinorelbine), nitrogen mustards (e.g., chlorambucil, cyclophosphamide, estramustine, ifosfamide, mechlorethamine, melphalan), nitrosoureas (e.g., carmustine, lamustine, streptoxacin), nonclassic alkylators (e.g., altretamine, dacarbazine, procarbazine, temozolamide), platinum complexes (e.g., carboplatin, cisplatin), purine analogs (e.g., fludarabine, mercaptopurine, thioguanine), pyrimidine analogs (e.g., capecitabine, cytarabine, depocyt, floxuridine, fluorouracil, gemcitabine), substituted ureas (e.g., hydroxyurea)]; anti-angiogenic agents (e.g., canstatin, troponin I), biologic agents (e.g., ZD 1839, virulizin and interferon), antibodies and fragments thereof (e.g., anti EGFR, anti-HER-2/neu, anti-KDR, IMC-C225), anti-emetics (e.g., lorazepam, metroclopramide, and domperidone), epithelial growth factor inhibitors (e.g., transforming growth factor beta 1), anti-mucositic agents (e.g., dyclonine, lignocaine, azelastine, glutamine, corticoid steroids and allopurinol), anti-osteoclastic agents (e.g., bisphosphonates {e.g., etidronate, pamidronate, ibandronate, and osteoprotegerin}), hormone regulating agents (e.g., anti-androgens, LHRH agonists, anastrozole, tamoxifen), hematopoietic growth factors, anti-toxicity agents (e.g., amifostine) and mixtures of two or more thereof.

Antibodies that block immunosuppressive functions, for example, anti-CTLA4 antibodies that block a receptor on T cells that turns off activation may also be used in combination with a compound of formulae (I), (II), (III), (IV) and (V). Thus, administering one or more compounds of formulae (I), (II), (III), (IV) and (V) with anti-CTLA4 antibodies will increase immune response in the subject individual.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype" or "drug response genotype"). Thus, another aspect of the invention provides methods for tailoring an individual's prophylactic or therapeutic treatment according to that individual's drug response genotype. Pharmacogenomics allows a clinician or physician to target prophylactic or therapeutic treatments to patients who will most benefit from the treatment and to avoid treatment of patients who will experience toxic drug-related side effects. The clinician or physician can thereby tailor the type of treatment that may be necessary to the specific patient.

In one embodiment of the methods of immunotherapy, the immune response is further augmented by the administration of compounds that may act as an immunostimulatory compound. Exemplary immunostimulatory compounds include toll like receptor (TLR) agonists (e.g., TLR4, TLR7, TLR9), N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, pegylated G-CSF, SCF, IL-3, IL6, PIXY 321), interferons (e.g., γ-interferon, α-interferon), interleukins (e.g., IL-2, IL-7, IL-12, IL-15, IL-18), MHC Class II binding peptides, saponins (e.g., QS21), unmethylated CpG sequences, 1-methyl tryptophan, arginase inhibitors, cyclophosphamide, antibodies that block immunosuppressive functions (e.g., anti-CTLA4 antibodies), and mixtures of two or more thereof. Exemplary TLR4 agonists include lipopolysaccharides (LPS); *E. coli* LPS; and *P. gingivalis* LPS. Exemplary TLR7 agonists include imidazoquinoline compounds (e.g., imiquimod, resiquimod and the like); and loxoribine.

In another aspect, the invention provides a method for upregulating an immune response in a subject by administering an immunomodulatory compound of the formulae (I), (II), (III), (IV), and (V). As used herein, upregulating an immune response means to increase an existing immune response or a component of an existing immune response. Methods for upregulating immune responses can be used to treat any of the infections or neoplastic disorders described above herein. Methods for upregulating immune responses can also be used to treat autoimmune, inflammatory, or allergic disorders by altering the balance of Th1 and Th2 responses. For example, administration of the immunomodulatory compounds of the invention can be used to alter the balance of Th1 and Th2 responses, thereby reducing a subject's immune response to animal danders, pollen, dust mites, hymenoptera venoms, and other antigens or allergens. Administration of the immunomodulatory compounds of the invention can also be used to treat conditions such as asthma, atopic dermatitis, allergic rhinitis, eczema, urticaria, and food allergies.

In another aspect, the invention provides a method for reducing an immune response in a subject by administering an immunomodulatory compound of the formulae (I), (II), (III), (IV), and (V). As used herein, reducing an immune response in a subject means to cause a decrease in the production of cytokines, the proliferation of lymphocytes, monocytes, macrophages, dendritic cells, or natural killer cells, to cause a decrease in the lytic activity of natural killer cells, or to cause a decrease in the lytic activity of cytotoxic T cells.

In another aspect, the invention provides a method of desensitizing a subject against the occurrence of an allergic reaction in response to contact with a particular antigen or allergen, comprising administering an immunostimulatory compound of formulae (I), (II), (III), (IV), and (V) as the active ingredient. As used herein, desensitizing a subject means to reduce the immune response of the subject to exposure to particular allergens or antigens. For example, the subject may display decreased production of IgE, decreased production of IgE producing B cells, decreased production of histamine, or decreased release of cytokines in response to exposure to an allergen or antigen.

In another aspect, the invention provides a method of preventing, ameliorating, or delaying the onset of asthma in a subject by administering a compound of formulae (I), (II), (E), (IV), and (V) to the subject.

Recent studies have indicated that exposure to microbial agents during childhood can confer a protective benefits, such as providing protection against development of asthma and other allergic conditions. It has been suggested that providing safe and effective antigens that mimic the protective effects of microbial pathogens without the associated risks could confer similar protection against development of allergy and asthma (Liu, A. H. (2002) *J. Allergy Clin Immunol.* 109:379-92).

In the methods of the invention, at least one of the immunostimulatory compounds according to the formulae (I), (II), (III), (IV), and (V) is administered to a subject at risk of developing allergies or asthma. Preferably, the subject is a juvenile subject.

The TLR ligand endotoxin is associated with a phenomenon known as endotoxin tolerance. Endotoxin (also known as lipopolysaccharide, or LPS) is a glycolipid found in the cell membranes of Gram-negative bacteria. Endotoxin is one of the most potent known stimulators of immune responses, and exposure to endotoxin induces cytokine production by monocytes and macrophages. Endotoxin tolerance refers to the observation that an initial low or sublethal dose of endotoxin results in a decreased immune response to a later, high dose of endotoxin, and can protect against lethal subsequent doses of endotoxin. The decreased immune response is manifested in the down-regulation of macrophage responsiveness, and decreased levels of cytokine release compared to individuals who were not pretreated, or tolerized, with low doses of endotoxin.

Similarly, administration of the immunomodulatory compounds described herein can suppress subsequent responses to TLR4 ligands such as endotoxin. Moreover, administration of the immunomodulatory compounds described herein can also down regulate responses mediated by subsequent exposure to other TLR ligands, including TLR2 ligands, such as lipoprotein, and TLR9 ligands, such as unmethylated CpG nucleic acids, as described in more detail in Example 1.

Administration of the immunomodulatory compounds of the invention can be used to suppress the ability of TLR ligands such as bacterial DNA, viral RNA, endogenous human heat shock proteins, parasitic or bacterial lipids, glycolipids or lipoproteins to stimulate immune responses.

TLR ligands such as endotoxin are shown to elicit or exacerbate a number of immune-based diseases. For example, intestinally derived endotoxin is released during graft-versus-host disease after bone marrow grafting, and increases the severity of post-graft symptoms. Endotoxin is the active principle in eliciting lung responses to environmental or occupational irritants such as grain dust, cotton dust, or poultry processing dusts. Environmental endotoxin is found to enhance bronchial responses in pre-existing asthma. A TLR9 ligand is found to enhance proliferation of B cells associated with secretion of autoantibodies in systemic lupus erythematosus. Tolerization of TLRs may prevent TLR ligands from exacerbating or causing diseases or syndromes such as systemic lupus erythematosus, asthma, atherosclerosis, graft-versus-host disease, grain dust fever, inflammatory bowel disease, rheumatoid arthritis, mucositis, and others.

In another aspect, the invention provides a method of preventing or reducing ischemic damage in a subject requiring surgery by administering a compound of formulae (I), (II), (III), (IV), and (V) prior to performing surgery on the subject.

Ischemia and reperfusion result in tissue injury in a number of organs, including heart, brain, kidney, and gastrointestinal tract. Ischemia/reperfusion injury is associated with a number of surgical procedures, including transplantation of organs such as kidney, liver and heart, procedures that require periods of hyperperfusion, and revascularization procedures.

The administration of the TLR4 ligand endotoxin has been shown to induce cross-tolerance to insults other than endotoxemia. Pretreatment of subjects with endotoxin has been shown to provide protection against ischemia-reperfusion injury in the myocardium, liver, and kidney (Meldrum, et al. (1996) *Arch. Surg.* 131:1203-1208, Colletti, et al. (1994) *J. Surg. Res.* 57:337-343, and Heemann et al. (2000) *Am. J. Path.* 156:287-293).

In the methods of the invention, at least one of the immunostimulatory compounds according to the formulae (I), (II), (III), (IV), and (V), is administered to a subject prior to surgery. The compound or compounds can be administered from several hours up to three days prior to surgery.

In another aspect, the invention provides a method of treating autoimmune condition by administering an immunostimulatory compound of formulae (I), (II), (III), (IV), and (V).

Innate immunity has been implicated in the development and progression of autoimmune conditions including type I diabetes mellitus, systemic lupus erythamatosus, and others. The modulation of autoimmune responses is mediated by toll-like receptor-ligand interactions, and recent evidence indicates that TLR ligands can be used to modulate autoimmune responses. A TLR-9 mediated mechanism enhances proliferation of B cells associated with secretion of autoantibodies in systemic lupus erythematosus. B cells activated by endotoxin have been shown to prevent the onset of autoimmune diabetes in nonobese diabetic mice (Tian, J., et al. (2001) *J. Immunol.* 167: 1081-9). Thus, modulation of immune responses by TLR ligands can provide treatments for autoimmune conditions.

In the methods of the invention, at least one immunomodulatory compound defined by the general formulae (I), (I), (III), (IV), and (V) is administered to a subject suffering from an autoimmune disorder or other disorder having an autoimmune component. Administration of an immunomodulatory compound can modulate the release of cytokines and suppress T-cell subsets involved in autoimmune disease. Many autoimmune disorders are associated with Th1 cytokine patterns. Redirection of T help to Th2 may treat these diseases. Alternatively, tolerization of TLRs using these immunostimulatory compounds may suppress aspects of the disease that are mediated by TLR stimulation.

Diseases and conditions that can be treated by the methods of the invention include, but are not limited to, systemic lupus erythematosis, sceleroderma, Sjbgren's syndrome, multiple sclerosis and other demyelinating diseases, rheumatoid arthritis, juvenile arthritis, myocarditis, Graves' disease, uveitis, Reiter's syndrome, gout, osteoarthritis, polymyositis, primary biliary cirrhosis, Crohn's disease, ulcerative colitis, aplastic anemia, Addison's disease, insulin-dependent diabetes mellitus, and other diseases.

In another aspect, the invention provides a method of treating an inflammatory condition by administering an immunomodulatory compound of formulae (I), (II), (I), (IV), and (V).

As discussed herein, the immunomodulatory compounds used in the methods of the invention elicit the production of cytokines such as IL-1α, IL-1β, IL-6, IL-10, IL12, interferon-α, interferon-γ, and GM-CSF. The cytokines IL-1α, IL-1β, and IL-10 are associated with the suppression of inflammatory responses, and agents that stimulate the production of these cytokines can be used to treat inflammatory conditions.

Inflammatory conditions that can be treated according to the methods of the invention include, but are not limited to, inflammatory bowel disease, multiple sclerosis, autoimmune diabetes, atopic dermatitis, urticaria, contact sensitivity, cutaneous allergic conditions, psoriasis, chronic adrenocortical disorder and hyperfunction, rheumatoid arthritis, lupus, pneumonia, bronchial asthma, hematological disorders, dermatitis and eczema.

The invention also provides immunostimulatory remedies comprising as the active ingredient a compound of the formulae (I), (II), (III), (IV), and (V).

The subject individual is preferably human, although the invention can be applied in veterinary applications to animal species, including mammals or avian species.

The specific formulation of therapeutically effective compositions of the present invention may thus be carried out in any suitable manner which will render the immunomodulatory compound or compounds bioavailable, safe and effective in the subject to whom the formulation is administered.

The modes of administration may comprise the use of any suitable means and/or methods for delivering the immunomodulatory compound to one or more corporeal loci of the host subject individual where the adjuvant and associated antigens are immunostimulatively effective. Delivery modes may include, without limitation, parenteral administration methods, such as subcutaneous (SC) injection, transmucosal, intranasal (IN), ophthalmic, transdermal, intramuscular (IM), intradermal (ID), intraperitoneal (IP), intravaginal, pulmonary, and rectal administration, as well as non-parenteral, e.g., oral, administration.

The dose rate and suitable dosage forms for the immunomodulatory compounds of the present invention may be readily determined by those of ordinary skill in the art without undue experimentation, by use of conventional antibody titer determination techniques and conventional bioefficacy/biocompatibility protocols, and depending on the desired therapeutic effect, and the desired time span of bioactivity.

The immunomodulatory compounds of the present invention may be usefully administered to the host subject individual with any other suitable pharmacologically or physiologically active agents, e.g., antigenic and/or other biologically active substances.

Formulations of the invention can include additional components such as saline, oil, squalene, oil-water dispersions, and the like.

Immunomodulatory Compounds of the Formulae (I), (II), (III) (IV), and (V)

The present invention is directed to methods of using immunomodulatory compounds of the formulae (I), (II), (III) (IV), and (V) and/or a pharmaceutically acceptable salt, hydrate, solvate, stereoisomer, amorphous solid thereof, or any combination thereof. The compounds of Formula (I), (II), (III), (IV) and (V) can function as adjuvants and/or as immunostimulatory compounds depending on the application in which they are used.

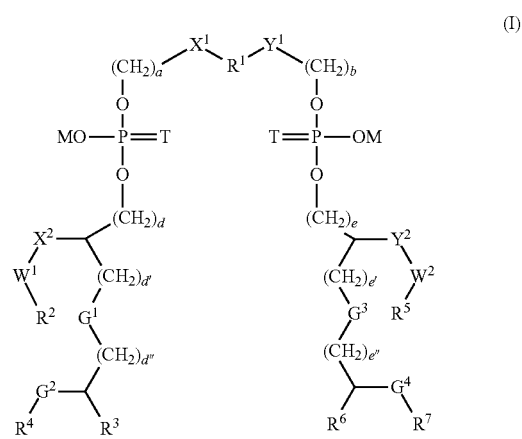

-continued

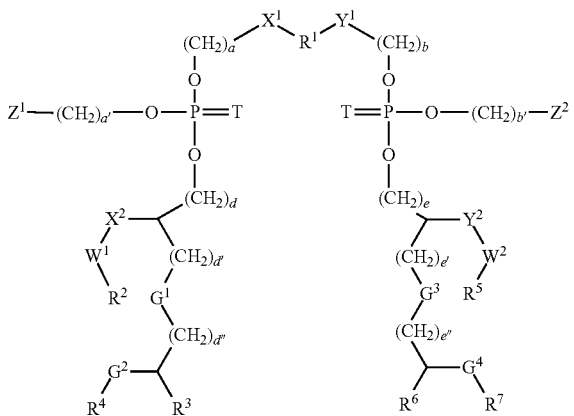
(II)

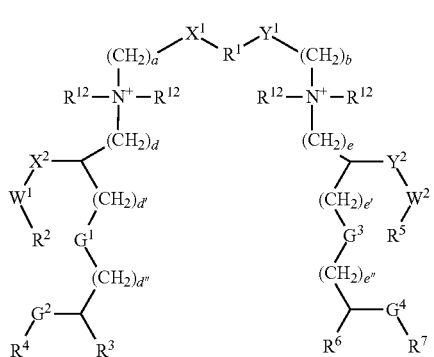
(III)

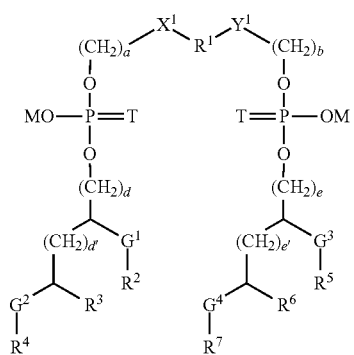
(IV)

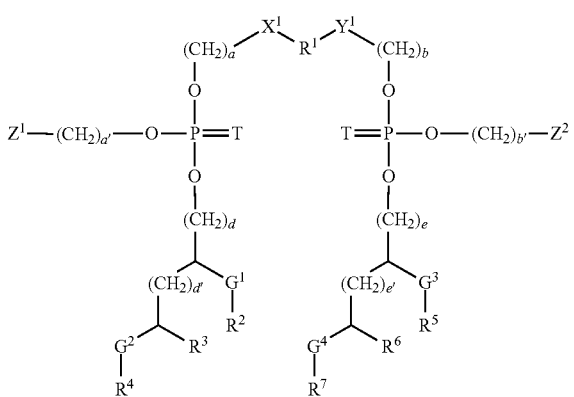
(V)

wherein:

$R^1$ is: (a) —C(O)—;

(b) —C(O)—$C_{1-14}$alkyl-C(O)— or —C(O)—$C_{1-14}$alkenyl-C(O)—;

wherein the —$C_{1-14}$alkyl- or —$C_{1-14}$alkenyl- is optionally substituted with one or more substituents selected from hydroxy, $C_{1-6}$alkyl, $C_{1-6}$alkoxy, $C_{1-6}$alkyldioxy, $C_{1-5}$ alkylamino, carboxy, $C_{1-6}$ alkoxycarbonyl, $C_{1-6}$ carbamoyl, $C_{1-6}$ acylamino, and/or (aryl)$C_{1-6}$-alkyl; and wherein the aryl moiety of the (aryl)$C_{1-6}$alkyl is optionally substituted with one or more substituents selected from $C_{1-6}$alkyl, $C_{1-6}$-alkoxy, $C_{1-6}$alkylamino, $C_{1-6}$alkoxyamino, $C_{1-6}$alkylamino-$C_{1-6}$alkoxy, —O—$C_{1-6}$alkylamino-$C_{1-4}$alkoxy, —O—$C_{1-6}$alkylamino-C(O)—$C_{1-6}$alkyl-C(O)OH, —O—$C_{1-6}$alkylamino-C(O)—$C_{1-6}$alkyl-C(O)—$C_{1-6}$alkyl, —O—$C_{1-6}$alkyl-NH—$C_{1-6}$alkyl-O—$C_{1-6}$ alkyl, —O—$C_{1-6}$alkyl-NH—C(O)$C_{1-6}$alkyl-C(O)OH, and/or —O—$C_{1-6}$alkyl-NH—C(O)—$C_{1-6}$alkyl-C(O)—$C_{1-6}$alkyl;

(c) a $C_2$ to $C_{15}$ straight or branched chain alkyl group optionally substituted with one or more hydroxy and/or alkoxy groups; or (d) —C(O)—$C_{6-12}$aryl-C(O)— wherein the aryl is optionally substituted with one or more hydroxy, halo (e.g., fluoro), nitro, amino, $C_{1-6}$alkyl and/or $C_{1-6}$alkoxy groups;

a and b are each independently 0, 1, 2, 3 or 4; (preferably 2);

a' and b' are independently 2, 3, 4, 5, 6, 7 or 8; (preferably 2);

d and e are each independently 1, 2, 3, 4, 5 or 6;

d' and e' are each independently 0, 1, 2, 3 or 4; (preferably 0, 1 or 2);

d" and e" are each independently 0, 1, 2, 3 or 4; (preferably 1, 2, 3 or 4);

T is oxygen or sulfur;

$X^1$, $X^2$, $Y^1$ and $Y^2$ are each independently null, oxygen, NH, —N(C(O)$C_{1-4}$alkyl)-, or —N($C_{1-4}$alkyl)-;

$W^1$ and $W^2$ are each independently carbonyl, methylene, sulfone or sulfoxide;

$R^2$, $R^3$, $R^4$, $R^5$, $R^6$ and $R^7$ are each independently:

(a) $C_2$ to $C_{20}$ straight chain or branched chain alkyl, which is optionally substituted with one or more oxo, halo (preferably fluoro), hydroxy and/or alkoxy groups;

(b) $C_2$ to $C_{20}$ straight chain or branched chain alkenyl, which is optionally substituted with one or more of oxo, halo (preferably fluoro), hydroxy and/or alkoxy groups;

(c) $C_2$ to $C_{20}$ straight chain or branched chain alkoxy, which is optionally substituted with one or more oxo, halo (e.g., fluoro), hydroxy and/or alkoxy groups;

(d) —NH—$C_{2-20}$ straight chain or branched chain alkyl, wherein the alkyl group is optionally substituted with one or more oxo, halo (e.g., fluoro), hydroxy and/or alkoxy groups;

(e) —C(O)—$C_{2-20}$ straight chain or branched chain alkyl or alkenyl, wherein the alkyl or alkenyl is optionally substituted with one or more oxo, halo (e.g., fluoro), hydroxy and/or alkoxy groups;

(f)

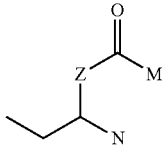

Z is O or NH; and M and N are each independently $C_2$ to $C_{20}$ straight chain or branched chain alkyl, alkenyl, alkoxy, acyloxy, alkylamino, or acylamino;

(g)

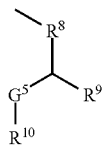

$R^8$ is $C_{1-6}$ straight or branched chain alkyl or $C_{2-6}$ straight or branched chain alkenyl or alkynyl;

$R^9$ and $R^{10}$ are independently selected from the group consisting of
(i) $C_1$ to $C_{20}$ straight chain or branched chain alkyl, which is optionally substituted with one or more halo, oxo, hydroxy and/or alkoxy; and
(ii) $C_2$ to $C_{20}$ straight chain or branched chain alkenyl or alkynyl which is optionally substituted with one or more halo, oxo, hydroxy and/or alkoxy;

$G^1$, $G^2$, $G^3$, $G^4$ and $G^5$ are each independently oxygen, methylene, —NH—, thiol, —N($C_{1-4}$alkyl)-, —N[C(O)—$C_{1-4}$alkyl]-, —NH—C(O)—, —NH—$SO_2$—, —C(O)—O—, —C(O)—NH—, —O—C(O)—, —O—C(O)—NH—, —O—C(O)—O—, —NH—C(O)—NH—, —C(O)NH—, —C(O)N($C_{1-4}$alkyl), aryl, and —S(O)$_n$—, where n is 0, 1, or 2;

or $G^1R^2$, $G^2R^4$, $G^3R^5$ and/or $G^4R^7$ may together be a hydrogen atom or hydroxyl;

$Z^1$ and $Z^2$ are each independently selected from —OP(O)(OH)$_2$, —P(O)(OH)$_2$, —OP(O)(OR$^8$)(OH) {where $R^8$ is a $C_{1-4}$alkyl}, —OS(O)$_2$OH, —S(O)$_2$OH—, —CO$_2$H, —OB(OH)$_2$, —OH, —CH$_3$, —NH$_2$, and —N(R$^9$)$_2$ {where $R^9$ is a $C_{1-4}$alkyl};

$R^{12}$ is H or a $C_{1-4}$ straight or branched alkyl; and

M is independently selected from a hydrogen atom and a pharmaceutically acceptable cation {a monovalent cation will take the place of one M, while a divalent cation will take the place of two M variables}.

In one embodiment, $R^1$ in the compounds of Formula (I)-(V) is —C(O)— or —C(O)—$C_{1-4}$alkyl-C(O)—. In another embodiment, $R^1$ in the compounds of Formula (I)-(V) is —C(O)—.

In one embodiment of the invention, T is oxygen in the compounds of Formula (I)-(V).

In another embodiment, $G^1$, $G^2$, $G^3$ and $G^4$ in the compounds of Formula (I)-(V) are each independently oxygen, —NH—, —NH—C(O)—, —C(O)—O—, —C(O)—NH—, —O—C(O)—, —(O)—C(O)—NH—, —O—C(O)—O—, —NH—C(O)—NH—, or —C(O)NH—. In another embodiment, $G^1$, $G^2$, $G^3$ and $G^4$ in the compounds of Formula (I)-(V) are each independently oxygen, —C(O)—O— or —O—C(O)—. In another embodiment, $G^1$ and $G^3$ in the compounds of Formula (I)-(V) are —O—C(O)—.

In one embodiment for the compounds of Formula (I)-(V) {preferably compounds of Formula (I)-(D)}, $R^2$ and $R^5$ are each independently substituents selected from (a), (b), (c), (d) and (f) in the definitions of $R^2$ and $R^5$ herein; $R^3$ and $R^6$ are each independently substituents selected from (a) and (b) in the definitions of $R^3$ and $R^6$ herein; and $R^4$ and $R^7$ are each independently substituents selected from (a), (b), (c) and (e) in the definitions of $R^4$ and $R^7$ herein.

In other embodiments for the compounds of Formula (I)-(V) {preferably compounds of Formula (IV) or (V)}, $R^2$, $R^3$, $R^4$, $R^5$, $R^6$ and $R^7$ are each independently substituents selected from (a), (b), (g) and (h) in the definitions of $R^2$, $R^3$, $R^4$, $R^5$, $R^6$ and $R^7$ herein.

In other embodiments for the compounds of Formulas (I)-(III), one or more of the following is present: each of a and b is 2; each of $X^1$ and $Y^1$ is NH; $R^1$ is —C(O)— or —C(O)—$C_{1-14}$alkyl-C(O)—; each of d' and e' is 1; each of d" and e" is 1; X is O or NH, more preferably NH; and W is C(O); or each of d' and e' are 2.

In other embodiments for Formulas (I)-(III), $R^1$ is a —C(O) $C_{1-14}$ alkyl-C(O)—, wherein the $C_{1-14}$alkyl is substituted, for example, with a $C_{1-5}$alkoxy group.

In one embodiment, the compounds of Formulas (I)-(III) are "Type 1" wherein the values of a and b are the same; the values of d and e are the same; the values of d' and e' are the same; the values of d" and e" are the same; $X^1$ and $Y^1$ are the same; $X^2$ and $Y^2$ are the same; $W^1$ and $W^2$ are the same; $R^2$ and $R^5$ are the same; $G^1$ and $G^3$ are the same; $R^3$ and $R^6$ are the same; $G^2$ and $G^4$ are the same; and $R^4$ and $R^7$ are the same.

In another embodiment, the compounds of Formulas (I)-(III) are "Type 2" wherein the values of a and b are different, the values of d and e are the same, the values of d' and e' are different; the values of d" and e" are the same; $X^1$ and $Y^1$ are different; $X^2$ and $Y^2$ are different; $W^1$ and $W^2$ are different; $R^2$ and $R^5$ are different; $G^1$ and $G^3$ are different; $R^3$ and $R^6$ are different; $G^2$ and $G^4$ are different; or $R^4$ and $R^7$ are different.

In another embodiment, the compounds of Formulas (I)—(III) are "Type 3" wherein the values of a and b are different, the values of d and e are different, the values of d' and e' are different; the values of d" and e" are different; $X^1$ and $Y^1$ are different; $X^2$ and $Y^2$ are different; $W^1$ and $W^2$ are different; $R^2$ and $R^5$ are different; $G^1$ and $G^3$ are different; $R^3$ and $R^6$ are different; $G^2$ and $G^4$ are different; or $R^4$ and $R^7$ are different.

In other embodiments, the compounds of Formulas (I), (II) and/or (III) are preferably:

ER 803022; a pharmaceutically acceptable salt thereof other than the sodium salt shown below; and/or the one or more sodium cations shown below can be replaced with hydrogen atoms:

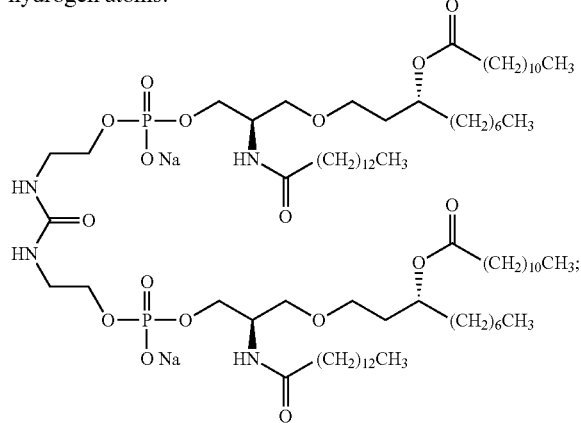

ER 803058; a pharmaceutically acceptable salt thereof other than the sodium salt shown below; and/or the one or more sodium cations shown below can be replaced with hydrogen atoms:

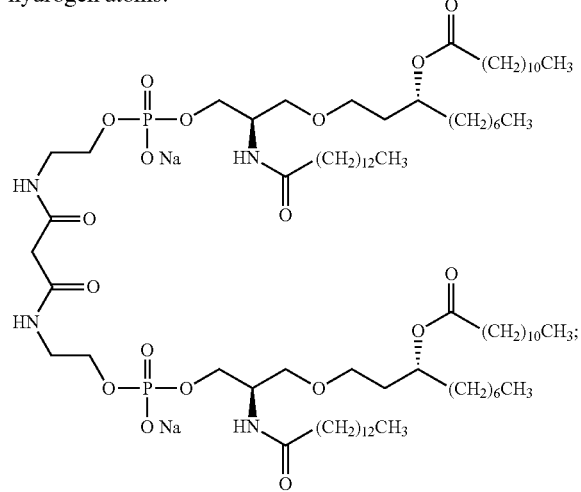

ER 803732; a pharmaceutically acceptable salt thereof other than the sodium salt shown below; and/or the one or more sodium cations shown below can be replaced with hydrogen atoms:

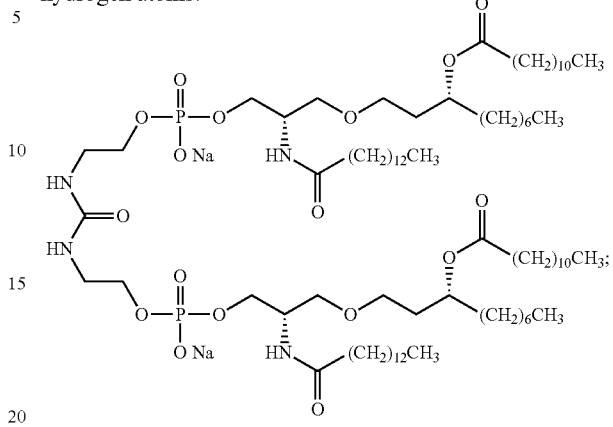

ER 804053; a pharmaceutically acceptable salt thereof other than the sodium salt shown below; and/or the one or more sodium cations shown below can be replaced with hydrogen atoms:

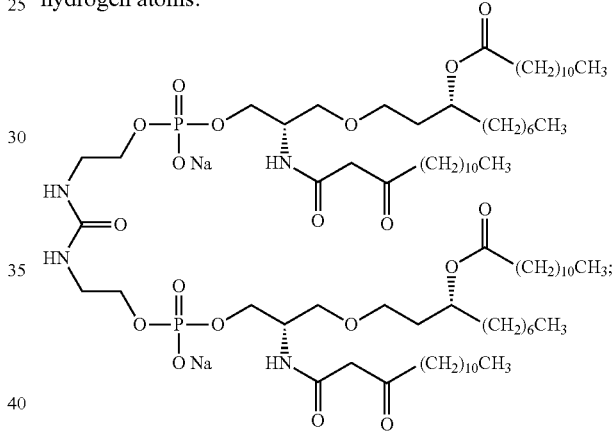

ER 804058; a pharmaceutically acceptable salt thereof other than the sodium salt shown below; and/or the one or more sodium cations shown below can be replaced with hydrogen atoms:

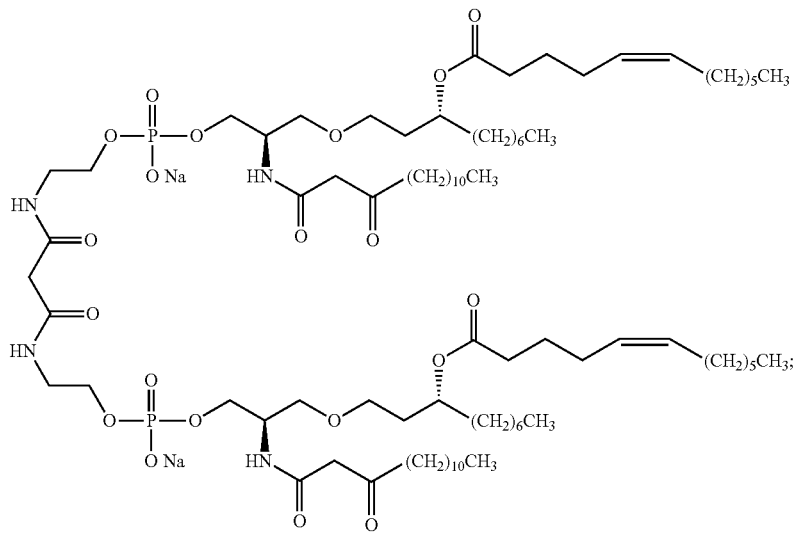

ER 804059; a pharmaceutically acceptable salt thereof other than the sodium salt shown below; and/or the one or more sodium cations shown below can be replaced with hydrogen atoms:

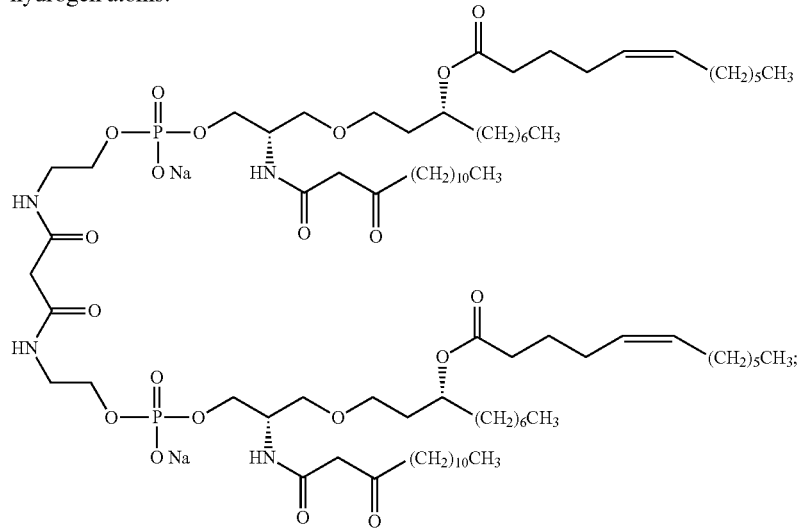

ER 804442; a pharmaceutically acceptable salt thereof other than the sodium salt shown below; and/or the one or more sodium cations shown below can be replaced with hydrogen atoms:

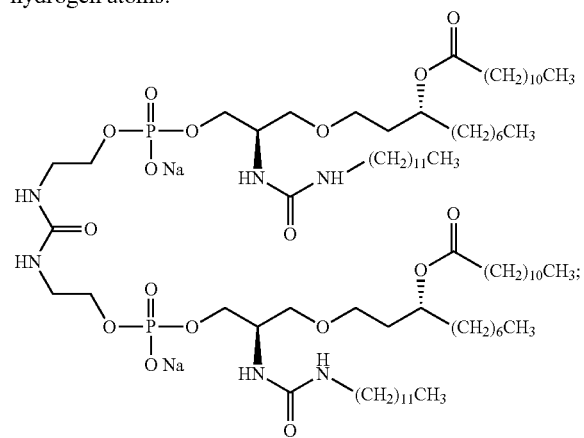

ER 804764; a pharmaceutically acceptable salt thereof other than the sodium salt shown below; and/or the one or more sodium cations shown below can be replaced with hydrogen atoms:

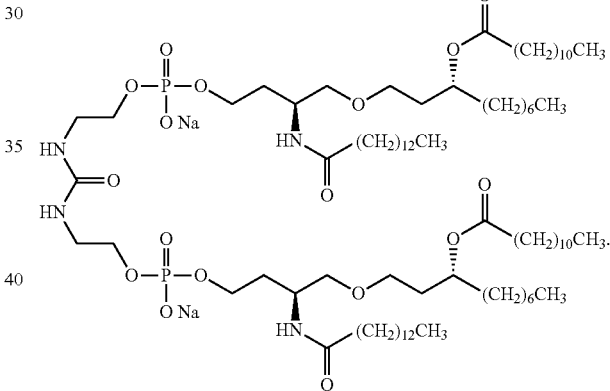

In one embodiment, the preferred compound is 112066; a stereoisomer thereof; a pharmaceutically acceptable salt thereof other than the sodium salt shown below; and/or the one or more sodium cations shown below can be replaced with hydrogen atoms:

ER 804680; a pharmaceutically acceptable salt thereof other than the sodium salt shown below; and/or the one or more sodium cations shown below can be replaced with hydrogen atoms:

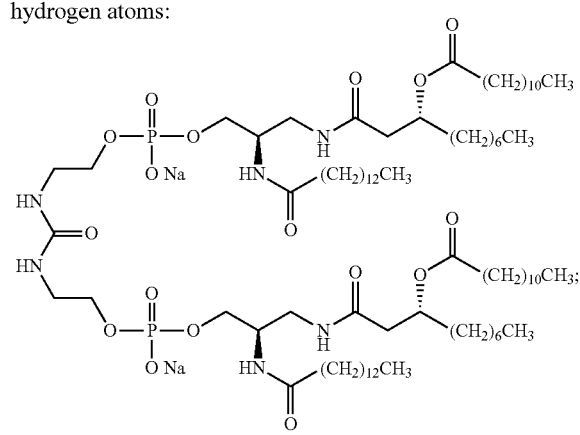

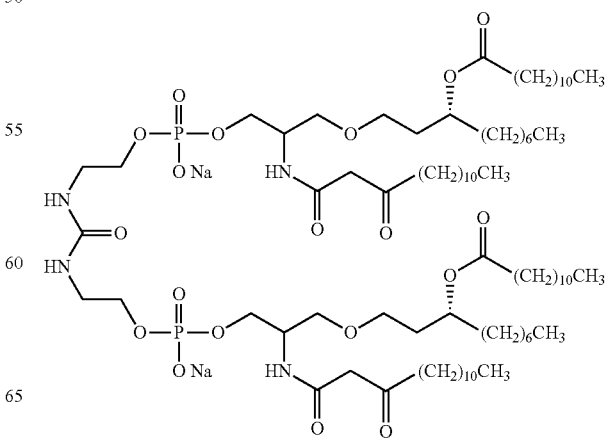

In one embodiment, the preferred compound is ER 804057; a pharmaceutically acceptable salt thereof other than the sodium salt shown below; or the one or more sodium cations shown below can be replaced with hydrogen atoms:

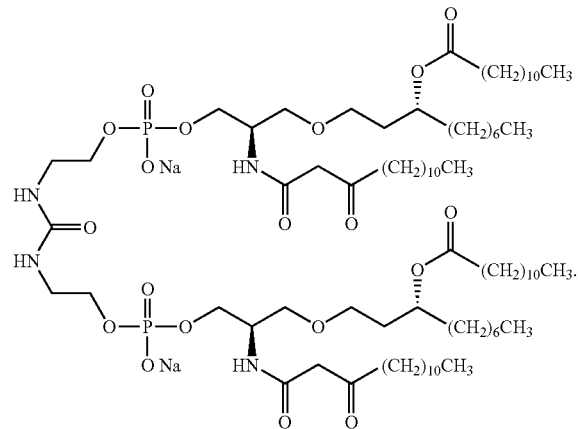

In some embodiments for Formula (IV) and (V), one or more of the following limitations is present: each of a and b is 2; each of $X^1$ and $Y^1$ is NH; each of d and e is 1 or 2; and each of d' and e' is 0, 1, or 2. In certain embodiments, each of d and e is 1 and each of d' and e' is 0. In certain other preferred embodiments, each of d and e is 1 and each of d' and e' is 1 or 2.

In some embodiments for Formulas (IV) and (V), $R^1$ is —C(O)— or —C(O)—$C_{1-14}$alkyl-C(O), wherein the $C_{1-14}$alkyl is optionally substituted with one or two substituents selected from the group consisting of hydroxy, $C_{1-6}$alkoxy, $C_{1-6}$alkyldioxy, $C_{1-6}$alkylamino, or (aryl)$C_{1-6}$alkyl, wherein the aryl moiety of the (aryl)$C_{1-6}$alkyl is optionally substituted with $C_{1-6}$alkyl, $C_{1-6}$alkoxy, $C_{1-6}$alkylamino, $(C_{1-6}$alkoxy)$C_{1-6}$alkylamino, $(C_{1-6}$alkylamino)$C_{1-4}$alkoxy, —O—$C_{1-6}$-alkyl-NH—C-alkyl-O—$C_{1-6}$alkyl, —O—$C_{1-6}$alkyl-NH—C(O)$C_{1-6}$alkyl-C(O)OH, or —O—$C_{1-6}$alkyl-NH—C(O)—$C_{1-6}$alkyl-C(O)$C_{1-6}$-alkyl.

In some embodiments for Formulas (IV) and (V), $G^1$, $G^2$, $G^3$, and $G^4$ are each independently selected from the group consisting of —NH—C(O)— and —O—C(O)—.

In some embodiments for Formula (IV) and (V), at least two of $R^2$, $R^3$, $R^4$, $R^5$, $R^6$, $R^7$, $R^9$ and $R^{10}$ are $C_{6-20}$ straight or branched chain alkyl, alkenyl, or alkynyl; any of which may optionally be substituted with one or more substituents selected from the group consisting of halo, oxo, hydroxy and/or alkoxy. In other embodiments, at least two of $R^2$, $R^3$, $R^4$, $R^5$, $R^6$, $R^7$, $R^9$ and $R^{10}$ are $C_{8-15}$ straight or branched chain alkyl, alkenyl, or alkynyl; any of which may optionally be substituted with one or more substituents selected from the group consisting of halo, oxo, hydroxy and alkoxy.

In some embodiments for Formulas (IV) and (V), at least four of $R^2$, $R^3$, $R^4$, $R^5$, $R^6$, $R^7$, $R^9$ and $R^{10}$ are $C_{6-20}$ straight or branched chain alkyl, alkenyl, or alkynyl; any of which may optionally be substituted with one or more substituents selected from the group consisting of halo, oxo, hydroxy and alkoxy. In certain preferred embodiments, at least four of $R^2$, $R^3$, $R^4$, $R^5$, $R^6$, $R^7$, $R^9$ and $R^{10}$ are $C_{8-15}$ straight or branched chain alkyl, alkenyl or alkynyl; any of which may optionally be substituted with one or more substituents selected from the group consisting of halo, oxo, hydroxy and alkoxy.

In some embodiments for Formulas (IV) and (V), at least six of $R^2$, $R^3$, $R^4$, $R^5$, $R^6$, $R^7$, $R^9$ and $R^{10}$ are $C_{6-20}$ straight or branched chain alkyl, alkenyl, or alkynyl; any of which may optionally be substituted with one or more substituents selected from the group consisting of halo, oxo, hydroxy and alkoxy. In other embodiments, at least six of $R^2$, $R^3$, $R^4$, $R^5$, $R^6$, $R^7$, $R^9$ and $R^{10}$ are $C_{8-15}$ straight or branched chain alkyl, alkenyl or alkynyl; any of which may optionally be substituted with one or more substituents selected from the group consisting of halo, oxo, hydroxy and alkoxy.

In other embodiments, the invention provides compounds of Formula (I), (II), (III), (IV) or (V) wherein T is sulfur. In other embodiments, the invention provides compounds of Formula (I), (II), (II), (IV) or (V) wherein T is sulfur; provided that the compound is not Compound No. 804678.

In another embodiment of the invention, there is a proviso that the compounds of Formula (I), (II) or (III) are not:

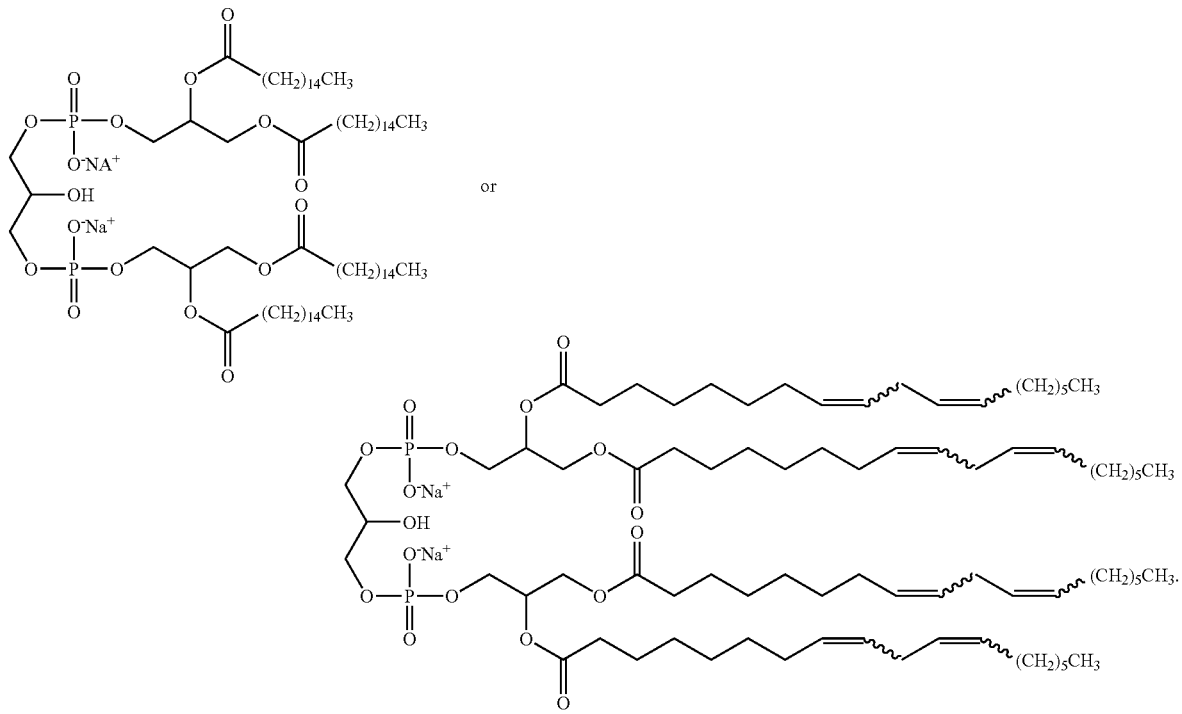

As used herein, the term "alkyl" includes substituted or unsubstituted, straight or branched chain monovalent or bivalent aliphatic hydrocarbon groups. One skilled in the art will appreciate the distinction between a monovalent alkyl group and a bivalent alkyl group in view of the context of the term "alkyl" in the definition for any particular substituent. When an alkyl is a terminal group, it will be monovalent, such as —$CH_3$, —$CH_2CH_3$, —$CH_2CH_2CH_3$, —$CH_2CH_2CH_2CH_3$, and the like. When an alkyl is between other moieties, such as "—C(O)—$C_{1-4}$alkyl-C(O)—" in the definition of $R^1$, the alkyl group will be bivalent, such as —$CH_2$—, —$CH_2CH_2$—, —$CH_2CH_2CH_2$—, —$CH_2CH_2CH_2CH_2$—, and the like.

As used herein, the term "alkenyl" includes substituted or unsubstituted, straight or branched chain unsaturated monovalent or bivalent aliphatic hydrocarbon groups. The "alkenyl" group can have any number of carbon-carbon double bonds, preferably one or two. One skilled in the art will appreciate the distinction between a monovalent alkenyl group and a bivalent alkenyl group in view of the context of the term "alkenyl" in the definition for any particular substituent. When an alkenyl is a terminal group, it will be monovalent, such as —CH=$CH_2$, —CH=CH$CH_3$, and the like. When an alkenyl is between other moieties, such as "—O(O)—$C_{1-14}$alkenyl-C(O)—" in the definition of $R^1$, the alkenyl group will be bivalent, such as —CH=CH—, —CH=CH$CH_2$—, —$CH_2$CH=CH$CH_2$—, and the like.

As used herein, the term "aryl" includes substituted or unsubstituted, monovalent or bivalent aromatic hydrocarbon groups. One skilled in the art will appreciate the distinction between a monovalent aryl group and a bivalent aryl group in view of the context of the term "aryl" in the definition for any particular substituent. When an aryl is a terminal group, it will be monovalent. When an aryl is between other moieties, such as "—C(O)—$C_{6-12}$aryl-C(O)—" in the definition of $R^1$, the aryl group will be bivalent. Boc is t-butyloxycarbonyl.

Null with reference to a given substituent means that the substituent is absent, and the chemical groups between which the substituent is positioned are directly attached to each other by way of a covalent bond.

The compounds of Formulas (I), (II), (III), (IV) and (V) may have one or more asymmetric carbon atoms, depending upon the substituents, and can have stereoisomers, which are within the scope of the invention. The compounds of Formulas (I), (II), (III), (IV) and/or (V) can be administered in the form of a pharmaceutically acceptable salt (e.g., where M in the compounds of Formulas (I), (II), (III), (IV) and/or (V) is a pharmaceutically acceptable cation). The compounds of Formulas (I), (II), (III), (IV) and/or (V) can be administered in the form of a pharmaceutically acceptable salt of a stereoisomer of the compounds. "Pharmaceutically acceptable salt" refers to salts which retain their biological effectiveness. Pharmaceutically acceptable base addition salts can be prepared from inorganic and organic bases. Exemplary pharmaceutically acceptable salts derived from inorganic bases include sodium, potassium, lithium, ammonium, calcium and magnesium salts. Exemplary salts derived from organic bases include salts of primary, secondary and tertiary amines. Pharmaceutically acceptable acid addition salts may be prepared from inorganic and organic acids. Exemplary salts derived from inorganic acids include hydrochloric acid, hydrobromic acid, sulfuric acid, nitric acid, phosphoric acid, and the like. Exemplary salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Methods for making the compounds of Formulas (I), (II), (III), (IV) and (V) are described in US Publication No. 2004/0006242, US Publication No. 2003/0153532, US Publication No. 2002/0176861, US Publication No. 2002/0049314, U.S. Pat. No. 6,551,600, U.S. Pat. No. 6,521,776, U.S. Pat. No. 6,290,973, and WO 03/099195, the disclosures of which are incorporated by reference herein in their entirety. Some compounds of Formulas (I), (II), (III), (IV) and (V) and methods for making them are also described by Hawkins et al, *The Journal of Pharmacology and Experimental Therapeutics*, 300(2): 655-661 (2000); Lien et al, *The Journal of Biological Chemistry*, 276(3): 1873-1880 (2001); Przetak et al, *Vaccine*, 21: 961-970 (2003); and Seydel et al, *Eur. J. Immunol.*, 33: 1586-1592 (2003), the disclosures of which are incorporated by reference herein in their entirety.

Exemplary compounds falling within the scope of the compounds of Formulas (I)-(V) are set forth below.

| No. | Structure |
|---|---|
| 112022 | 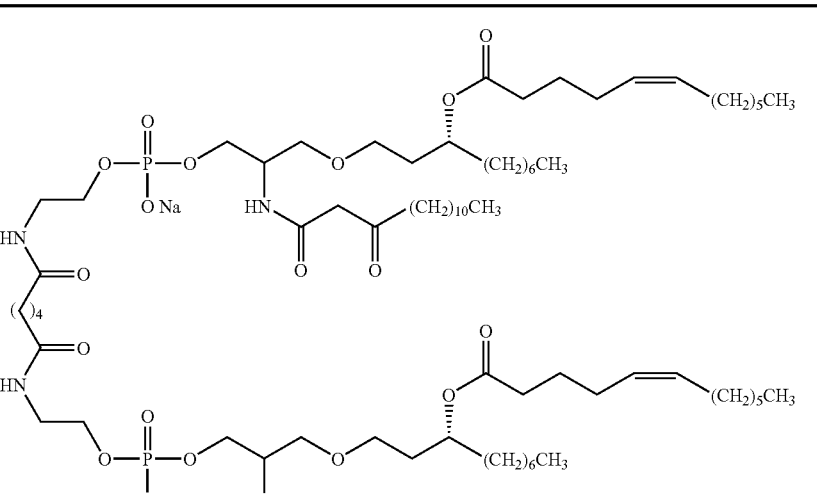 |

| No. | Structure |
|---|---|
| 111230 | 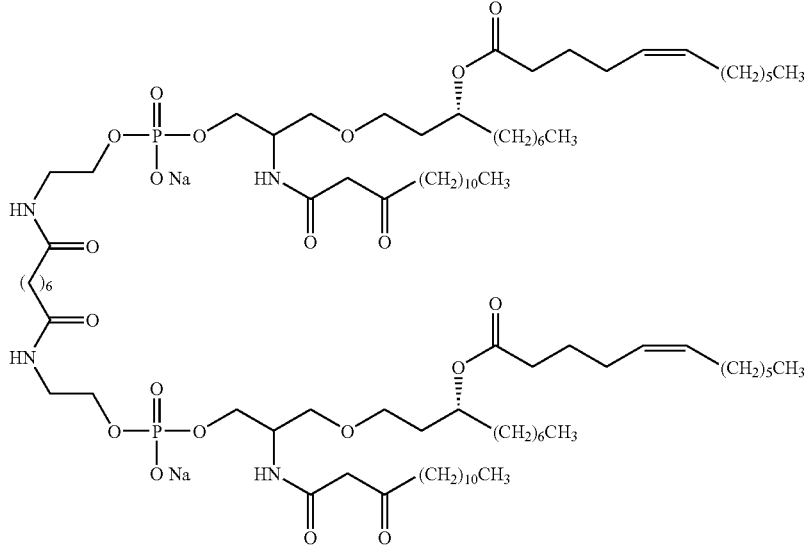 |
| 111231 | 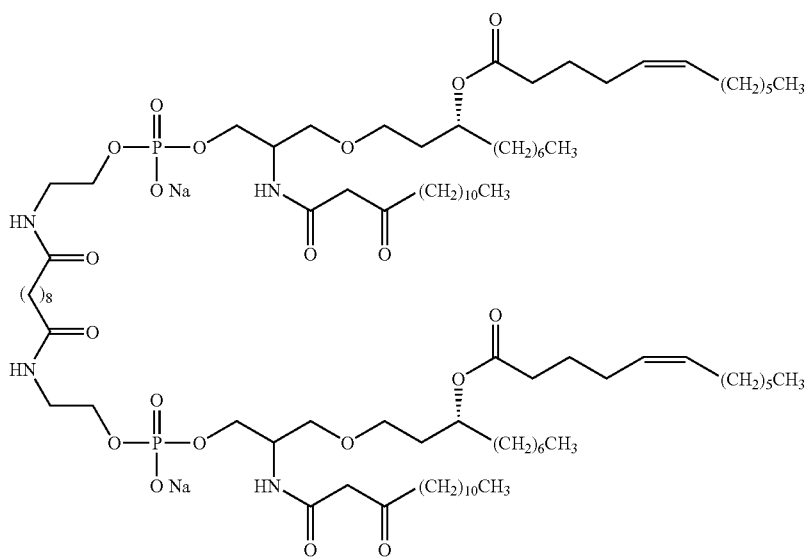 |
| 111232 | 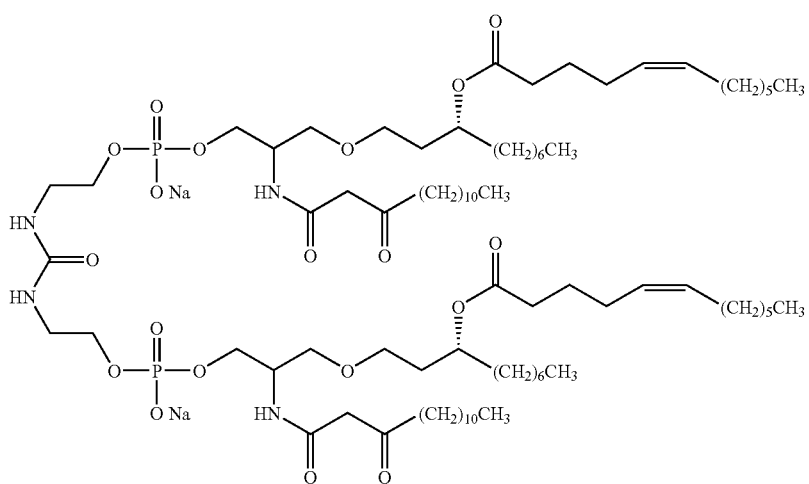 |

| No. | Structure |
|---|---|
| 111233 | 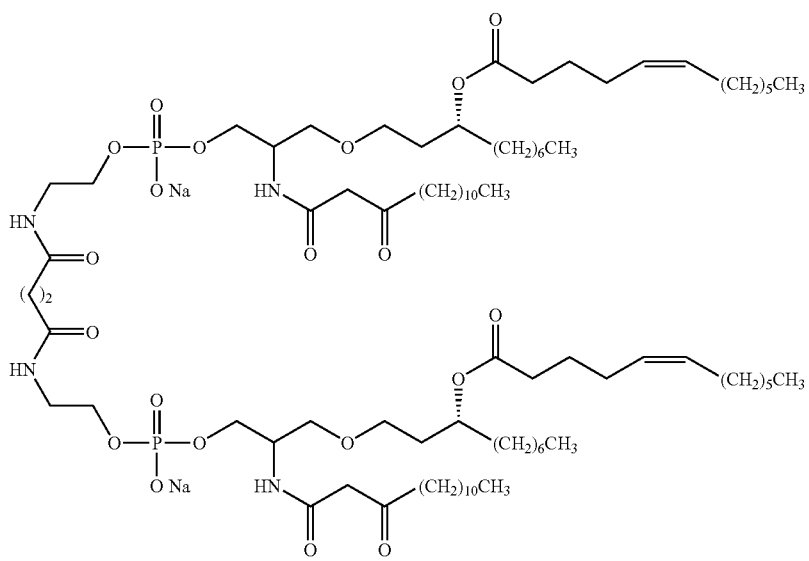 |
| 112043 | 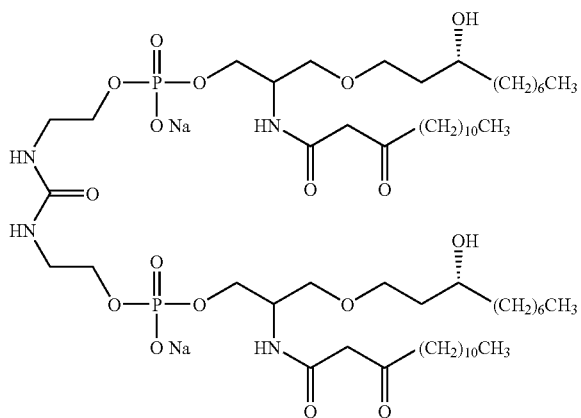 |
| 112044 | 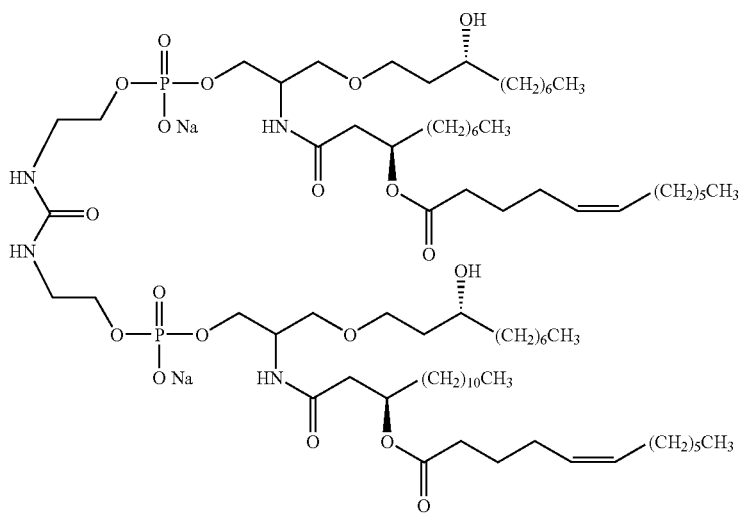 |

| No. | Structure |
|---|---|
| 112047 | 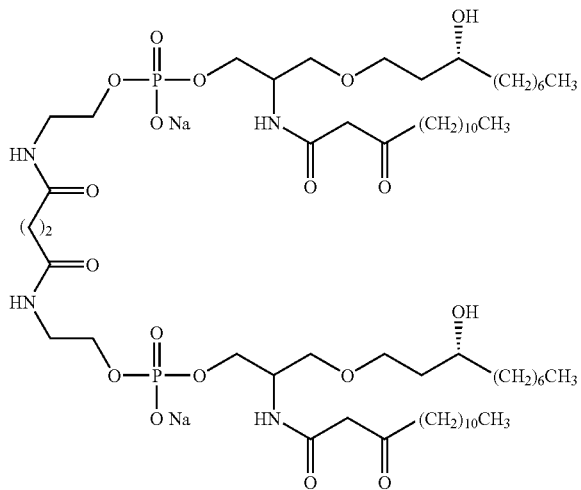 |
| 112048 | 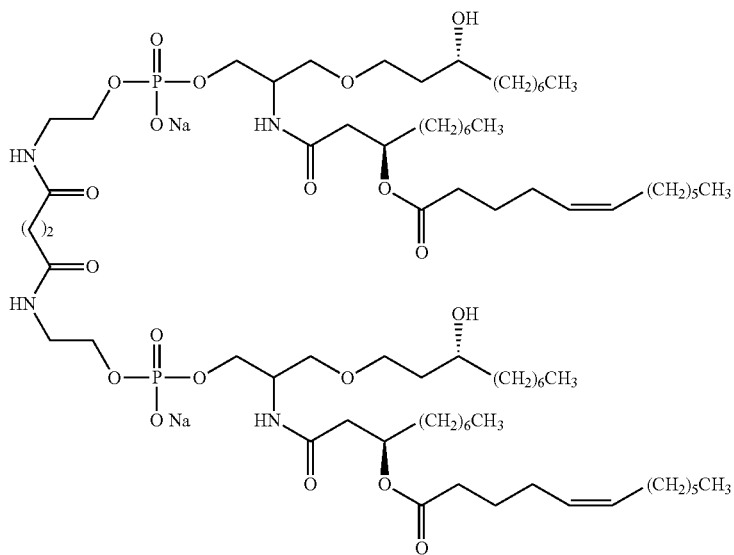 |
| 112049 | 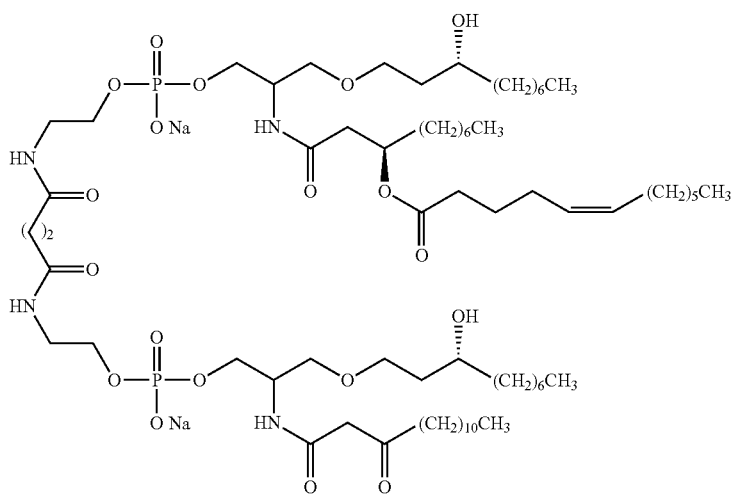 |

| No. | Structure |
|---|---|
| 112063 | 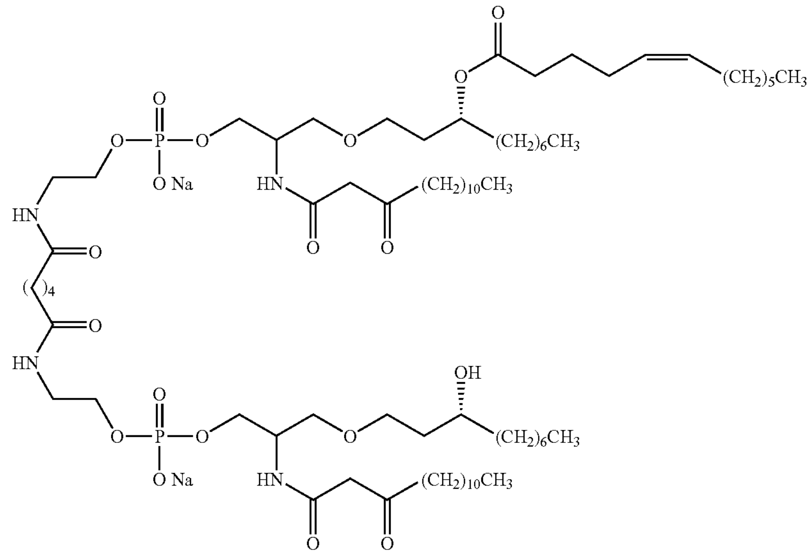 |
| 112064 | 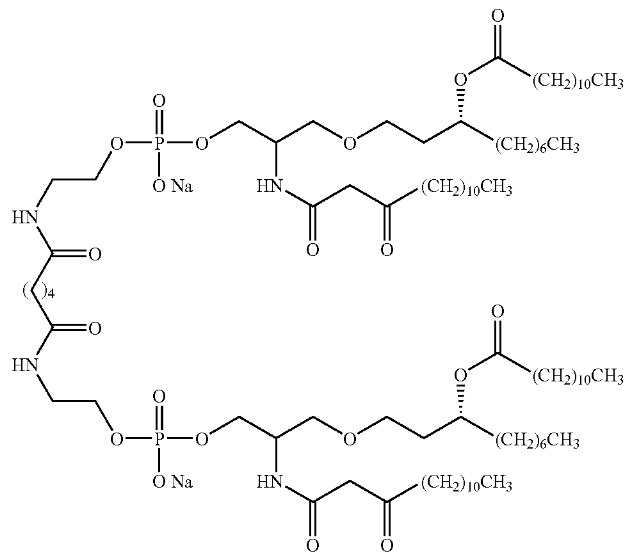 |
| 112065 | 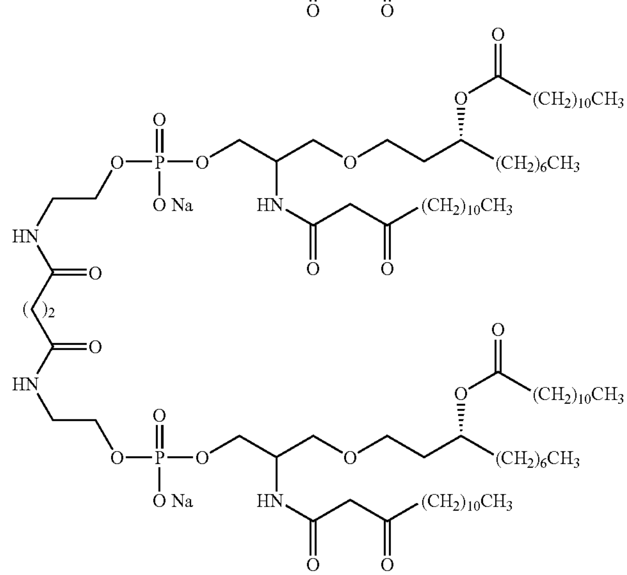 |

| No. | Structure |
|---|---|
| 112066 | 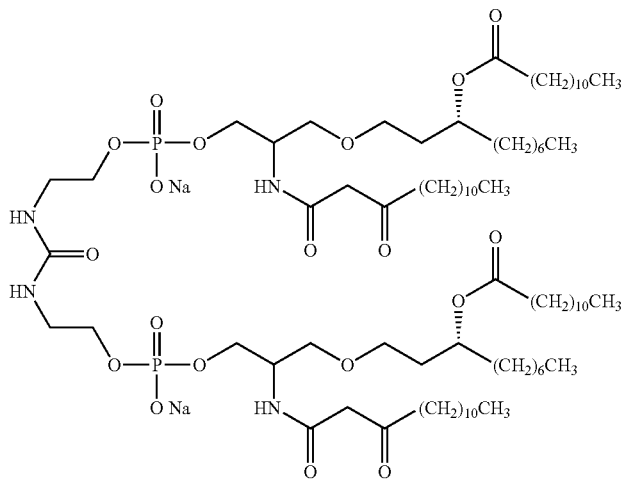 |
| 112071 | 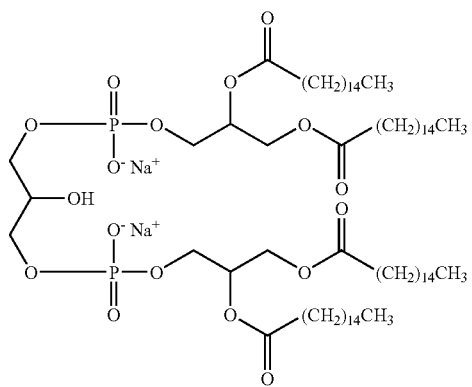 |
| 112072 | 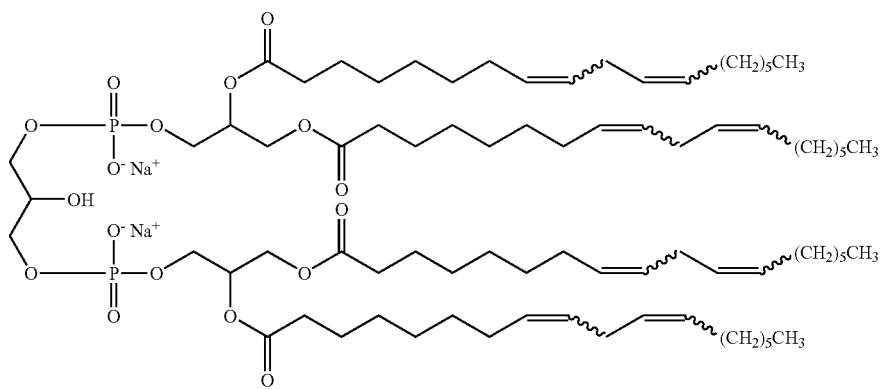 |

| No. | Structure |
|---|---|
| 112091 | 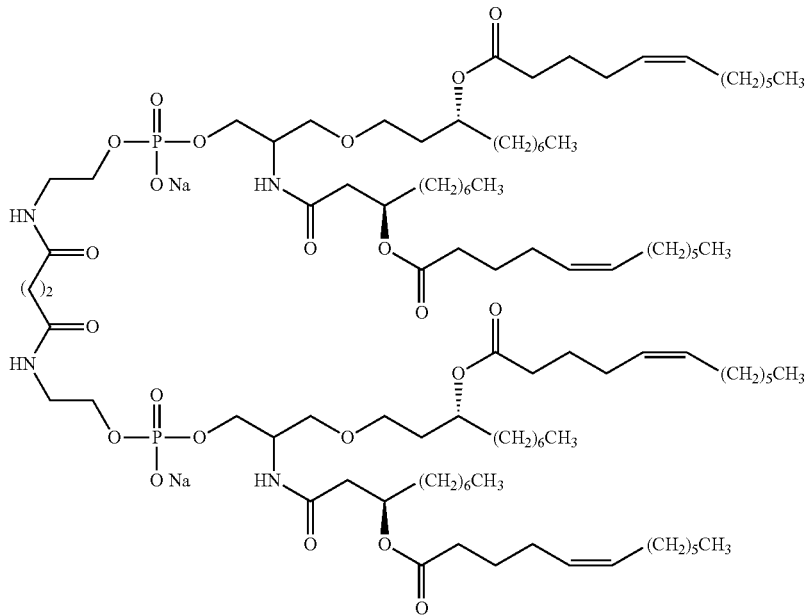 |
| 112092 | 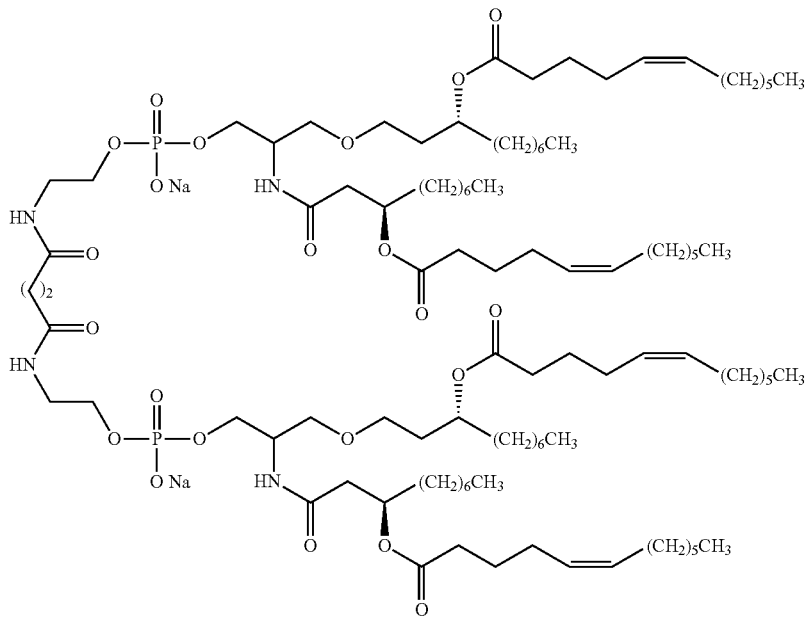 |

-continued
| No. | Structure |
|---|---|
| 112093 | 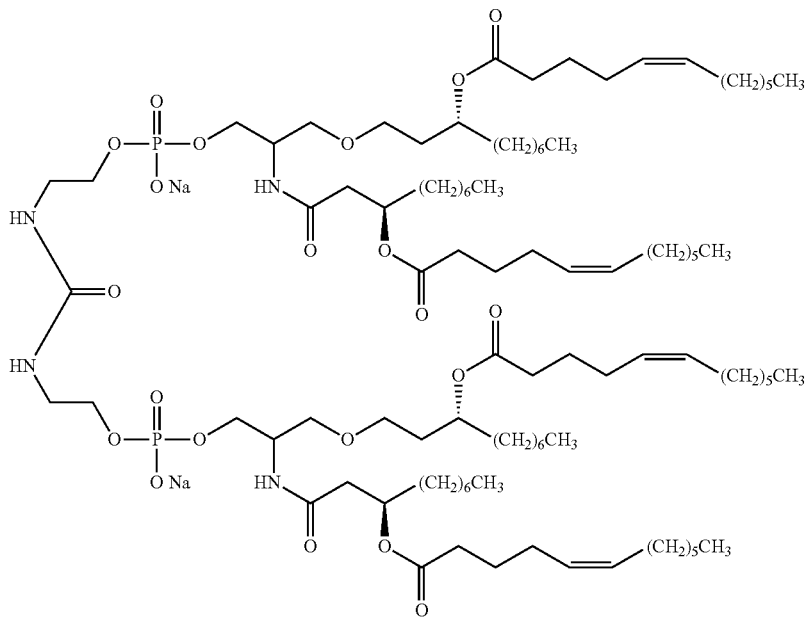 |
| 112098 | 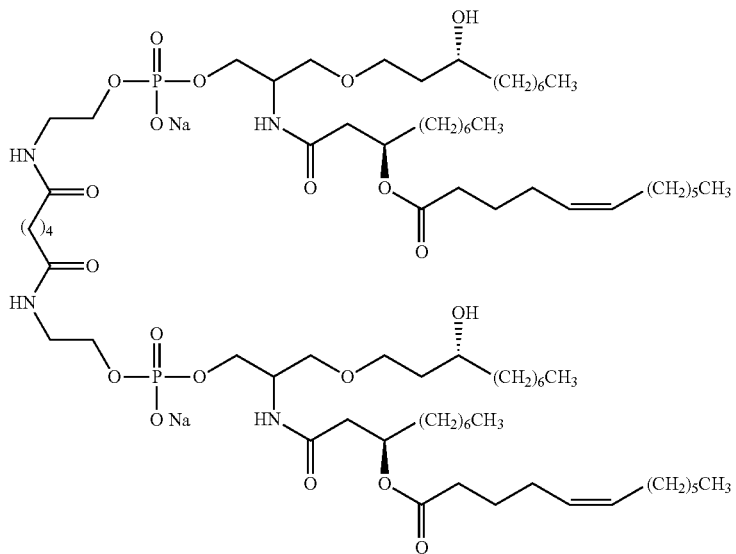 |

-continued
| No. | Structure |
|---|---|
| 112099 | 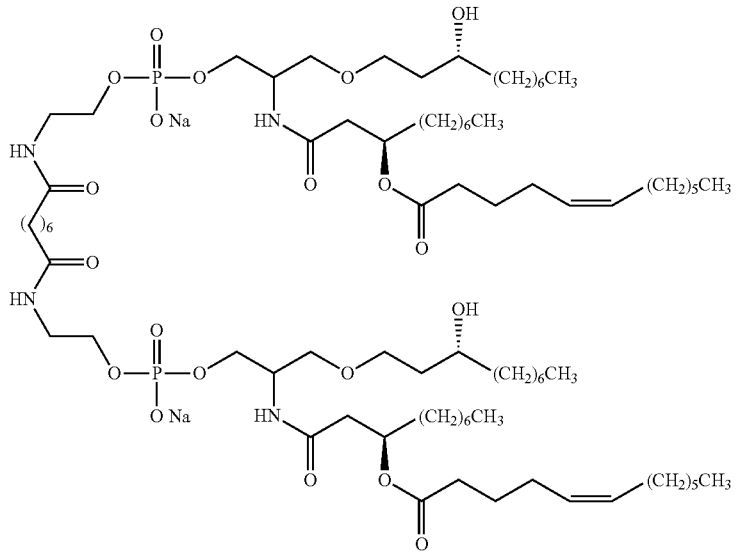 |
| 112100 | 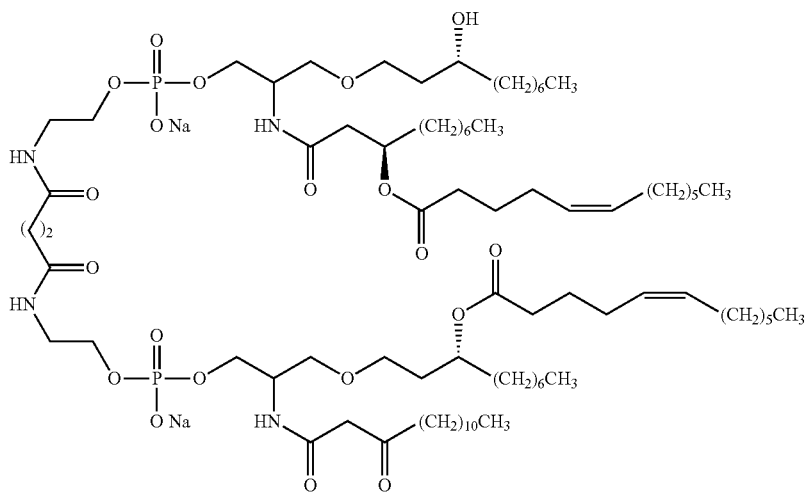 |
| 112859 | 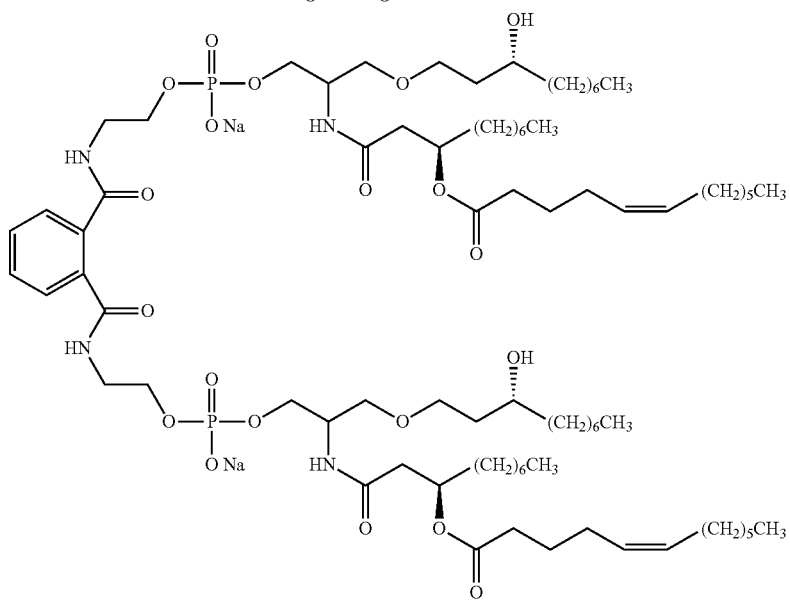 |

| No. | Structure |
|---|---|
| 112860 | 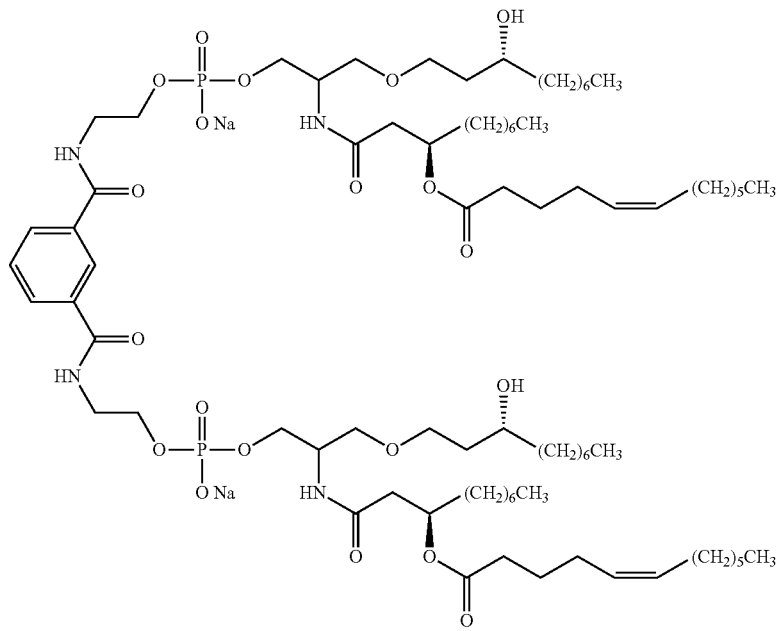 |
| 112861 | 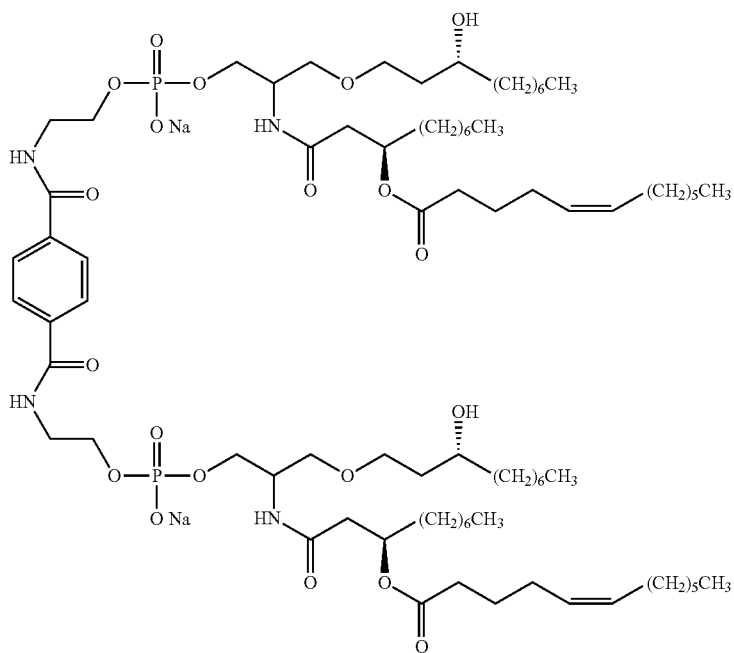 |

| No. | Structure |
|---|---|
| 113634 | 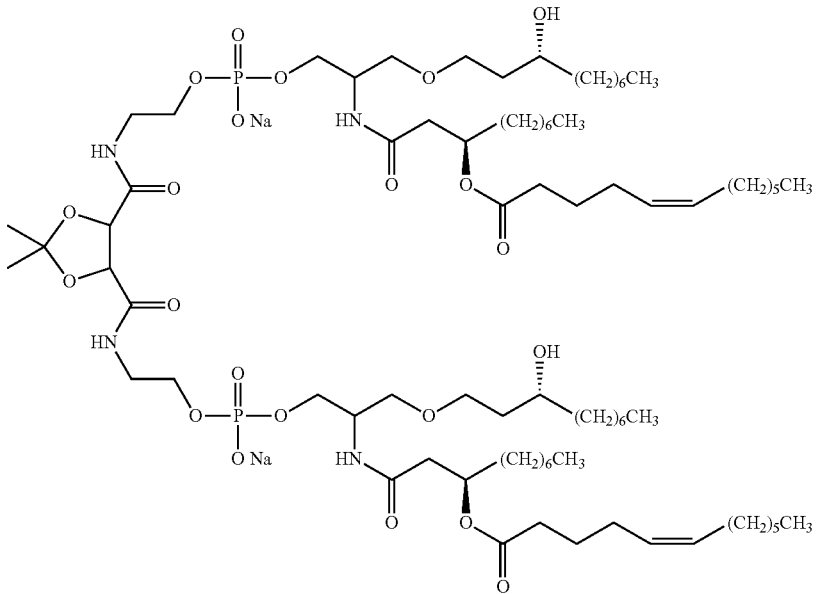 |
| 113635 | 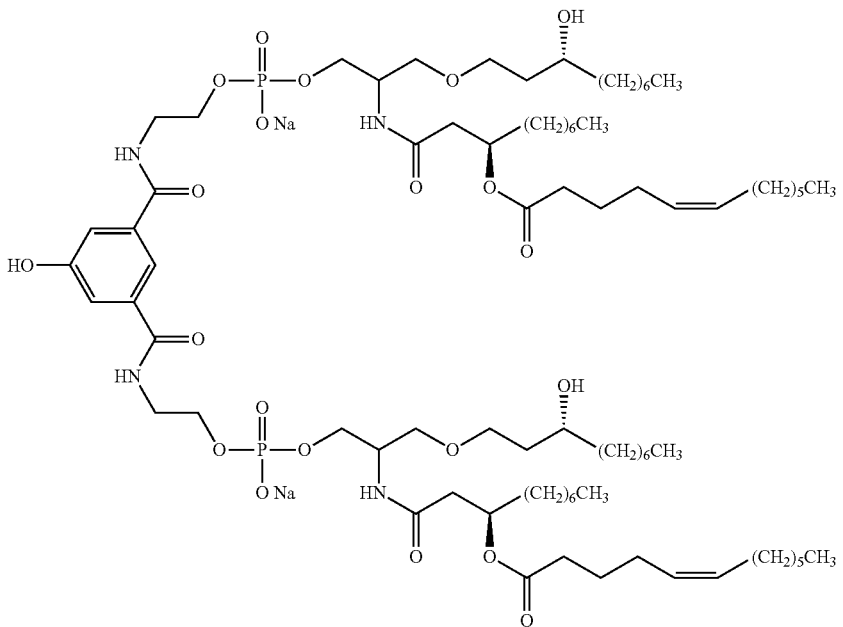 |

| No. | Structure |
|---|---|
| 113643 | 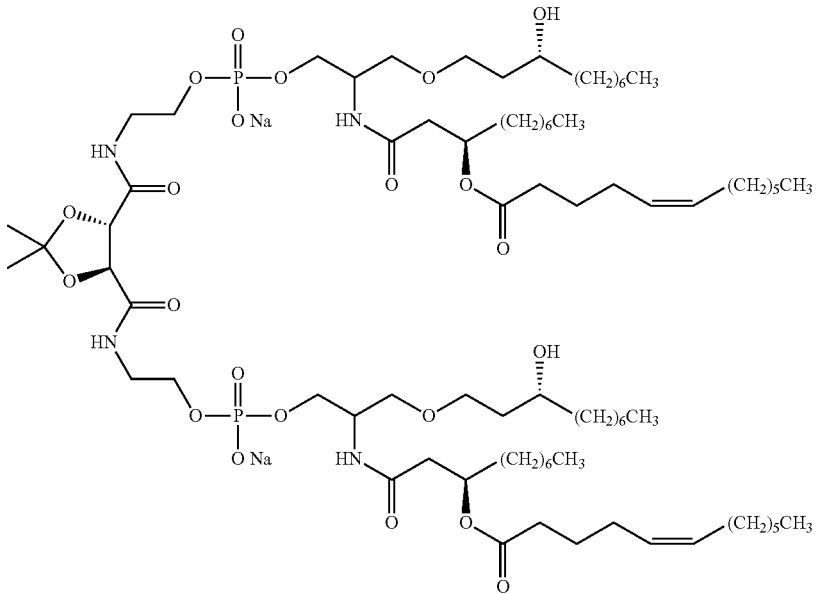 |
| 113644 | 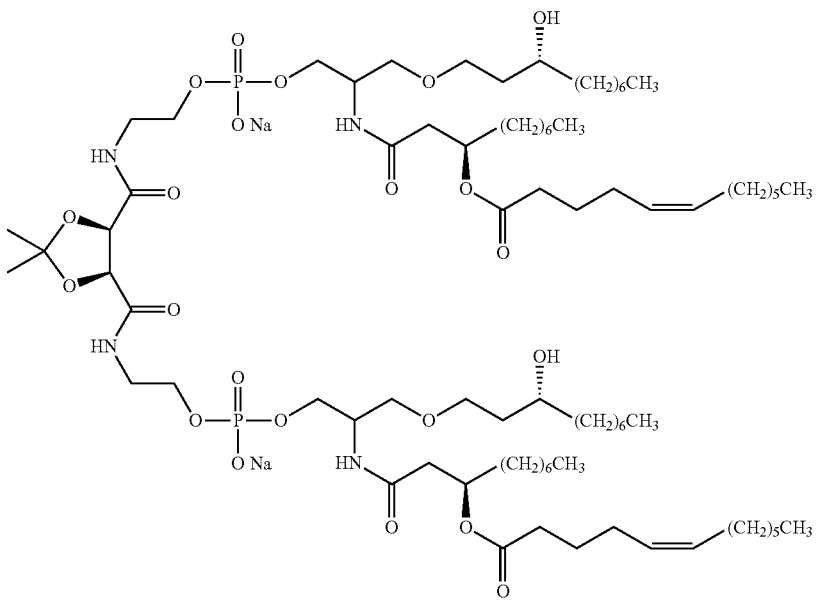 |

| No. | Structure |
|---|---|
| 113651 | 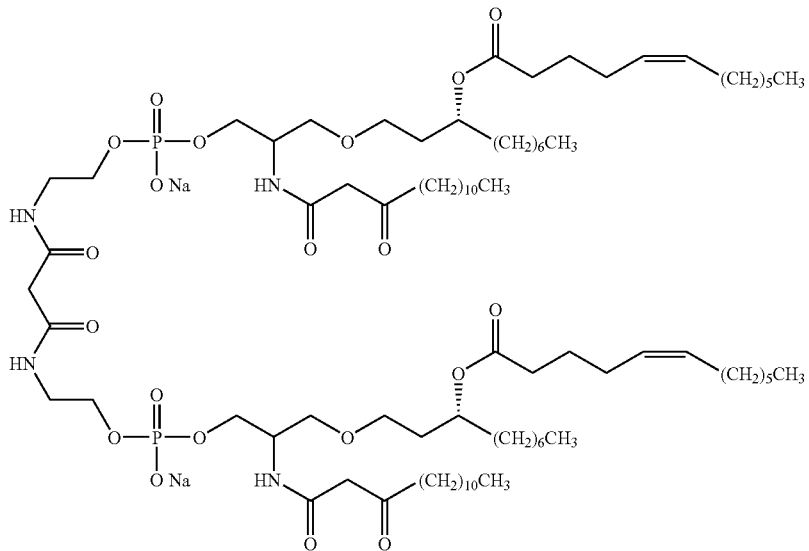 |
| 113665 | 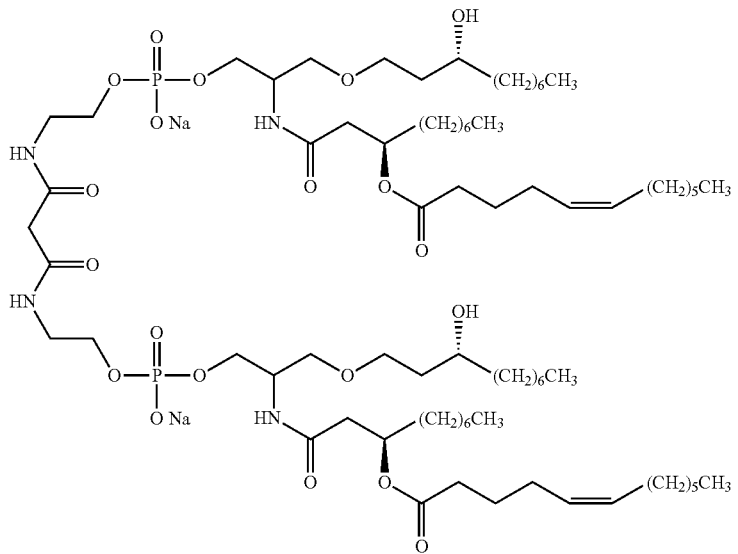 |

-continued
| No. | Structure |
|---|---|
| 113666 | 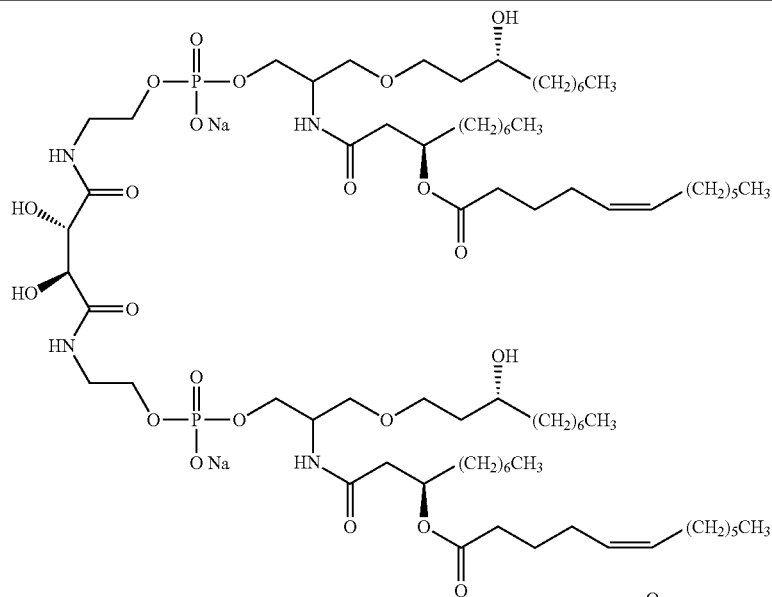 |
| 118023 | 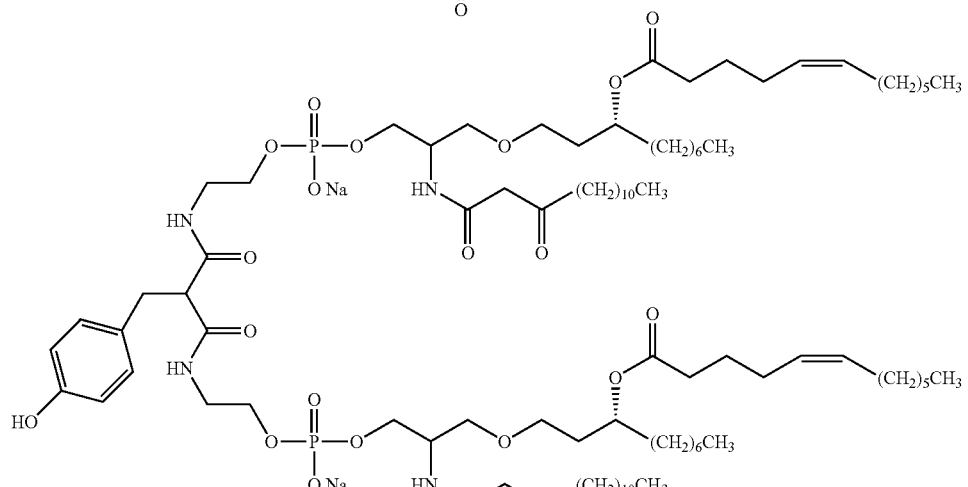 |
| 019772 | 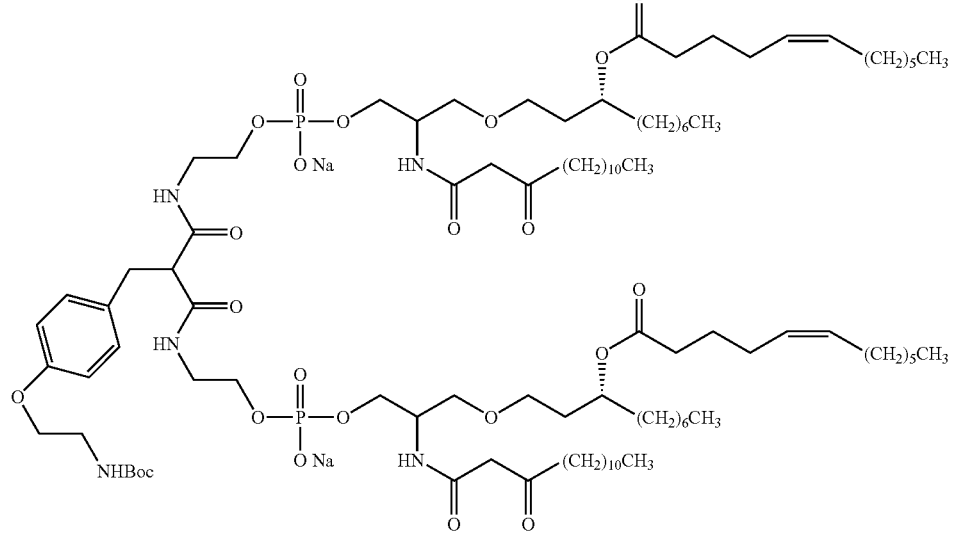 |

-continued
| No. | Structure |
|---|---|
| 118989 | 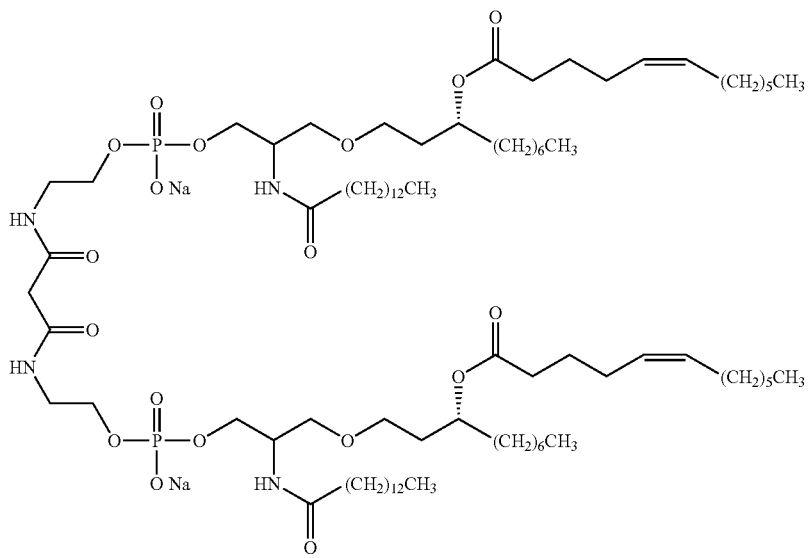 |
| 118999 | 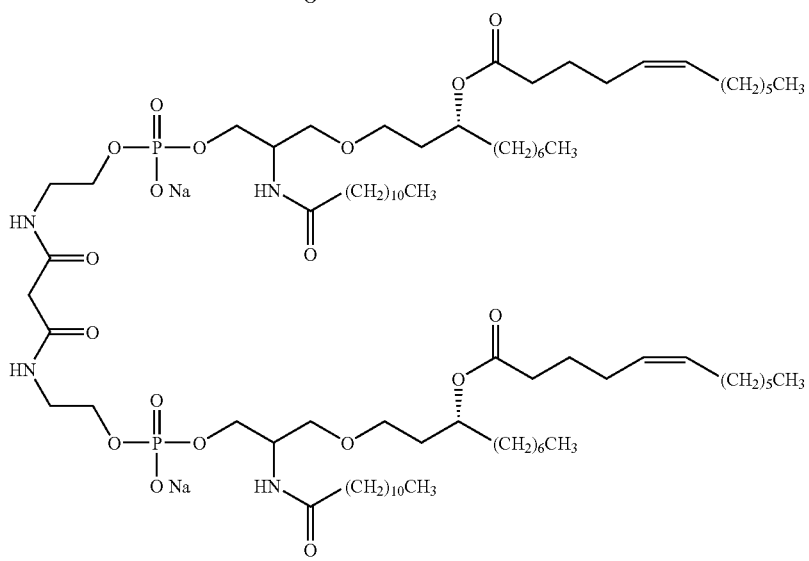 |
| 119000 | 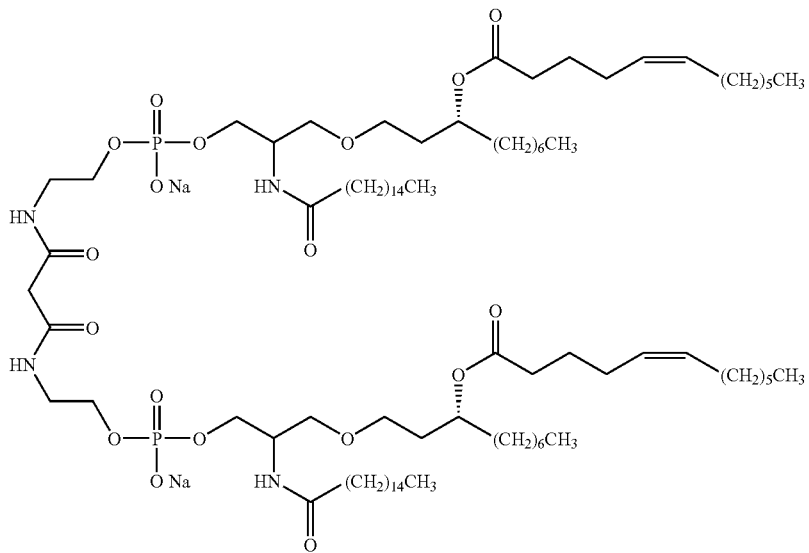 |

| No. | Structure |
|---|---|
| 119001 | 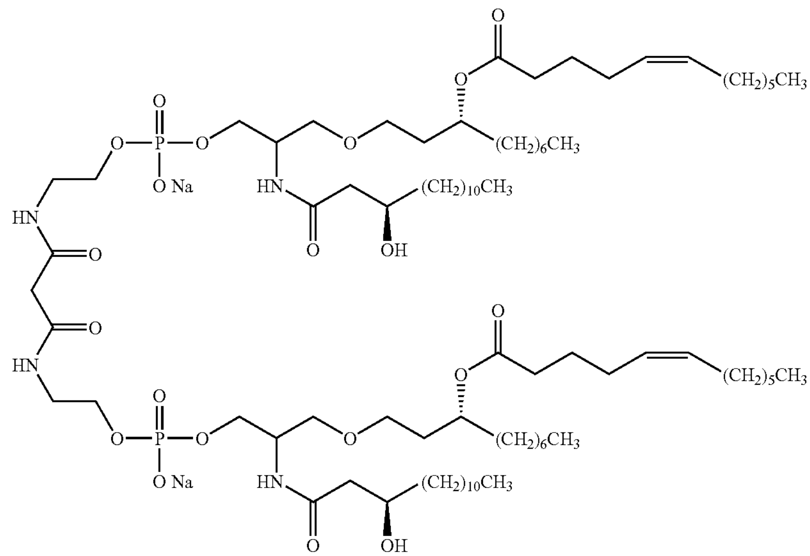 |
| 118949 | 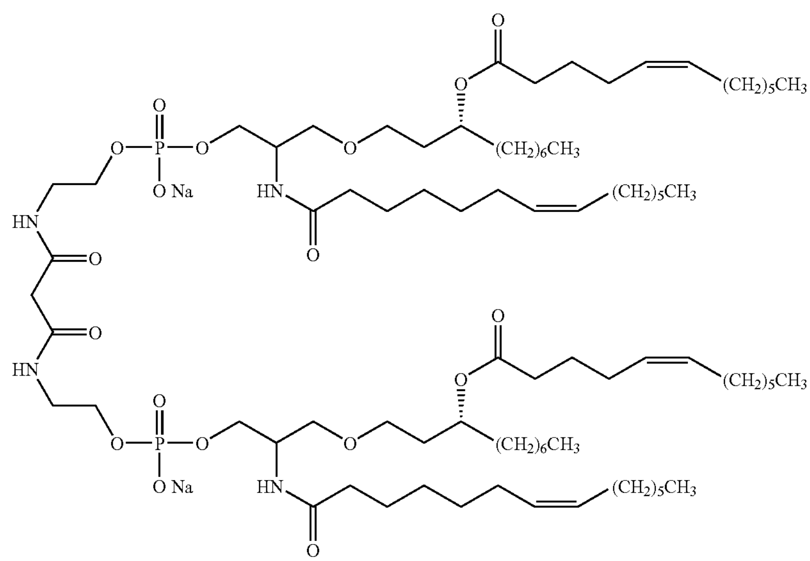 |
| 119327 | 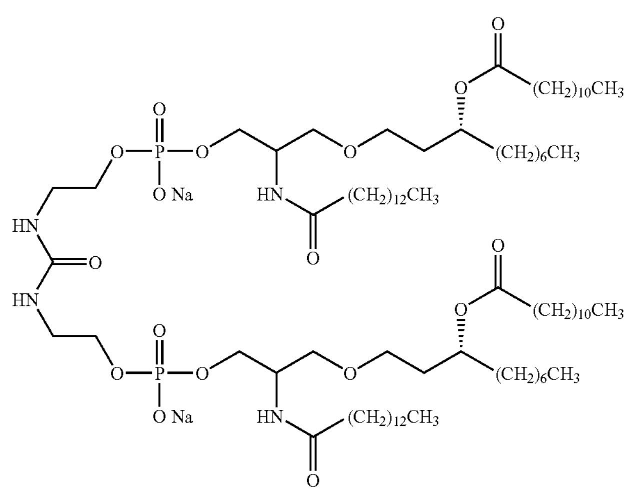 |

| No. | Structure |
|---|---|
| 119328 | 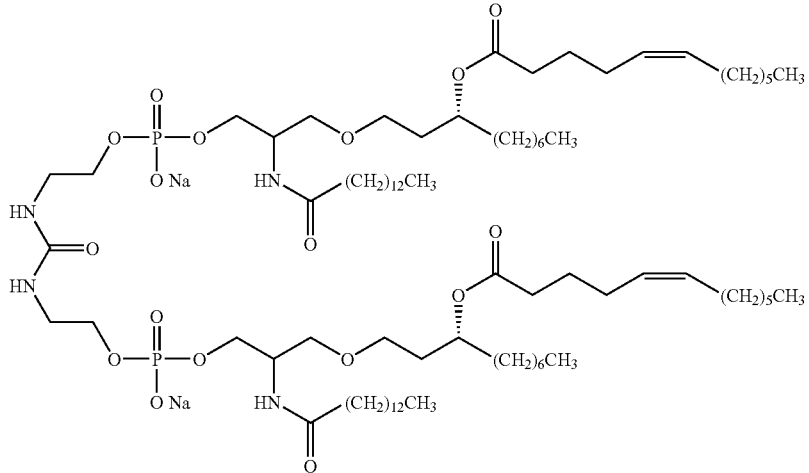 |
| 119329 | 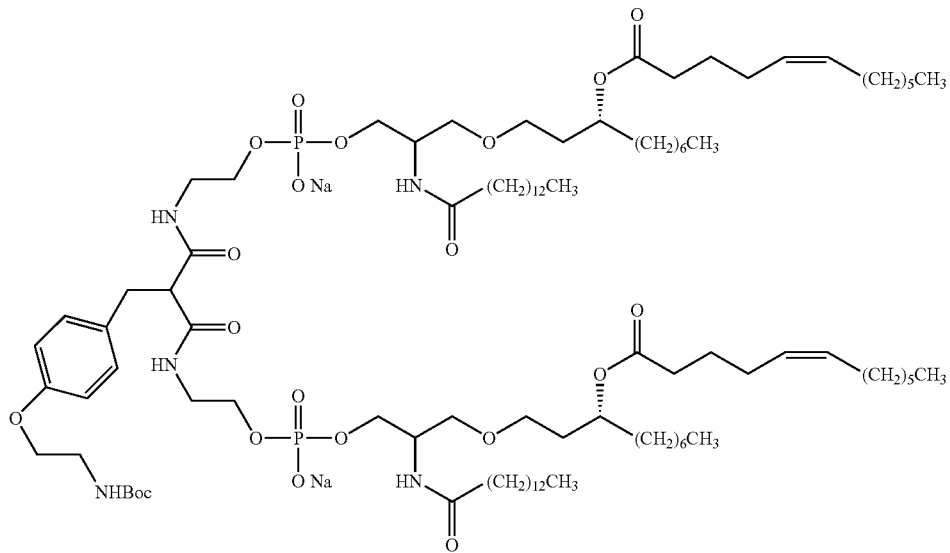 |
| 119521 | 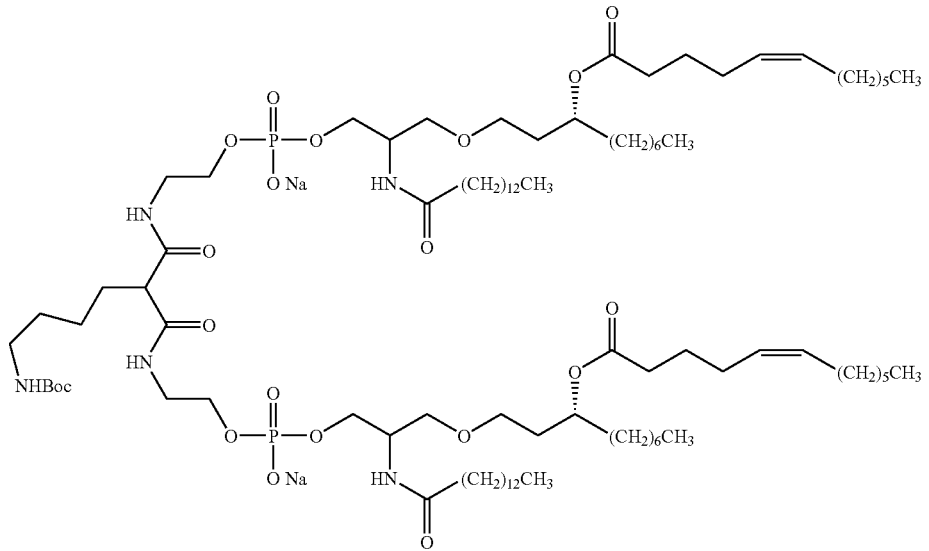 |

| No. | Structure |
|---|---|
| 119522 | 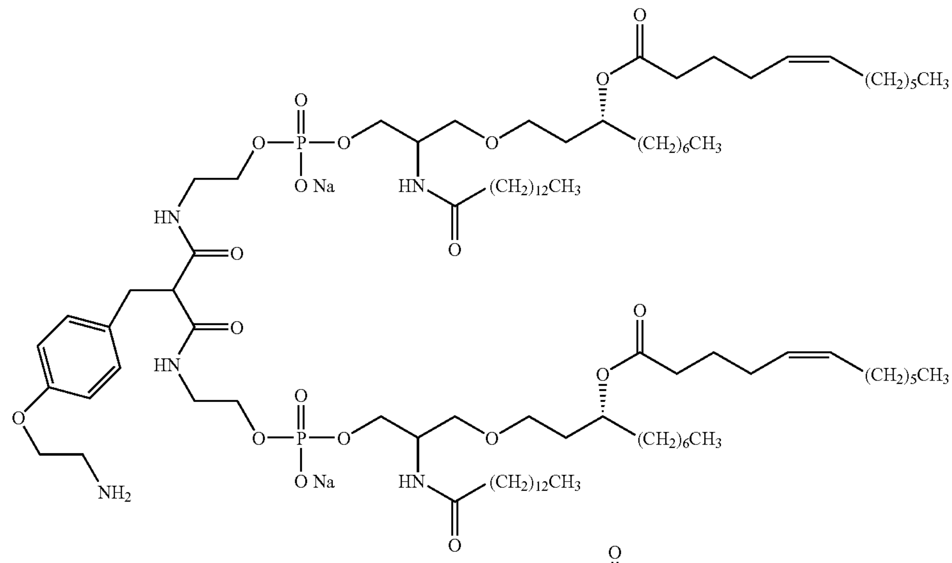 |
| 119523 | 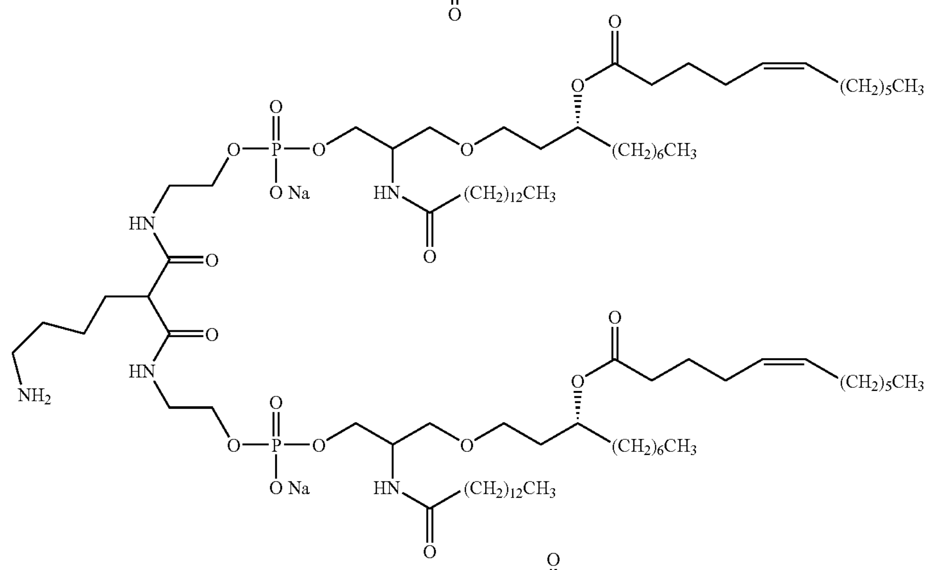 |
| 803028 | 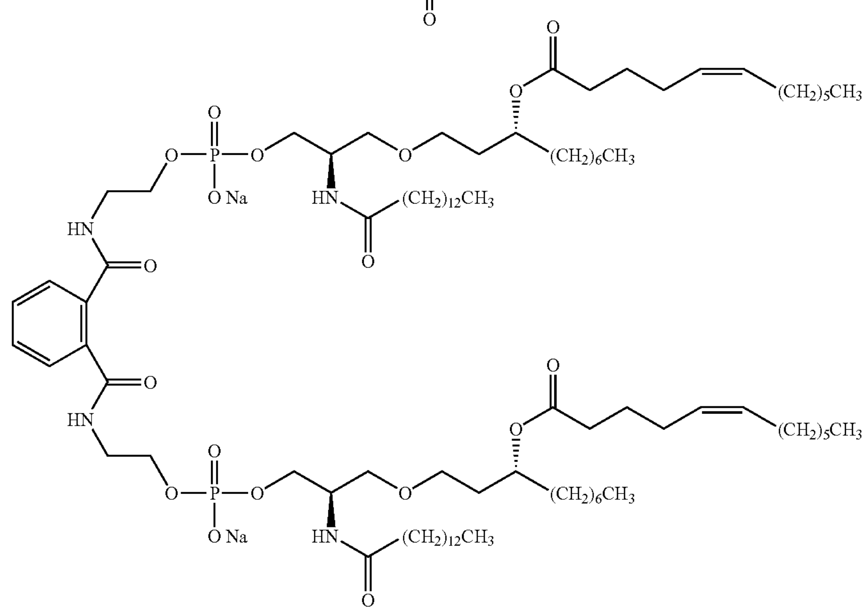 |

| No. | Structure |
|---|---|
| 803045 | 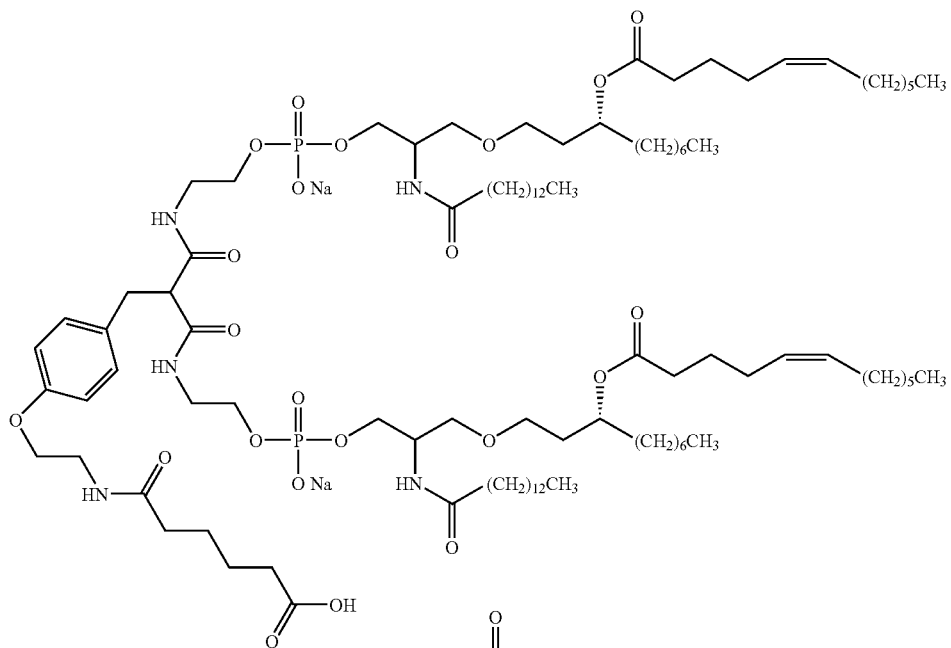 |
| 803056 | 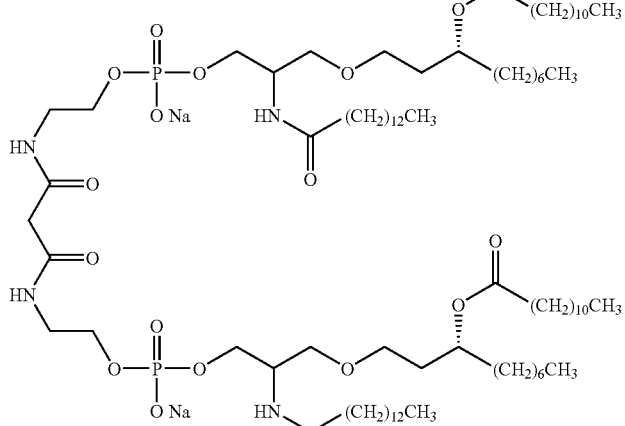 |
| 803059 | 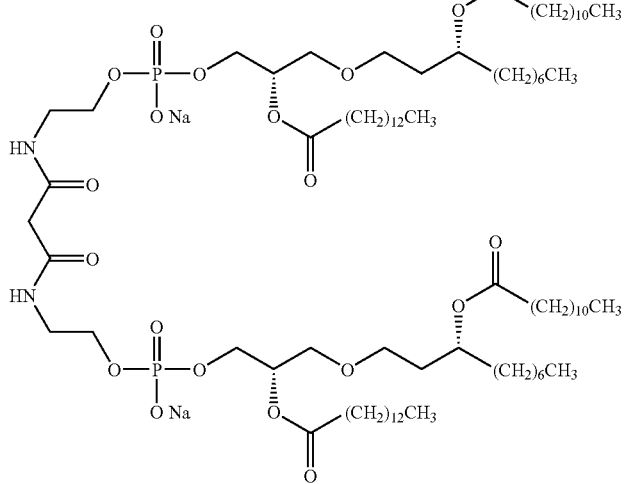 |

| No. | Structure |
|---|---|
| 803592 | 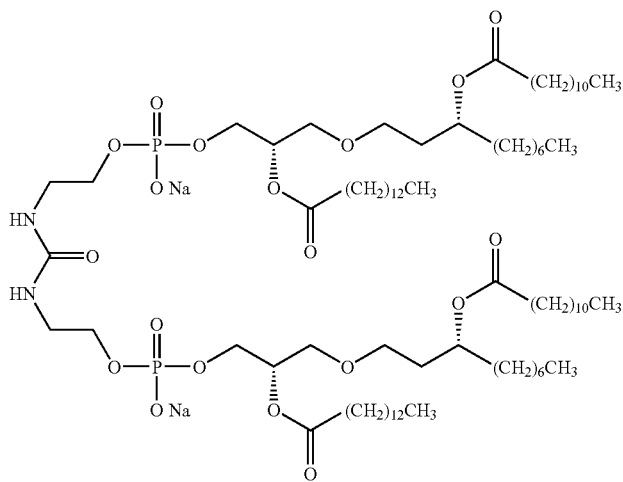 |
| 803596 | 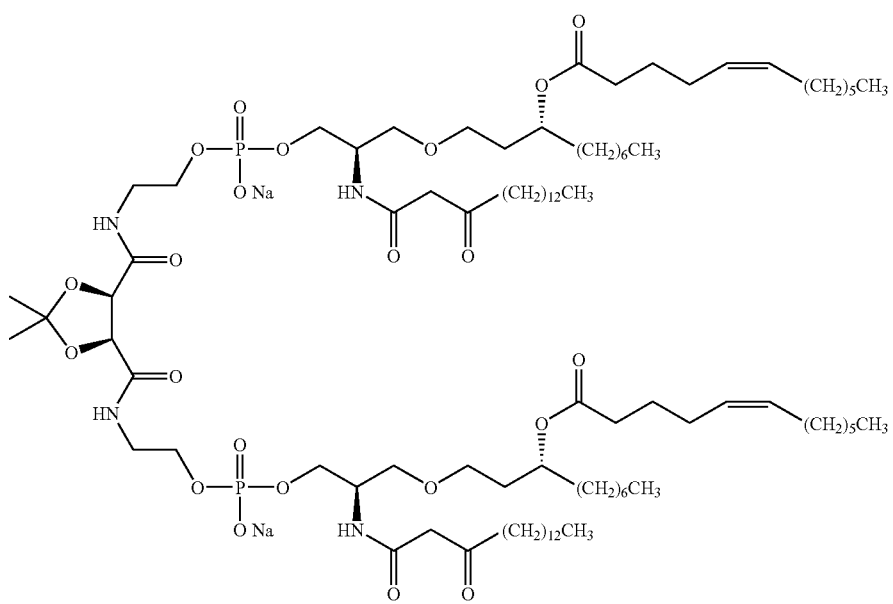 |
| 803597 | 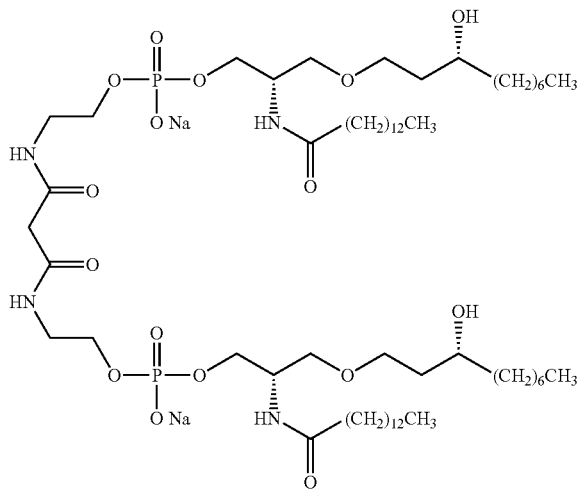 |

| No. | Structure |
|---|---|
| 803598 | 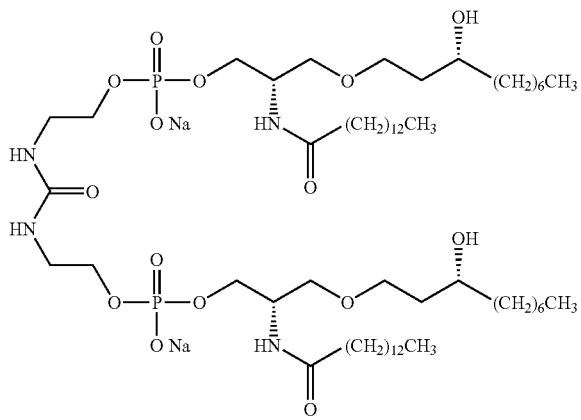 |
| 803599 | 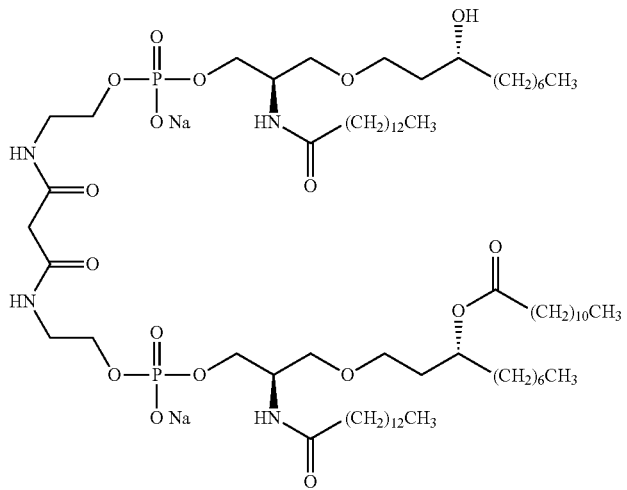 |
| 803613 | 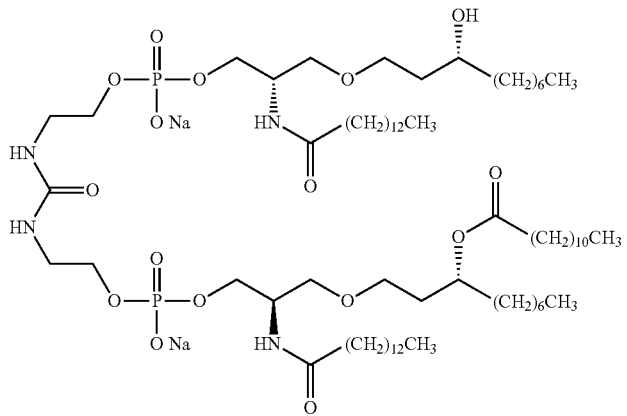 |

| No. | Structure |
|---|---|
| 803731 | 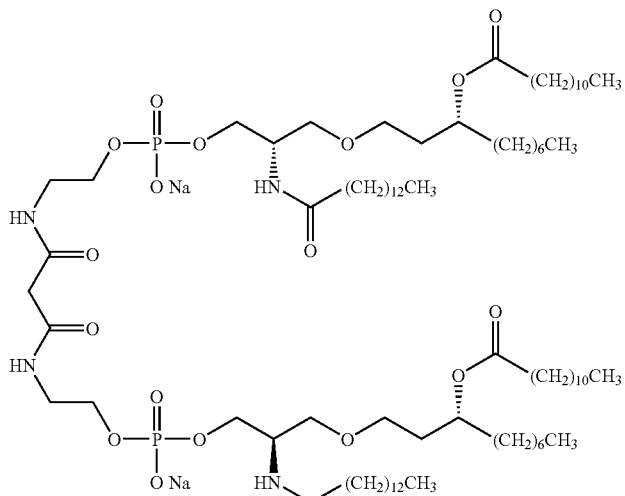 |
| 803733 | 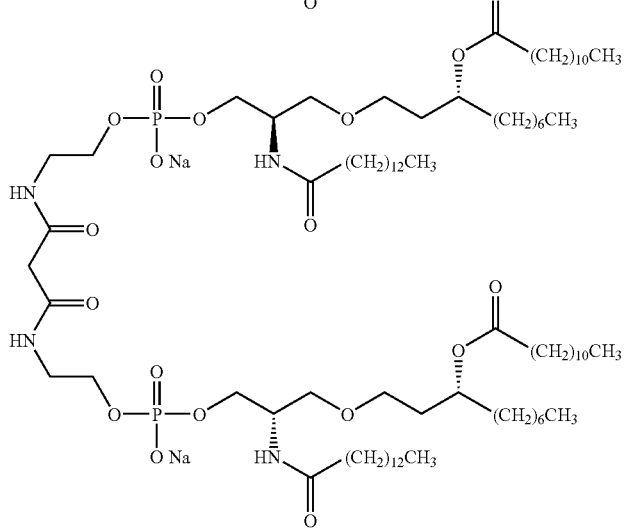 |
| 803751 | 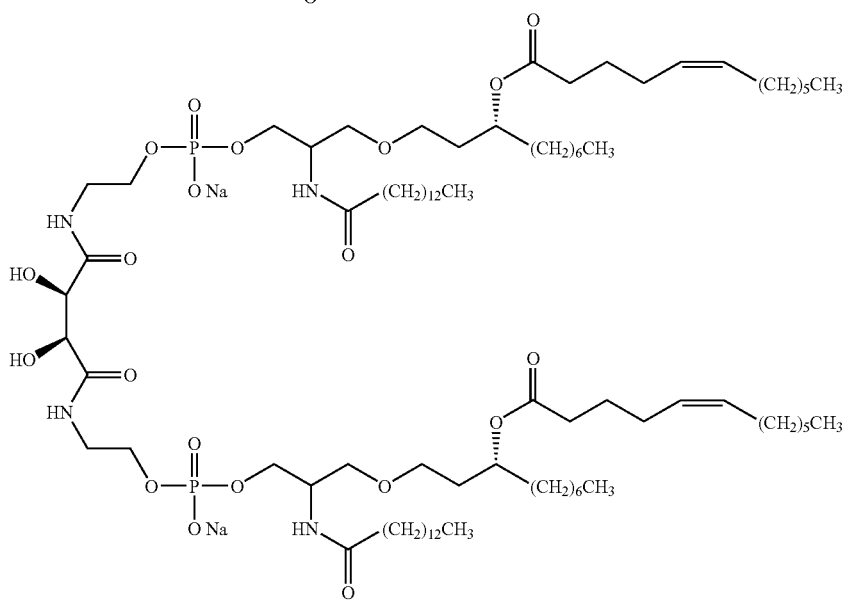 |

| No. | Structure |
|---|---|
| 803783 | 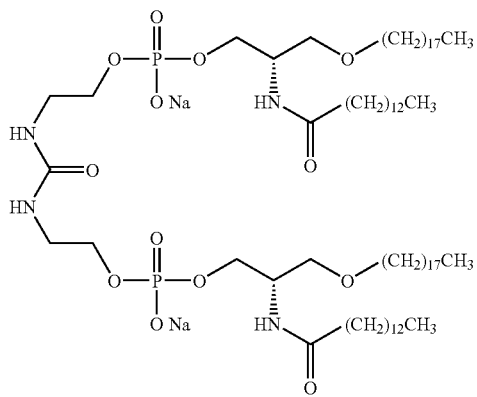 |
| 803784 | 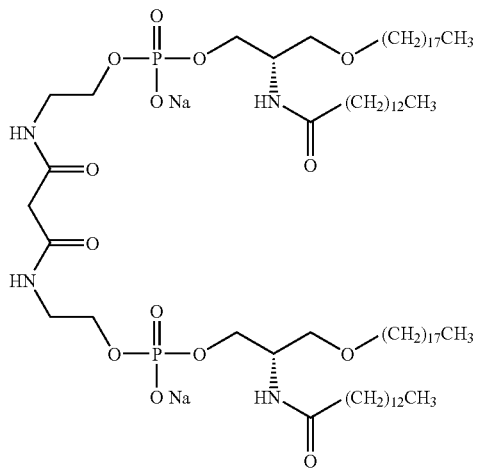 |
| 803789 | 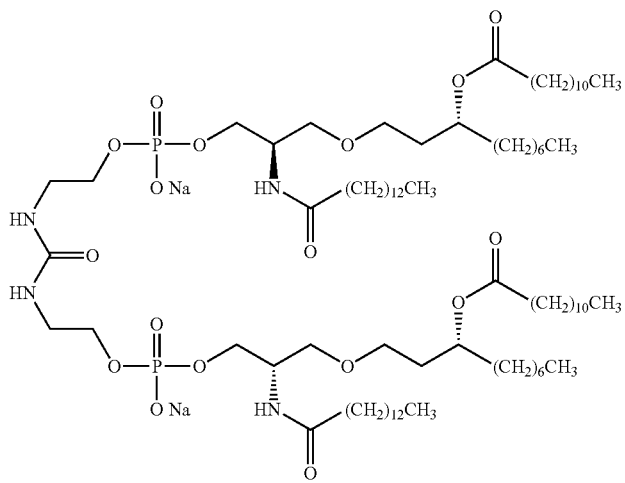 |

| No. | Structure |
|---|---|
| 804061 | 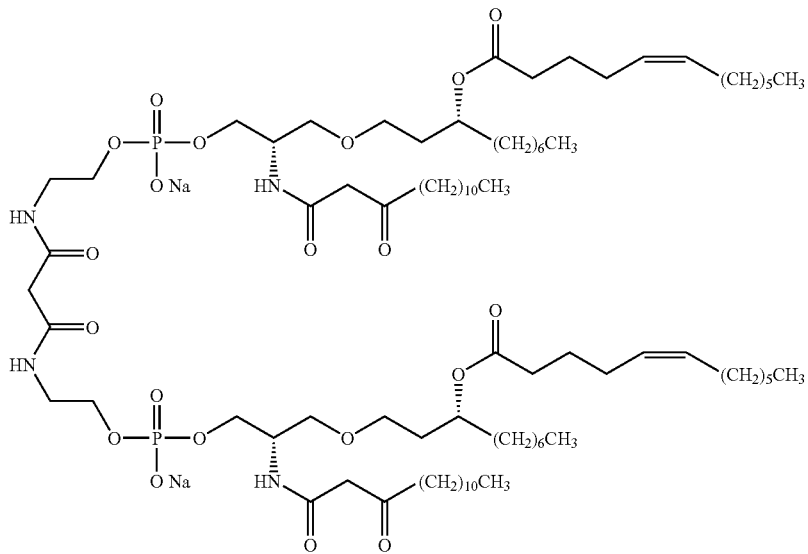 |
| 804097 | 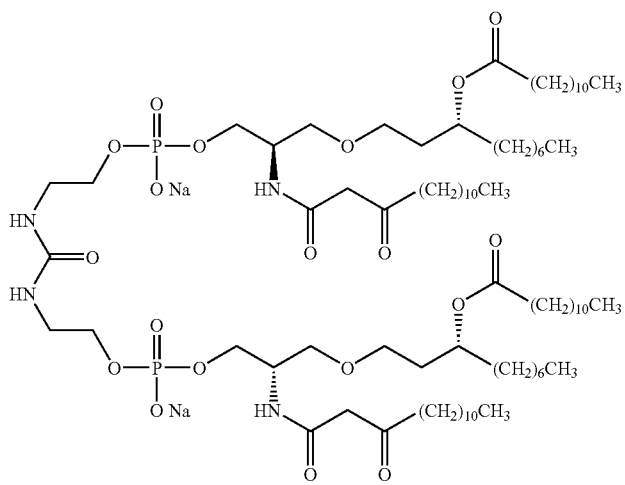 |
| 804121 | 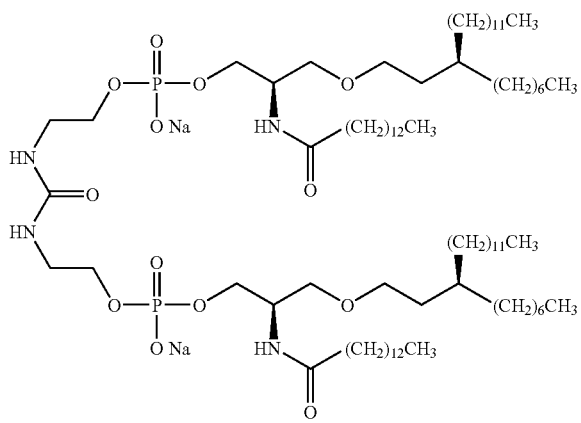 |

| No. | Structure |
|---|---|
| 804130 | 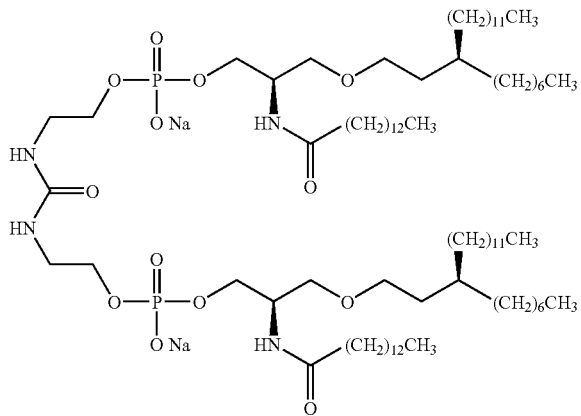 |
| 804221 | 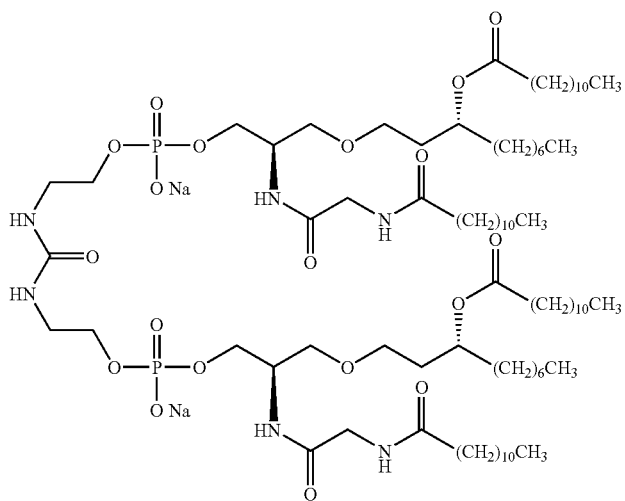 |
| 804222 | 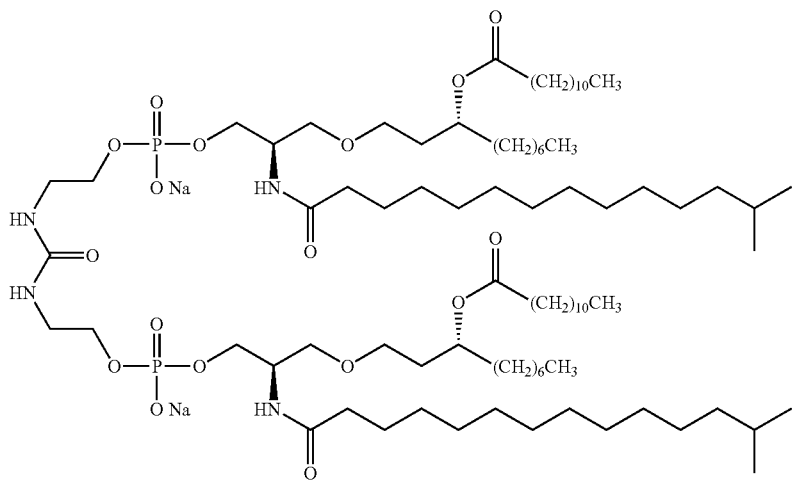 |

| No. | Structure |
|---|---|
| 804252 | 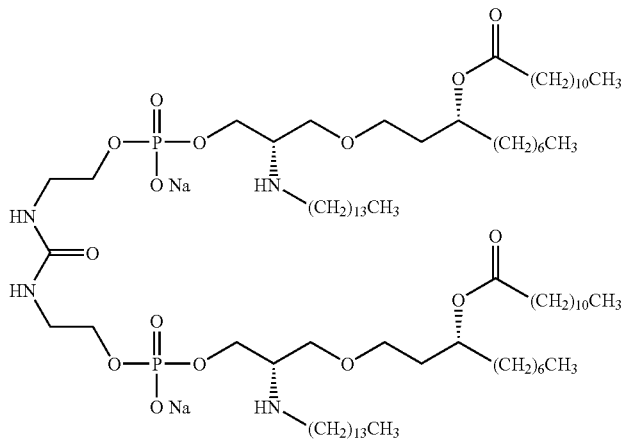 |
| 804253 | 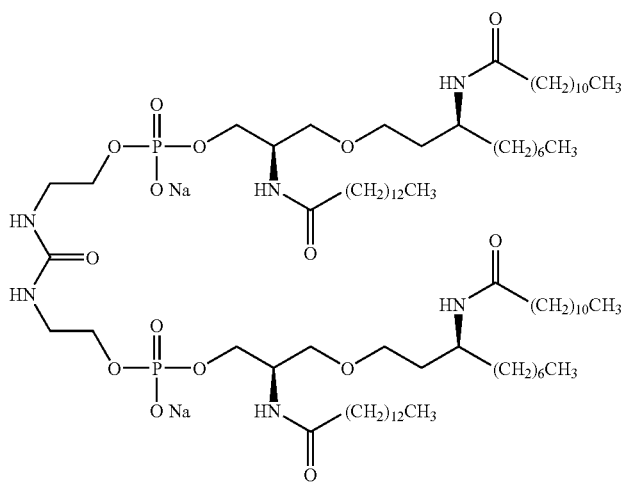 |
| 804281 | 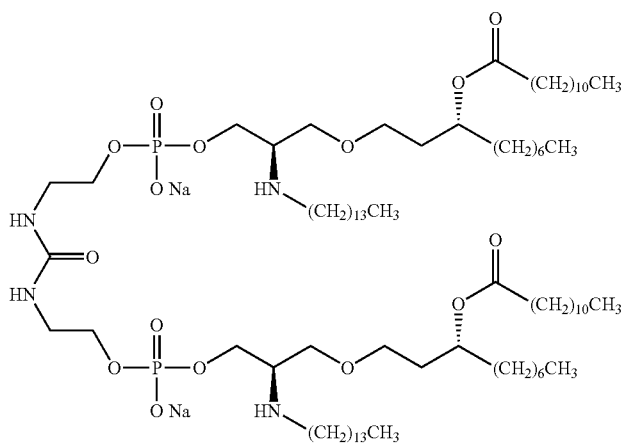 |

| No. | Structure |
|---|---|
| 804313 | 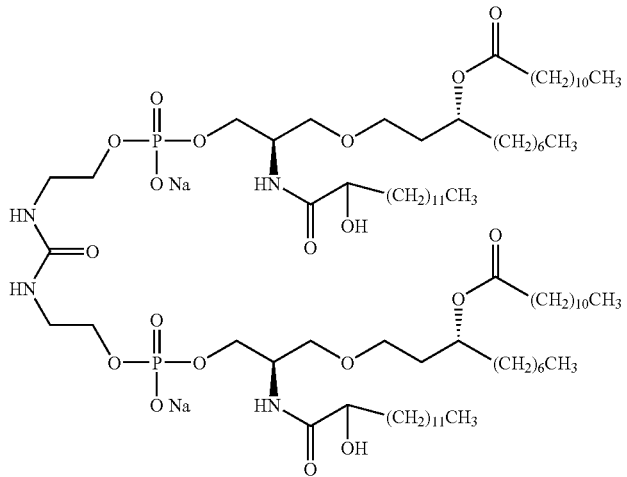 |
| 804339 | 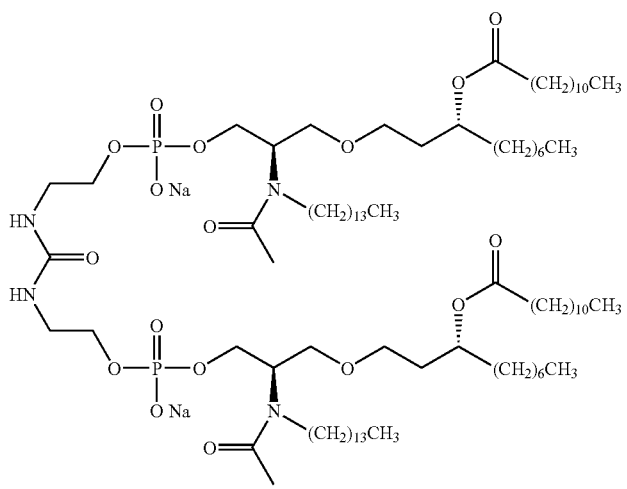 |
| 804372 | 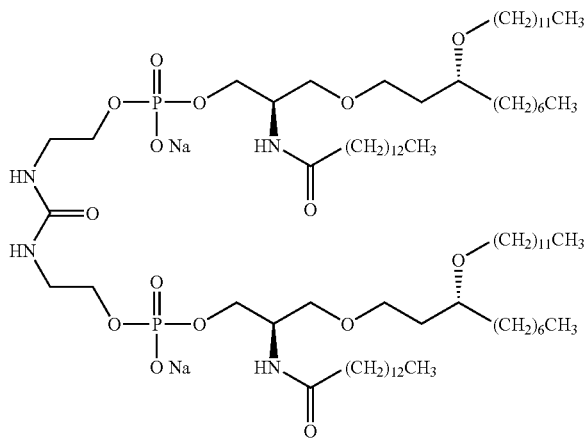 |

-continued
| No. | Structure |
|---|---|
| 804503 | 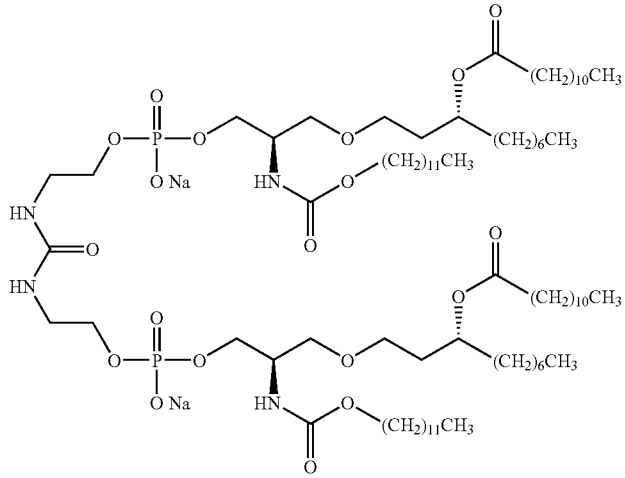 |
| 804558 | 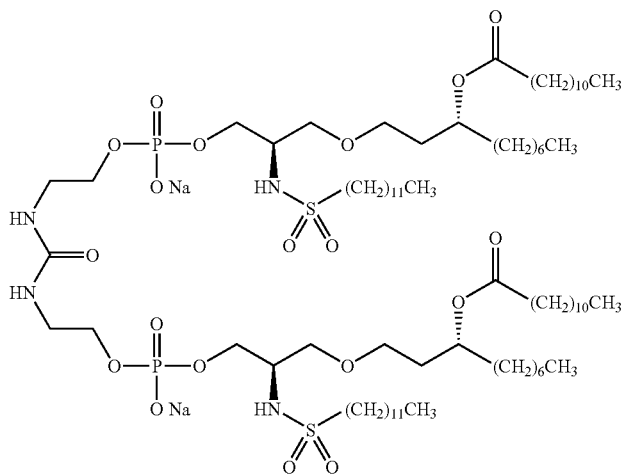 |
| 804596 | 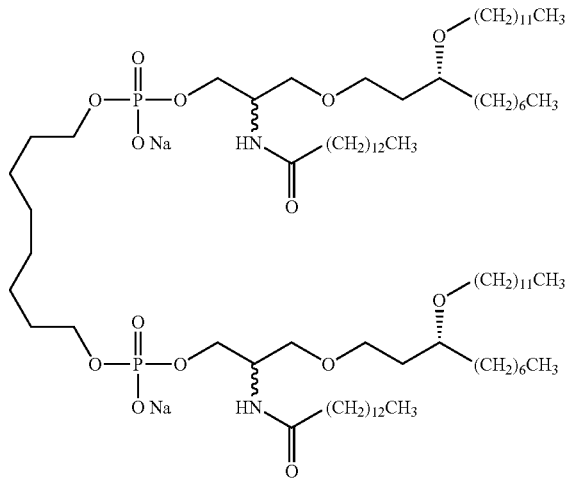 |

| No. | Structure |
|---|---|
| 804674 | 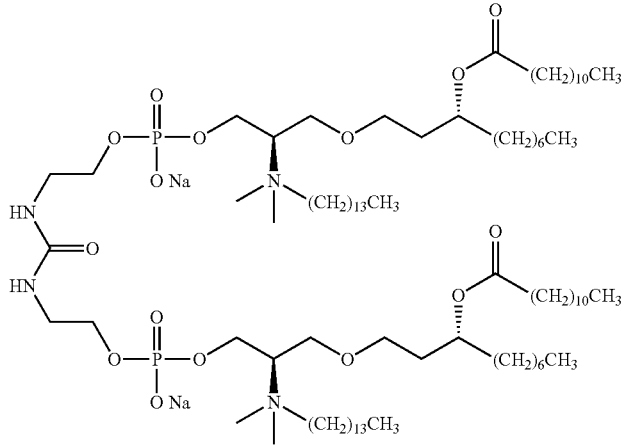 |
| 804678 | 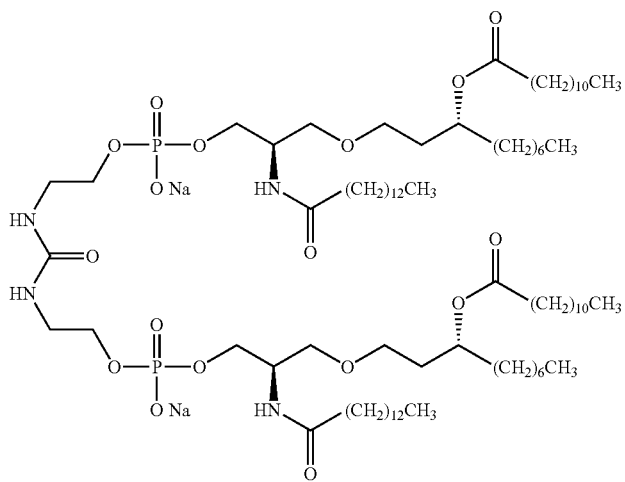 |
| 804679 | 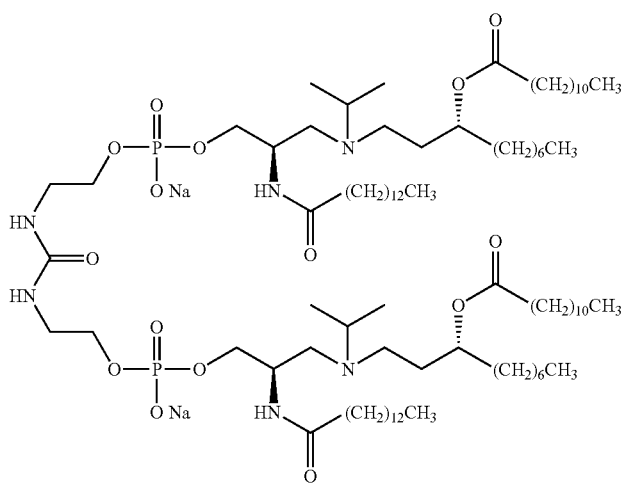 |

| No. | Structure |
|---|---|
| 804732 | 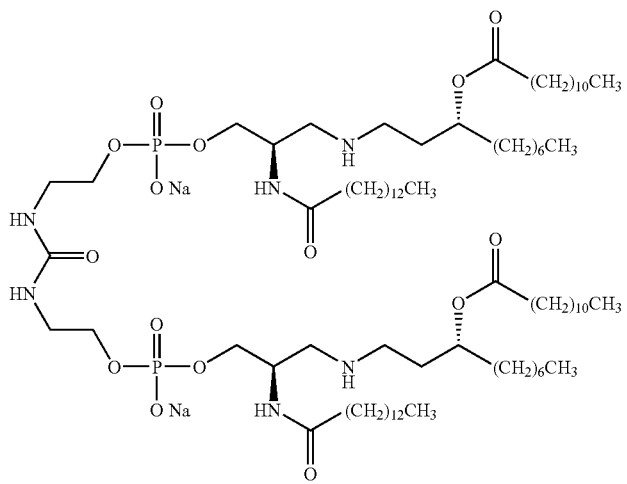 |
| 804772 | 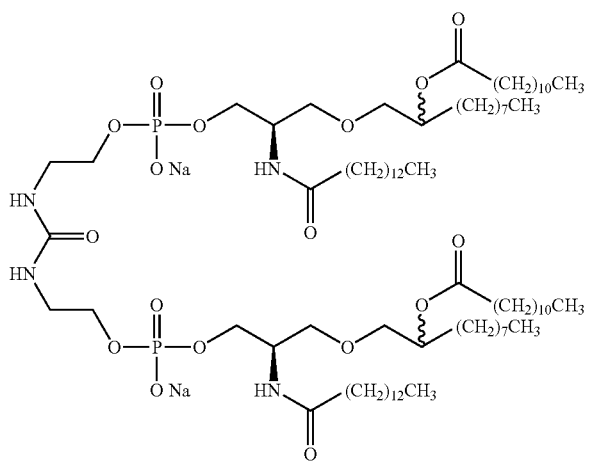 |
| 804947 | 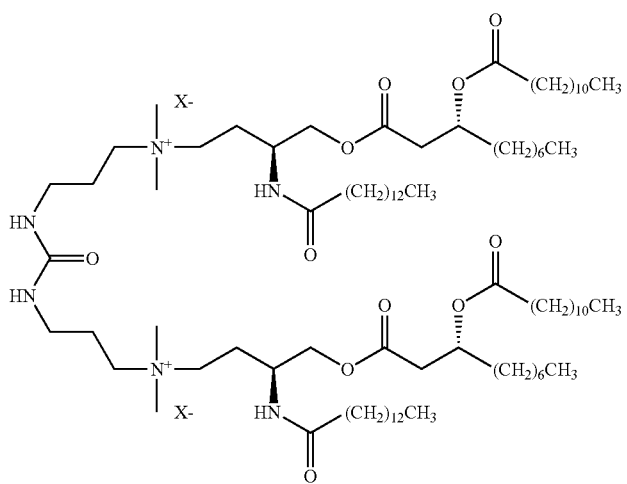 |

| No. | Structure |
|---|---|
| 804638 | 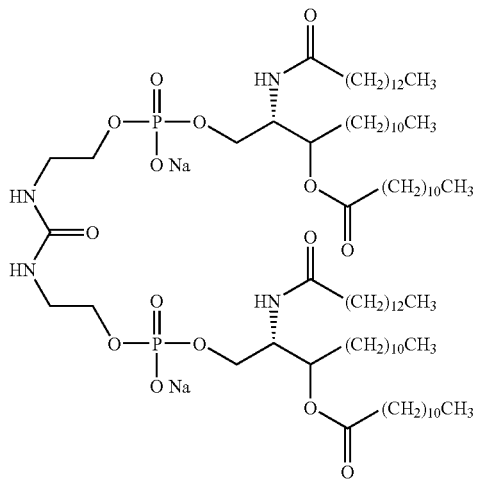 |
| 804666 | 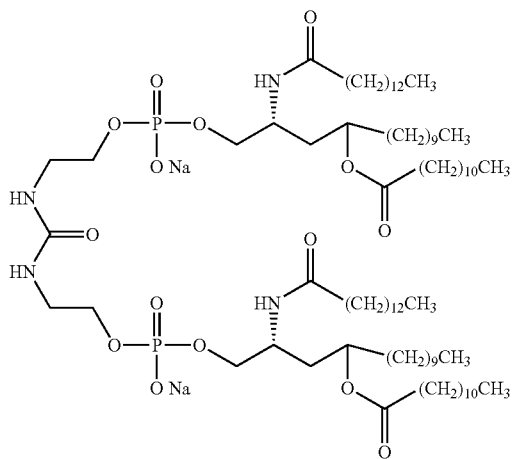 |
| 804874 | 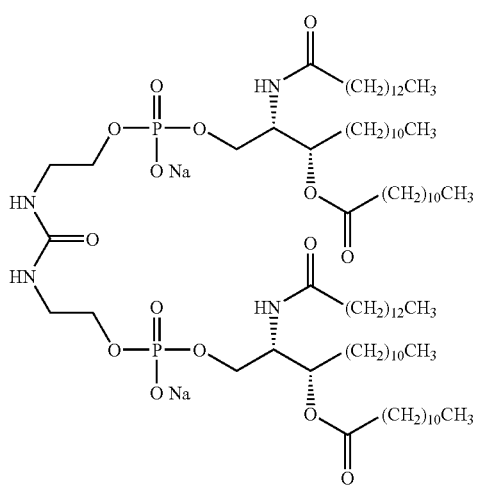 |

| No. | Structure |
|---|---|
| 805028 | 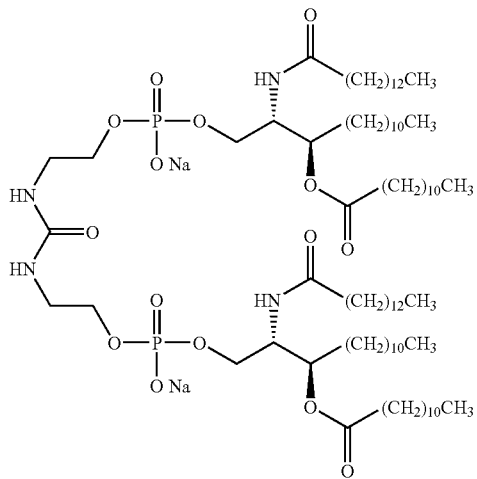 |
| 805520 Isomer A | 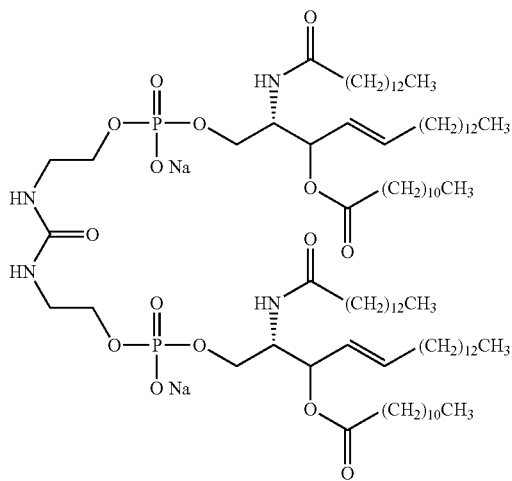 |
| 805270 Isomer B | 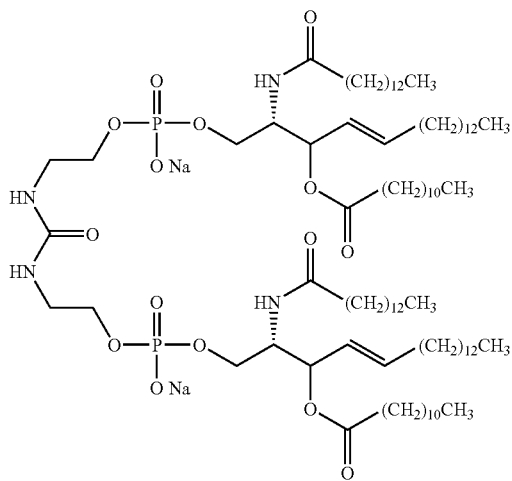 |

| No. | Structure |
|---|---|
| 805271 | 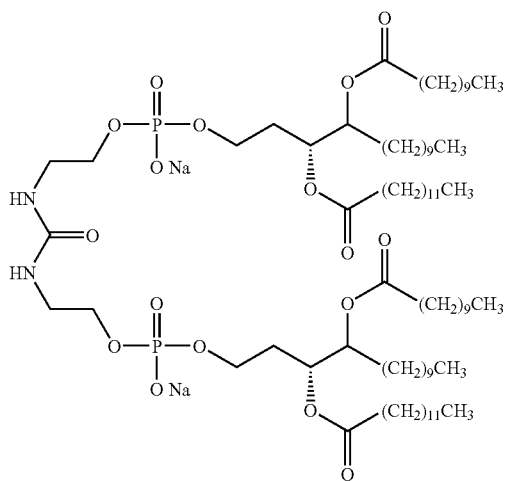 |
| 805274 | 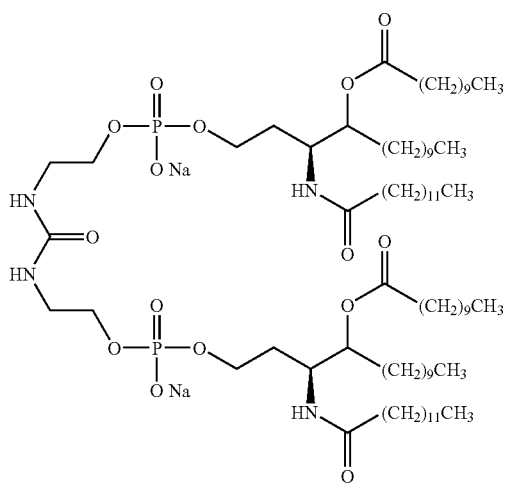 |
| 805328 | 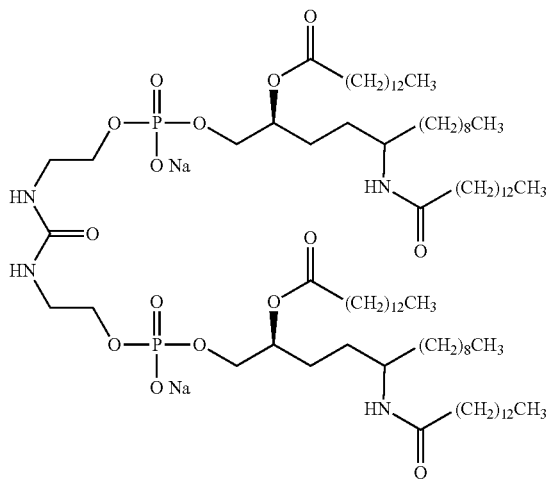 |

| No. | Structure |
|---|---|
| 805329 | 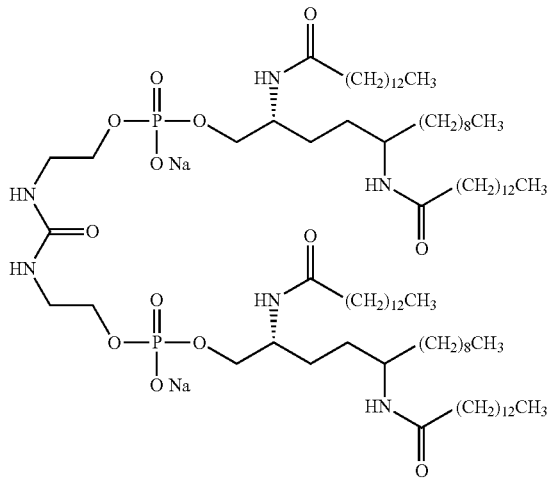 |
| 805517 | 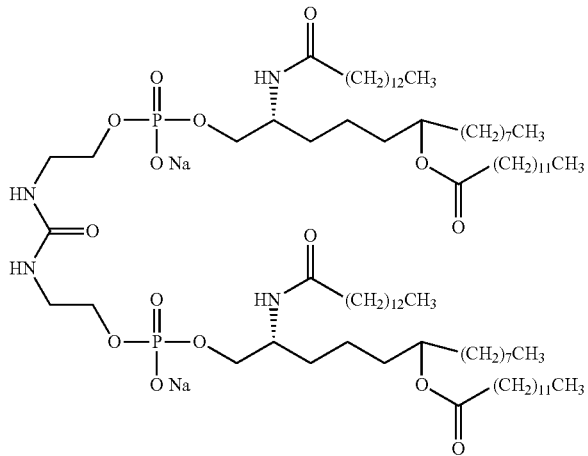 |
| 805518 Isomer A | 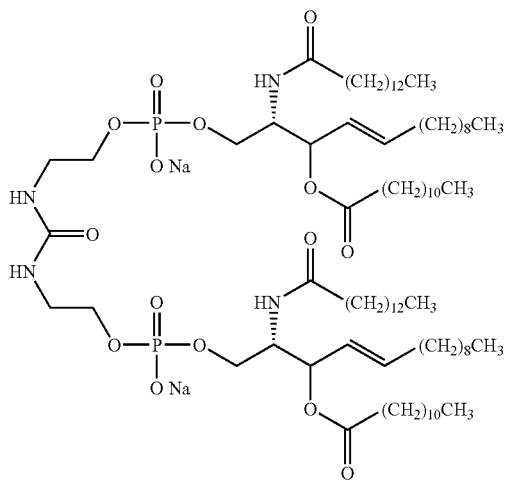 |

| No. | Structure |
|---|---|
| 805519 Isomer B | (chemical structure) |

BIOLOGICAL EXAMPLES

Example 1

Induction of Cytokines (In Vitro)

A. Assays in Human Whole Blood

The most readily available human system to test compound activity on monocytes/macrophages is in whole blood. Various concentrations of compounds of the invention were added as 10× stocks in 50 µl of $Ca^{++}$, $Mg^{++}$-free Hank's balanced salt solution (HBSS) followed by 50 µl of HBSS into 400 µl of heparinized whole blood obtained from normal volunteers (18-51 years old; 110-230 lb.) into the wells of plastic assay plates, for a total volume of 500 µl/well (final concentration of whole blood was 80%). After a 3-hour incubation with gentle shaking at 37° C. in a 5% $CO_2$ atmosphere, the assay plates were centrifuged at 1000×g for 10 min. at 4° C. and plasma was drawn off and frozen at −80° C. Plasma samples were analyzed for TNF-alpha, IL-10, and IL-12 by ELISA (Genzyme Corp., Cambridge, Mass.). Each assay point was tested in triplicate.

As shown in FIG. 1, compounds such as 100, 184 and 186 stimulate blood-borne cells to release TNF-alpha. This stimulatory activity can be compared to that of 10 ng/ml endotoxin (or LPS) present in similar incubations in the same assay. As shown in Table 1, activity of compounds (tested at 10 µM) ranges from inactive (such as compound 110) to compounds demonstrating greater activity than the LPS standard.

Figure 2:
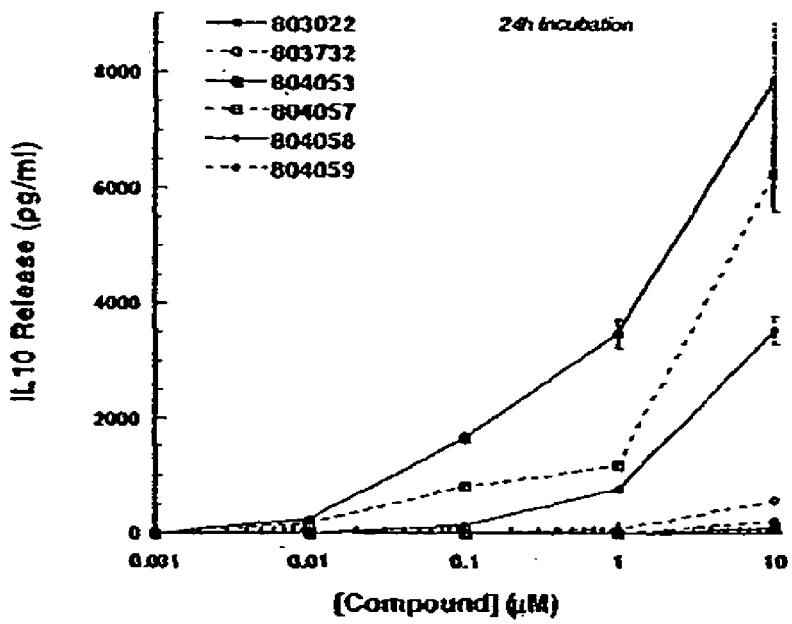
FIG. 2 is a graph that shows the results of an in vitro assay for induction of IL-10 and IL-12 release by compounds ER803022, ER803702, ER804053, ER804057, ER804058, and ER804059.
Figure 2:
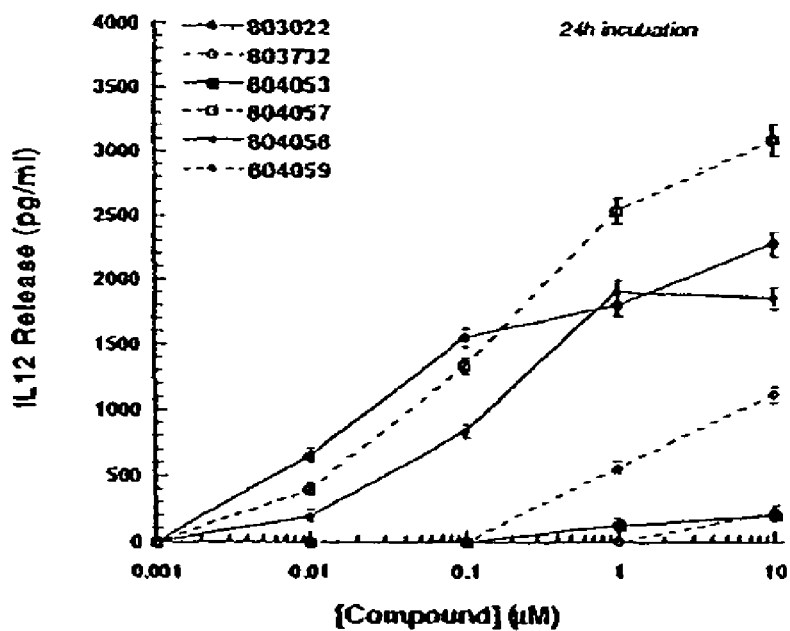

As shown in FIG. 2, compounds such as 803022, 804057, and 804058 stimulate blood-borne cells to release IL-10. Compounds 803022, 804057, 804058, and 804059 stimulate blood-borne cells to release IL-12.

As shown in Table 2, a variety of cytokines are secreted by nonadherent and adherent peripheral blood mononuclear cells (PBMC) when treated with compound 804057, including IL1-α, IL-1β, IL-6, IL-10, IL-12, Interferon-α, Interferon-γ, GM-CSF, and TNFα.

B. Cultured Human Cell Lines

Similar results can be obtained when compounds of the invention are tested in a cell-culture model. In this assay, compounds of the invention are tested for their ability to stimulate secretion of alkaline phosphatase from THP-1 cells that have been transfected with the gene for secreted alkaline phosphatase under the control of the TNF-alpha promoter, as described in detail in Goto et al., Molecular Pharmacology 49; 860-873 (1996). In this assay, however, the effects of removing serum[1]—a condition that may more-likely mimic a subcutaneous environment—can be evaluated. As shown in FIG. 2 and described in Table 1, results from these assays indicate that compounds of the invention stimulate induction of genes under the control of the TNF-alpha promoter when added to cells in the absence as well as the presence of serum.

---

[1] This is important to determine if serum components such as lipopolysaccharide binding protein are necessary for drug activity.

TABLE 1
| | | THP-1 cell Stimulation (% of compound 100 at 10 μM)[1] | |
|---|---|---|---|
| ER Compound Number | Whole Blood (% of LPS at 10 μM) | +serum | −serum |
| MPL Standard | 29[2] | | |
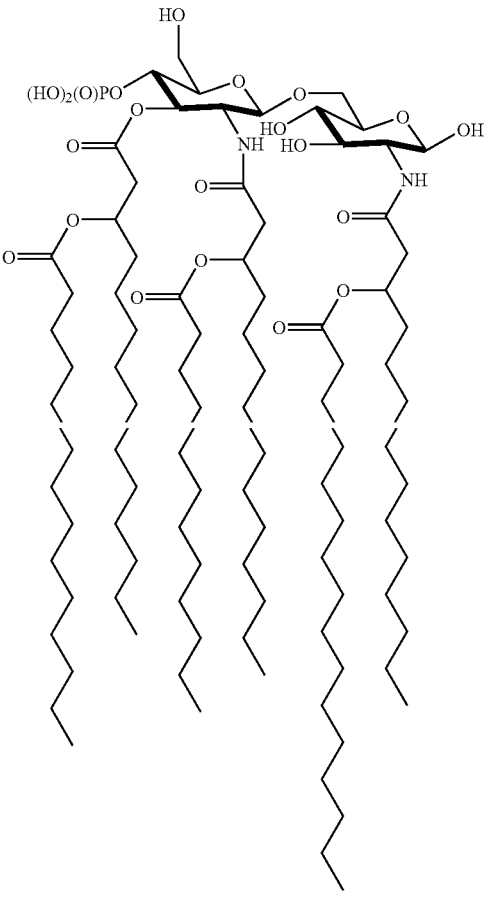
| | | | |
|---|---|---|---|
| 112022 | 131 ± 10.2 (n = 6) | | |
| 111230 | | 49 | |
| 111231 | | 17 | |
| 111232 | 158 | 155 | 225 |
| 111233 | | 141 | |
| 112043 | 0 | | |
| 112044 | 0 | | |
| 112047 | 0 | | |
| 112048 | 0 | 34 | |
| 112049 | 0 | | |
| 112063 | 0 | | |
| 112064 | | 50 | |
| 112065 | | 86 | |
| 112066 | 162 | 330 | |
| 112071 | 0 | | |
| 112072 | 0 | | |
| 112091 | 0 | | |
| 112092 | 0 | | |
| 112093 | 0 | | |
| 112098 | 0 | | |
| 112049 | 0 | | |
| 112100 | 0 | | |

TABLE 1-continued

Stimulation of cytokine release by compounds in vitro

| ER Compound Number | Whole Blood (% of LPS at 10 µM) | THP-1 cell Stimulation (% of compound 100 at 10 µM)[1] | |
|---|---|---|---|
| | | +serum | −serum |
| 112859 | 0 | | |
| 112860 | 0 | | |
| 112861 | 0 | | |
| 113634 | 0 | | |
| 113635 | 0 | | |
| 113643 | 0 | | |
| 113644 | 0 | | |
| 113651 | 133 ± 4.4 (n = 4) | 215 | 254 |
| 113665 | | | |
| 113666 | | | |
| 118023 | 63 | | |
| 019772 | 69 | | |
| 118989 | 159 | | |
| 118999 | 105 | | |
| 119000 | 60 | | |
| 119001 | 113 | | |
| 118949 | 138 | | |
| 119327 | 165 ± 33 (n = 3) | | |
| 119328 | 181 ± 42 (n = 3) | | |
| 119329 | 2 ± 2 (n = 2) | | |
| 119521 | 103 | | |
| 119522 | 129 | | |
| 119523 | 176 | | |
| 803022 | 164 | | |
| 803045 | 65 | | |
| 803056 | 151 ± 42 | | |
| 803058 | 149 ± 37 (n = 2) | | |
| 803059 | 2 | | |
| 803592 | 15 | | |

[1]Response in each assay was compared to 10 µM compound 100 internal standard which typically induced 2-3 fold increase in TNF-alpha PLAP expression over basal.
[2]Tested at @ 5.8 µM.

TABLE 2

Cytokines Resulting from Stimulation of Human PBMC by ER804057

| Cytokine | Cell population | Length of Stimulation (hrs) | Cytokine Production (pg/mL) | |
|---|---|---|---|---|
| | | | Medium | ER804057 (50 nM) |
| IL-1α | Nonadherent PBMC | 24 hrs | 4 | 108 |
| | Adherent PBMC | 4 hrs | 0 | 8 |
| IL-1β | Nonadherent PBMC | 24 hrs | 4 | 431 |
| | Adherent PBMC | 4 hrs | 0 | 55 |
| IL-6 | Adherent PBMC | 4 hrs | <2 | 551 |
| IL-10 | Adherent PBMC | 24 hrs | 17 | 175 |
| IL-12p70 | Whole blood | 24 hrs | 0 | 1332 |
| Interferon-α | Adherent PBMC | 4 hrs | 61 | 345 |
| | Adherent PBMC | 48 hrs | 5 | 175 |
| Interferon-γ | Nonadherent PBMC | 24 hrs | 4 | 331 |
| GM-CSF | Nonadherent PBMC | 24 hrs | 14 | 353 |
| TNF-α | Adherent PBMC | 4 hrs | 7 | 3627 |

C. Murine Splenocytes

The ability of compounds to stimulate cytokine release from splenocytes can be assessed in a mouse model. Spleen cells harvested from C57BL6 mice are cultured for 24 hours in RPMI 1640 cell culture medium containing 5% FBS, 1 mM sodium pyruvate, 2 mM L-glutamine, 100 U/ml penicillin/streptomycin and 50 µM beta-mercaptoethanol, various concentrations of test compound for 20-24 hours, after which the cell culture supernatant is tested for the presence of cytokines.

Figure 3:
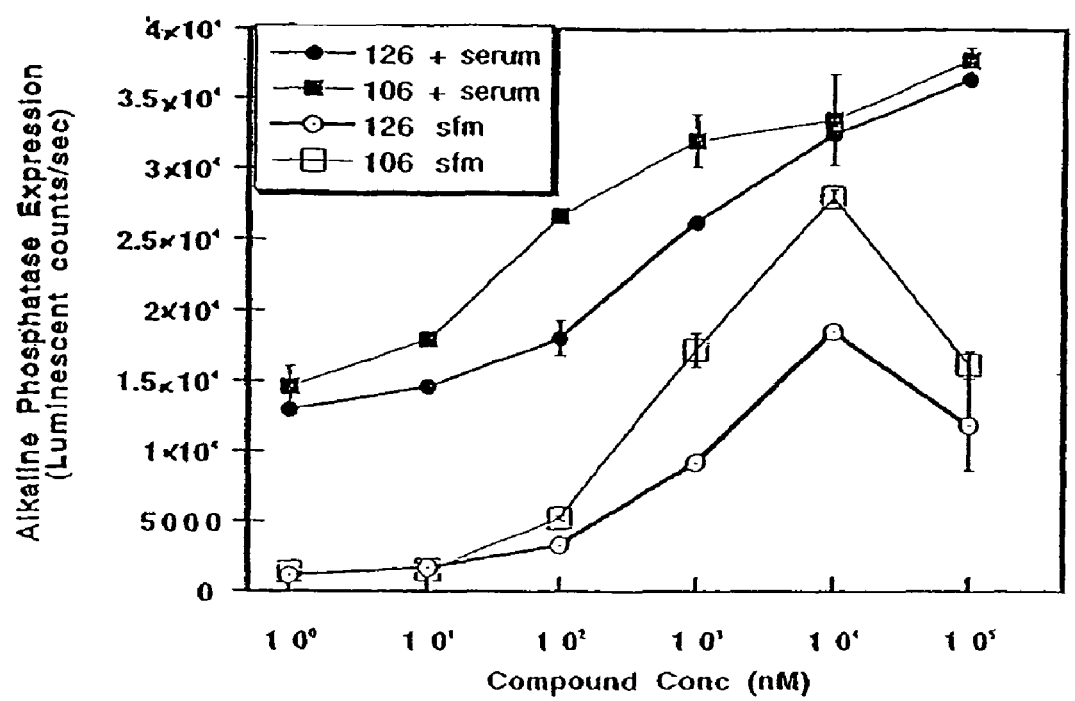
FIG. 3 is a graph that shows stimulation of alkaline phosphatase expression from an inducible reporter construct with the TNF promoter (TNF-PLAP) in THP-1 cells by compounds 106 and 126 in the absence and presence of 10% serum.
Figure 4:
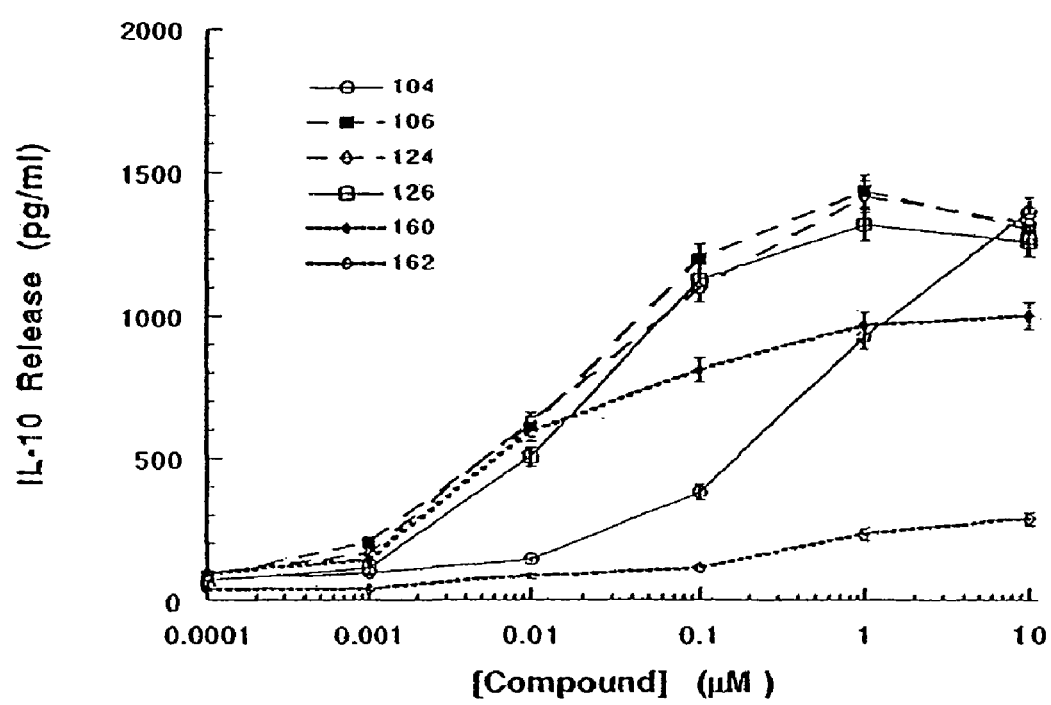
FIG. 4 is a graph showing stimulation of IL-10 release from normal mouse splenocytes by compounds 104, 106, 124, 126, 160, and 162 of the invention.
Figure 5:
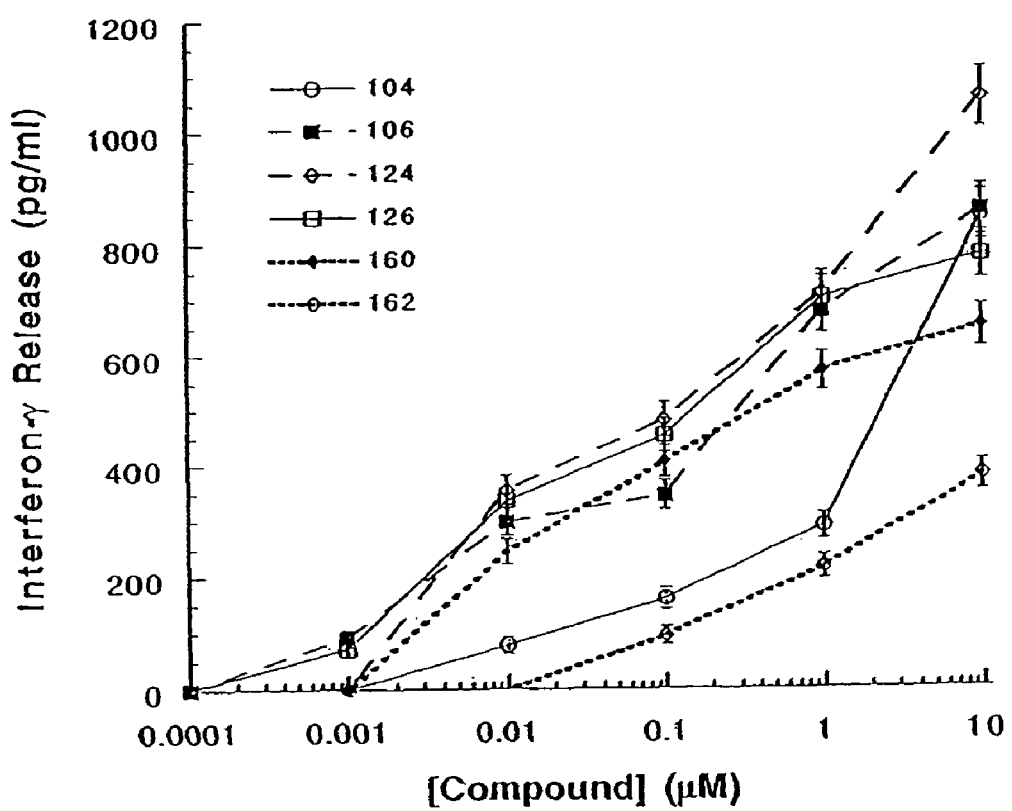
FIG. 5 is a graph showing stimulation of interferon-gamma release from normal mouse splenocytes by compounds 104, 106, 124, 126, 160, and 162 of the invention.

Spleen cells harvested from mice were cultured for 24 house with test compound and the supernatant was tested for release of cytokines. As shown in FIGS. 3 and 4, the release of cytokines such as IL-10 and interferon-gamma from splenocytes is stimulated by compounds such as 104, 106, 124, 160, and 162.

These assays utilized a heterogeneous population of cells derived from the spleen. This makes it possible that cytokine induction can be caused both by direct effects of test compounds on cells and through more indirect stimulation of cytokine "cascades" where the release of a cytokine by one type of cell can induce release of other cytokines in other cells present in the same media. It is possible that this cytokine "milieu" is responsible for part of this robust immune responses.

D. Tolerization to TLR Family Ligands

Figure 6:
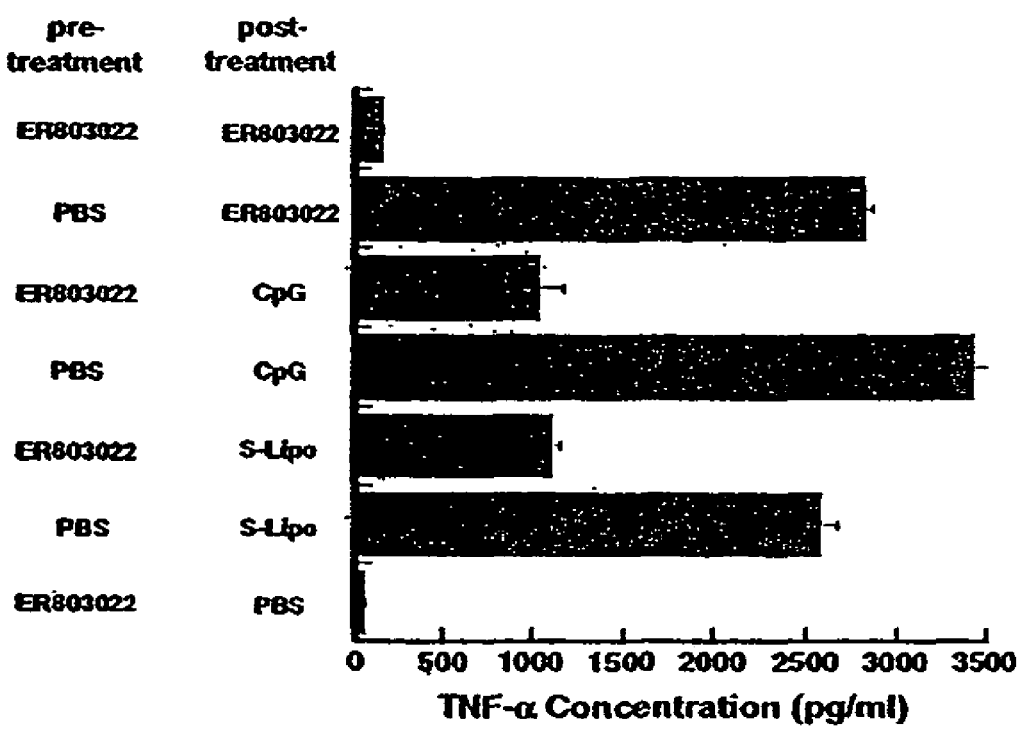
FIG. 6 is a graph showing stimulation of TNF-alpha release in response to TLR2, TLR4, and TLR9 ligands by untreated mouse macrophage cells and mouse macrophage cells pretreated with the immunomodulatory compound ER803022.

Preliminary experiments were carried out to determine dosage ranges for the different ligands so as to assay for comparable levels of secreted TNFα. Cells of the mouse macrophage line RAW 264.7 were plated in RPMI 1640 complete culture medium (10% fetal bovine serum, 1 mM sodium pyruvate, 2 mM L-glutamine, 100 U/mL penicillin/streptomycin and 50 µM β-mercaptoethanol). Cells were treated for 24 hours with the TLR4 ligand ER-803022 at 0.1 µg/mL by addition of a concentrated stock solution. Negative control cells were treated with an equivalent volume of PBS. After 24 hours, cells were washed twice in RPMI 1640 complete medium and incubated in medium alone for 3 hours. Cultures were then restimulated with the following synthetic TLR ligands: lipopeptide (S-lipo, a ligand for TLR2) at 0.1 µg/mL, ER-803022 at 0.1 µg/mL, a mouse CpG oligonucleotide of the sequence TCCATGACGTTCCTGATGCT (a ligand of murine TLR9) at 0.5 µg/mL, or PBS. Supernatants were taken at 3 and 4 hours and cytokine levels were determined by ELISA. As shown in FIG. 6, mouse macrophage cells that were treated with an initial exposure to the immunomodulatory compound ER803022 released less TNF-alpha upon subsequent exposure to ER803022 compared to those that were not pretreated. In addition, cells that were pretreated with ER803022 displayed diminished release of TNF-alpha in response to exposure to the TLR2 ligand S-lipoprotein, and in response to the CpG oligonucleotide, a TLR9 ligand.

TABLE 3

WB $ED_{50}$ vs. % of LPS at 10 ng/ml

| ER# | WB $ED_{50}$ vs LPS@ 10 ng/ml |
|---|---|
| MPL Standard | >>10 µm |
| 112022 | 0.696 µm |
| 111230 | |
| 111231 | 0.29 µm |
| 111232 | |
| 111233 | |
| 112043 | |
| 112044 | |
| 112047 | |
| 112048 | >>10 µM |
| 112049 | |
| 112063 | |
| 112064 | |
| 112065 | 0.25 µM |
| 112066 | 0.04 µM |
| 112071 | |
| 112072 | |
| 112091 | |
| 112092 | |
| 112093 | |
| 112098 | |
| 112099 | |
| 112100 | |
| 112859 | |
| 112860 | |
| 112861 | |
| 113634 | |
| 113635 | |
| 113643 | |
| 113644 | |
| 113651 | 0.70 µM |
| 113665 | |
| 113666 | |
| 118023 | |
| 019772 | |
| 118989 | 0.1 µM |
| 118999 | |
| 119000 | |
| 119001 | 1.23 µM |
| 118949 | |
| 119327 | 0.015 µM |
| 119328 | >>10 µM |
| 119329 | |
| 119521 | |
| 119522 | |
| 119523 | |
| 803022 | 0.06 µM |
| 803028 | |
| 803045 | |
| 803056 | |
| 803058 | 0.022 µM |
| 803059 | 0.89 µM |
| 803592 | |
| 803596 | |
| 803597 | |
| 803598 | |
| 803599 | |

TABLE 3-continued

WB $ED_{50}$ vs. % of LPS at 10 ng/ml

| ER# | WB $ED_{50}$ vs LPS@ 10 ng/ml |
|---|---|
| 803613 | |
| 803731 | >10 µM |
| 803732 | 0.85 µM |
| 803733 | 0.70 µM |
| 803751 | |
| 803783 | |
| 803784 | |
| 803789 | 0.10 µM |
| 804053 | 1.34 µM |
| 804057 | 0.008 µM |
| 804058 | 0.03 µM |
| 804059 | >10 µM |
| 804061 | 2.5 µM |
| 804097 | 0.3 µM |
| 804121 | 0.46 µM |
| 804130 | 0.66 µM |
| 804221 | 2.2 µM |
| 804222 | 0.008 µM |
| 804252 | 400 nM (576-021) + EtOH |
| 804253 | >10 µM |
| 804281 | 0.45 µM |
| 804313 | 0.014 µM |
| 804339 | 1.06 µM |
| 804372 | 0.4 µM |
| 804442 | 0.007 µM |
| 804503 | 0.35 µM |
| 804558 | 0.16 µM |
| 804596 | >10 µM |
| 804674 | 1.2 µM |
| 804678 | 0.018 µM |
| 804679 | 0.53 µM |
| 804680 | 0.015 µM |
| 804732 | <0.001 µM |
| 804764 | 0.015 µM |
| 804772 | 0.008 µM |
| 804947 | >>10 µM |

Table 4 below contains the compound number as referenced herein to the corresponding ER number.

TABLE 4

Correspondence of Compound Nos. to ER Nos.

| Compound # | ER # |
|---|---|
| 16 | 112048 |
| 31 | 803058 |
| 48 | 803733 |
| 50 | 803022 |
| 62 | 803789 |
| 72 | 803592 |
| 100 | 112022 |
| 102 | 111230 |
| 104 | 111231 |
| 106 | 111232 |
| 108 | 111233 |
| 110 | 112043 |
| 112 | 112047 |
| 114 | 112047 |
| 116 | 112048 |
| 118 | 112049 |
| 120 | 112063 |
| 122 | 112064 |
| 124 | 112065 |
| 126 | 112066 |
| 128 | 112071 |
| 130 | 112072 |
| 132 | 112091 |
| 134 | 112092 |
| 136 | 112093 |
| 138 | 112098 |
| 140 | 112099 |
| 142 | 112100 |

TABLE 4-continued

Correspondence of Compound Nos. to ER Nos.

| Compound # | ER # |
|---|---|
| 146 | 112859 |
| 148 | 112860 |
| 150 | 112861 |
| 152 | 113634 |
| 154 | 113635 |
| 156 | 113643 |
| 158 | 113644 |
| 160 | 113651 |
| 164 | 113665 |
| 166 | 113666 |
| 168 | 118023 |
| 170 | 019772 |
| 172 | 118989 |
| 176 | 118999 |
| 178 | 119000 |
| 180 | 119001 |
| 182 | 118949 |
| 184 | 119327 |
| 186 | 119328 |
| 188 | 119329 |
| 190 | 119521 |
| 192 | 119522 |
| 194 | 119523 |
| 196 | 803022 |
| 198 | 803045 |
| 200 | 803056 |
| 202 | 803058 |
| 204 | 803059 |
| 206 | 803592 |

Example 2

Intraperitoneal Administration of a TLR Agonist Enhances Therapeutic Efficacy of a Vaccine To determine the effect of Compound 804057 when administered intraperitoneally with a cancer vaccine, e.g., granulocyte-macrophage colony stimulating factor (GM-CSF) secreting tumor cells, a mouse model using melanoma cells was used. Compound 804057 is a TLR-4 (Toll-like receptor-4) agonist. B6 mice (C57BL6 mice) were engrafted subcutaneously with $1 \times 10^6$ F10 murine melanoma cells. Three days after tumor cell inoculation, the mice were either (1) vaccinated subcutaneously (s.c.) with $1 \times 10^6$ B16F10 tumor cells that were genetically modified to stably express and secrete murine GM-CSF (B16-GM-CSF cells); (2) vaccinated intraperitoneally (i.p.) with Compound 804057; or (3) were treated with a combination of s.c. GM-CSF cell vaccination and i.p. Compound 804057 (the GM-CSF cell vaccination and Compound 804057 vaccination were administered at separate sites in the mice). In these experiments, the GM-CSF cells were inactivated by gamma-irradiation prior to inoculation. Survival of the animals was monitored.

Figure 7:
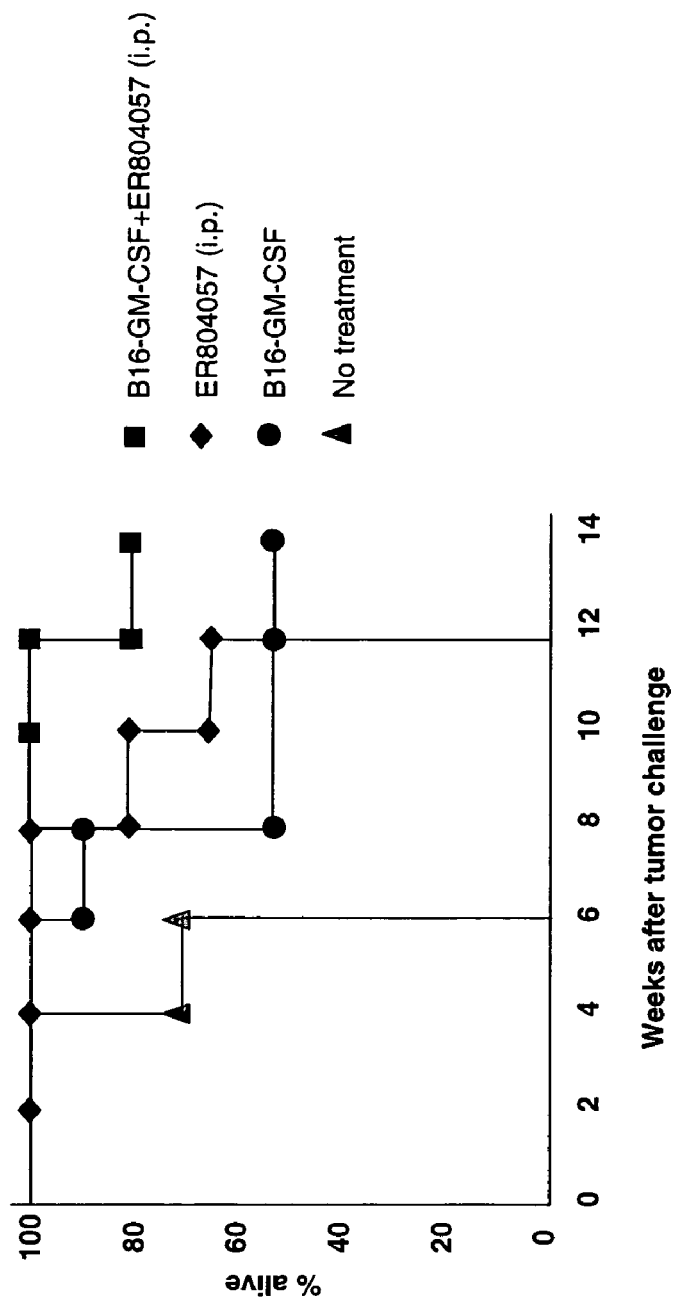
FIG. 7 is a graph depicting the percentage of tumor-bearing mice surviving after treatment with subcutaneous B16 GM-CSF(R) cells, Compound 804057, or B16 GM-CSF (r) cells and Compound 804057, or with no treatment.

These experiments demonstrated that vaccination of the animals with the B16 GM-CSF cells and i.p. Compound 804057 enhanced the therapeutic efficacy of the GM-CSF cells (FIG. 7).

Example 3

Local Administration of a TLR Agonist Enhances the Therapeutic Efficacy of a Cancer Vaccine The effect of Compound 804057 on treatment of B6 mice that were engrafted subcutaneously with $1 \times 10^6$ syngeneic B16F10 murine melanoma cells was examined. When tumors became palpable, the mice were injected intratumorally with GM-CSF cells alone, or in combination with Compound 804057 (about 3-10 µg). Survival of the animals was monitored.

Figure 8:
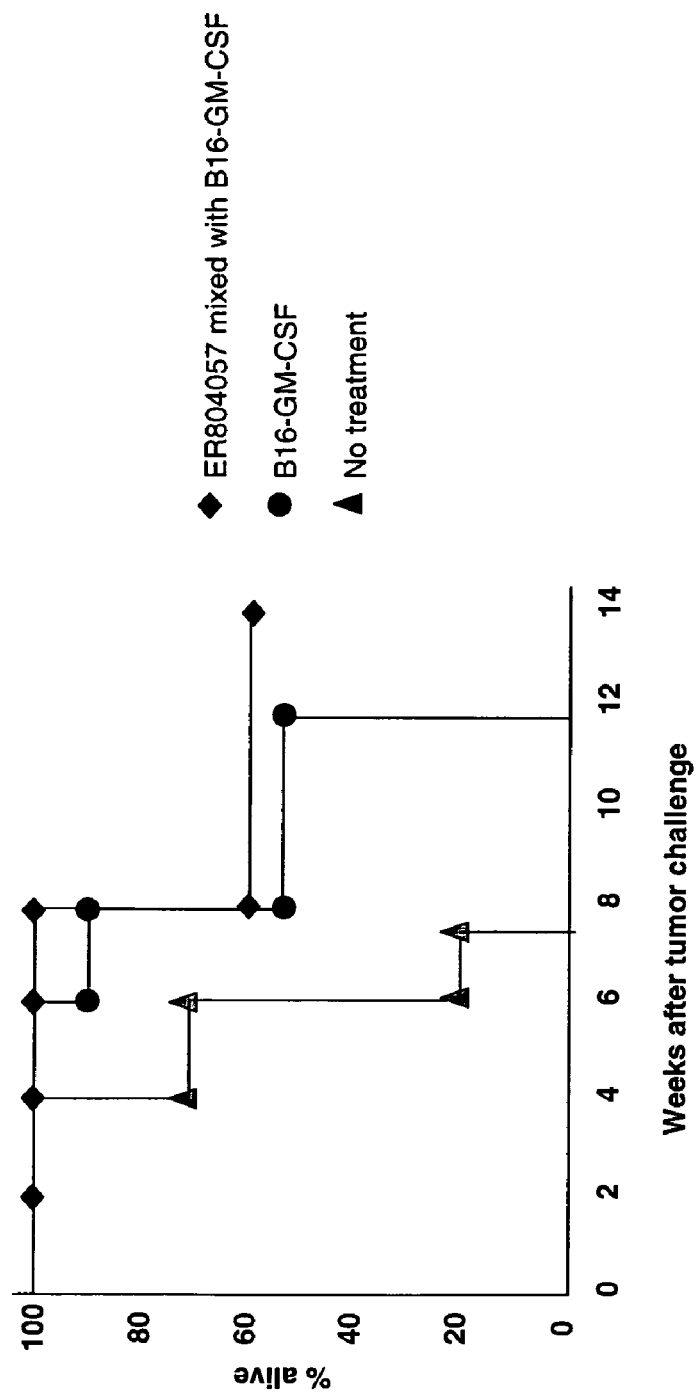
FIG. 8 is a graph depicting the percentage of tumor-bearing mice surviving after intratumoral treatment with B16 GM-CSF (R) cells, or B16 GM-CSF(r) cells and Compound 804057, or with no treatment.

It was found that the population of animals treated intratumorally with a combination of GM-CSF cells and Compound 804057 had increased survival compared to animals that were untreated or treated with GM-CSF cells alone (FIG. 8).

Example 4

MUC-1/Compound 804057 Vaccine Therapeutic Effects

To test the effects of a MUC-1 vaccine with Compound 804057 adjuvant for treating inflammatory bowel disease (IBD) and subsequent development of colon adenocarcinoma, an engineered mouse strain that lacks the IL-10 gene and expresses transgenic human MUC1 was used. Such mice spontaneously develop intestinal inflammation resembling IBD followed by colon adenocarcinoma. These data were presented and published in Beatty et al., AACR Annual Meeting 2006, Washington D.C., Apr. 4, 2006.

In these experiments, mice were immunized intranasally with 30 mg/nare of Tn MUC100mer (HGVTSAPDTRPAPG-STAPPA)×5, SEQ ID NO:1) and 3 mg of Compound 804057. Animals were vaccinated at about 4.5 weeks and boosted at about 6.5 weeks and 9 weeks.

Figure 9:
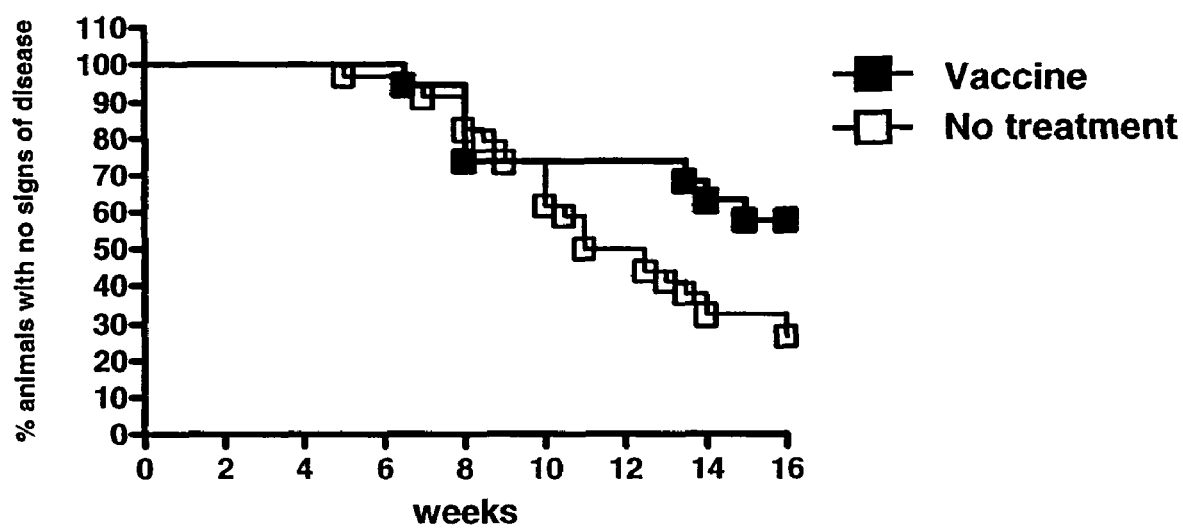
FIG. 9 is a graph depicting the percentage of animals without sign of disease after no treatment or treatment with vaccine and Compound 804057.
Figure 10:
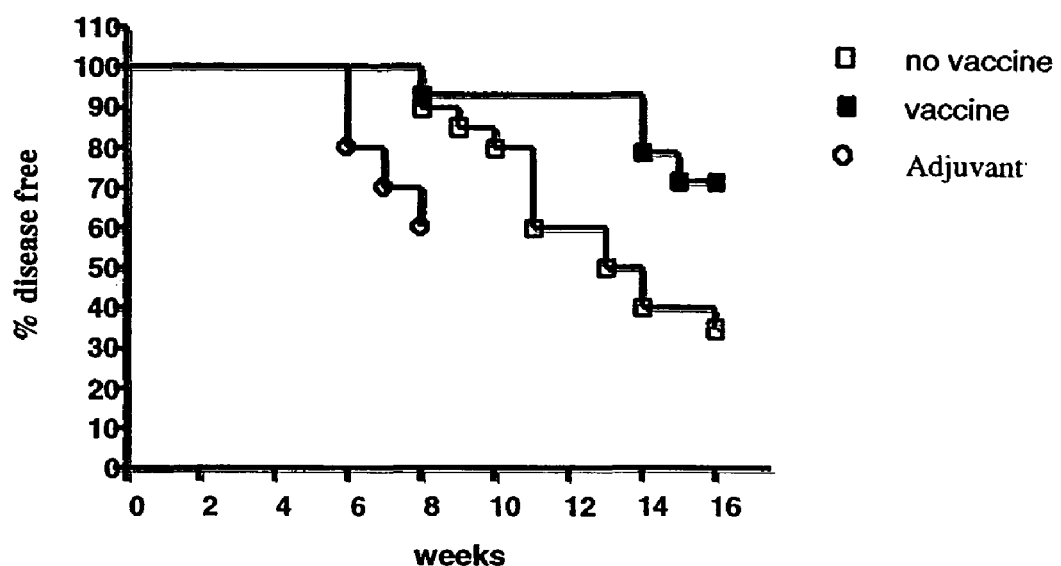
FIG. 10 is a graph depicting the percentage of animals alive after no treatment, treatment with vaccine, or treatment with Compound 804057.

MUC1 IL-10-/- mice treated with vaccine and Compound 804057 had delayed onset of IBD or did not develop IBD during the period of the experiment (FIG. 9). Mice treated with vaccine and Compound 804057 had improved survival and did not develop colon cancer (FIG. 10 and Table 5).

TABLE 5

| Treatment/no. of mice treated | Age (weeks) | Colon tumors |
|---|---|---|
| Vaccine/6 mice | 14-35.5 | 0/6 |
| Adjuvant/3 mice | 12.5-18 | 3/3 |
| No treatment/4 mice | 8-15.5 | 4/4 |

The data demonstrate that the addition of Compound 804057 to the MUC-1 vaccine can slow the progression to rectal prolapse associated with IBD, and suppresses the appearance of histologically detected tumors.

Example 5

EGFRvIII Therapeutic Effects with Adjuvant

To determine whether an adjuvant can enhance the effect of an oncology antigen (i.e., an antigen that can be used to vaccinate a subject individual against a cancer), C57/BL6J mice were immunized subcutaneously with a tumor-associated peptide, LEEKKGNYVVTDHC (SEQ ID NO:2) (derived from a mutant form of EGFR, EGFRvII) conjugated to the protein carrier keyhole limpet hemocyanin (KLH), with or without Compound 804057 or murine GM-CSF, a cytokine used in cancer vaccine trials to boost immune response. Compound 804057 was dosed at 3 µg, GM-CSF at 5 µg and the peptide-KLH conjugate at 25 µg per dose. Mice were immunized three times at intervals of three weeks. Serum was prepared from mice two weeks after each immunization and tested for EGFRvEII peptide-specific antibodies using ELISA on plates coated with EGFRvIII peptide conjugated to bovine serum albumin. The results in Table 3 are presented as titers from individual animals. The titer is defined as the last serum dilution at which a signal at 0.25 OD units above background was observed.

The data from these experiments demonstrate that Compound 804057 enhanced the mean titer of antigen-specific IgG2a, which binds high affinity Fc receptors involved in antibody-dependent cell-mediated cytotoxicity (ADCC). IgG2a is the mouse correlate of the human IgG1 isotype that is used in currently marketed human anti-tumor monoclonal antibodies, because it is most efficacious in tumor killing.

The combination of Compound 804057 and GM-CSF in the vaccination with EGFRvIII peptide demonstrated a greater effect on IgG2a titers than either material alone. These data demonstrate the usefulness of combinations of Compound 804057 with other immunoenhancers.

the subject an effective amount of one or more compounds of the formulae (II), (III), (IV), and (V):

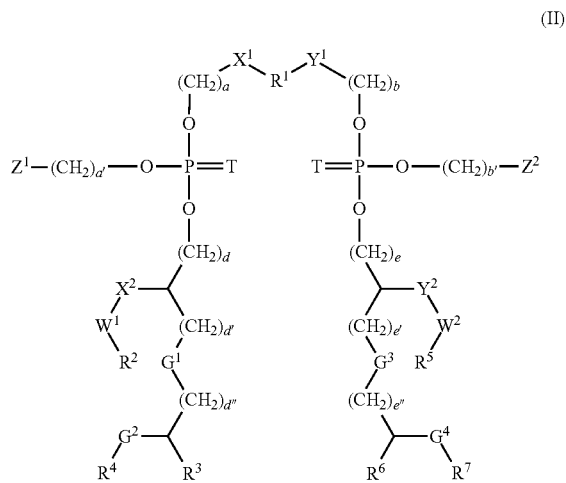

(II)

TABLE 6

Antibody titers to EGFRvIII peptide are enhanced by Compound 804057

| | Antigen administered with: | | | | | | | |
|---|---|---|---|---|---|---|---|---|
| | PBS | | Compound 804057 | | GM-CSF | | Compound 804057/GMCSF | |
| Antibody subclass: | IgG1 | IgG2a | IgG1 | IgG2a | IgG1 | IgG2a | IgG1 | IgG2a |
| | 6000 | 3000 | 3000 | 1500 | 12000 | 750 | 12000 | 3000 |
| | 12000 | 3000 | 24000 | 6000 | 12000 | 750 | 12000 | 6000 |
| | 24000 | 6000 | 24000 | 6000 | 12000 | 3000 | 24000 | 24000 |
| | 24000 | 6000 | 24000 | 12000 | 24000 | 3000 | 24000 | 24000 |
| | 24000 | 6000 | 24000 | 12000 | 24000 | 6000 | 48000 | 24000 |
| | 24000 | 6000 | 24000 | 12000 | 48000 | 6000 | 48000 | 48000 |
| | 48000 | 6000 | 24000 | 24000 | 48000 | 6000 | 48000 | 48000 |
| | 48000 | 24000 | 48000 | 48000 | 48000 | 24000 | 48000 | 48000 |
| Geometric mean titer: | 22008 | 6000 | 20182 | 10091 | 24000 | 3568 | 28541 | 20182 |

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of desensitizing a subject individual in need thereof against the occurrence of an allergic reaction in response to contact with a particular antigen or allergen, comprising administering to -continued

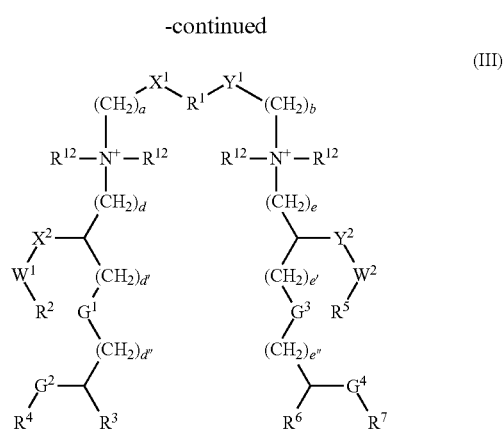

(III)

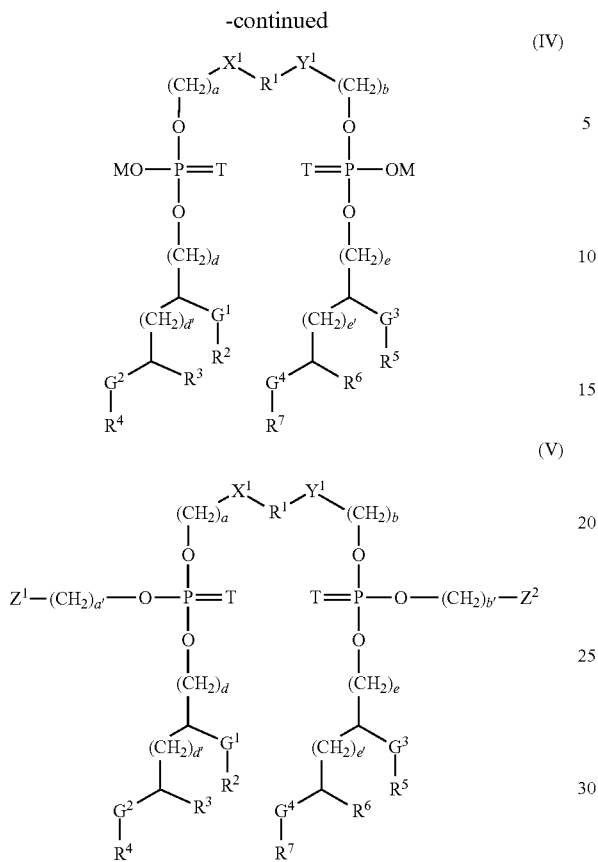

wherein:
R¹ is:
(a) —C(O)—;
(b) —C(O)—C₁₋₁₄alkyl-C(O)— or —C(O)—C₁₋₁₄alkenyl-C(O)—;
  wherein the —C₁₋₁₄alkyl- or —C₁₋₁₄alkenyl- is optionally substituted with one or more substituents selected from hydroxy, $C_{1-6}$alkyl, $C_{1-6}$alkoxy, $C_{1-6}$alkyldioxy, $C_{1-5}$ alkylamino, carboxy, $C_{1-6}$ alkoxycarbonyl, $C_{1-6}$ carbamoyl, $C_{1-6}$ acylamino, and/or (aryl)$C_{1-6}$alkyl; and
  wherein the aryl moiety of the (aryl)$C_{1-6}$-alkyl is optionally substituted with one or more substituents selected from $C_{1-6}$alkyl, $C_{1-6}$alkoxy, $C_{1-6}$alkylamino, $C_{1-6}$alkoxyamino, $C_{1-6}$alkylamino-$C_{1-6}$alkoxy, —O—$C_{1-6}$alkylamino-$C_{1-6}$alkoxy, —O—$C_{1-6}$alkylamino-C(O)—$C_{1-6}$alkyl-C(O)OH, —O—$C_{1-6}$alkylamino-C(O)—$C_{1-6}$alkyl-C(O)—$C_{1-6}$alkyl, —O—$C_{1-6}$alkyl-NH—$C_{1-6}$alkyl-O—$C_{1-6}$ alkyl, —O—$C_{1-6}$alkyl-NH—C(O)—$C_{1-6}$alkyl-C(O)OH, and/or —O—$C_{1-6}$alkyl-NH—C(O)—$C_{1-6}$alkyl-C(O)—$C_{1-6}$alkyl;
(c) a $C_2$ to $C_{15}$ straight or branched chain alkyl group optionally substituted with one or more hydroxy and/or alkoxy groups; or
(d) —C(O)—$C_{6-12}$aryl-C(O)— wherein the aryl is optionally substituted with one or more hydroxy, halo, nitro, amino, $C_{1-6}$alkyl and/or $C_{1-6}$alkoxy groups;

a and b are each independently 0, 1, 2, 3 or 4;
a' and b' are independently 2, 3, 4, 5, 6, 7 or 8;
d and e are each independently 1, 2, 3, 4, 5 or 6;
d' and e' are each independently 0, 1, 2, 3 or 4;
d" and e" are each independently 0, 1, 2, 3 or 4;
T is oxygen or sulfur;
X¹ and Y¹ are each independently oxygen, NH, —N(C(O)C₁₋₄alkyl)-, or —N(C₁₋₄-alkyl)-;
X² and Y² are each independently null, oxygen, NH, —N(C(O)C₁₋₄alkyl)-, or —N(C₁₋₄alkyl)-;
W¹ and W² are each independently carbonyl, methylene, sulfone or sulfoxide;
R², R³, R⁴, R⁵, R⁶ and R⁷ are each independently:
 (a) $C_2$ to $C_{20}$ straight chain or branched chain alkyl, which is optionally substituted with one or more oxo, halo, hydroxy and/or alkoxy groups;
 (b) $C_2$ to $C_{20}$ straight chain or branched chain alkenyl, which is optionally substituted with one or more of oxo, halo, hydroxy and/or alkoxy groups;
 (c) $C_2$ to $C_{20}$ straight chain or branched chain alkoxy, which is optionally substituted with one or more oxo, halo, hydroxy and/or alkoxy groups;
 (d) —NH—$C_{2-20}$ straight chain or branched chain alkyl, wherein the alkyl group is optionally substituted with one or more oxo, halo, hydroxy and/or alkoxy groups;
 (e) —C(O)—$C_{2-20}$ straight chain or branched chain alkyl or alkenyl, wherein the alkyl or alkenyl is optionally substituted with one or more oxo, halo, hydroxy and/or alkoxy groups;
 (f)

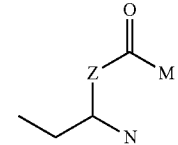

Z is O or NH; and M and N are each independently $C_2$ to $C_{20}$ straight chain or branched chain alkyl, alkenyl, alkoxy, acyloxy, alkylamino, or acylamino;

(g)

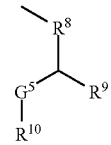

R⁸ is $C_{1-6}$ straight or branched chain alkyl or $C_{2-6}$ straight or branched chain alkenyl or alkynyl;
 R⁹ and R¹⁰ are independently selected from the group consisting of
  (i) $C_1$ to $C_{20}$ straight chain or branched chain alkyl, which is optionally substituted with one or more halo, oxo, hydroxy and/or alkoxy; and
  (ii) $C_2$ to $C_{20}$ straight chain or branched chain alkenyl or alkynyl which is optionally substituted with one or more halo, oxo, hydroxy and/or alkoxy;

$G^1$, $G^2$, $G^3$, $G^4$ and $G^5$ are each independently oxygen, methylene, —NH—, thiol, —N($C_{1-4}$alkyl)-, —N[C(O)—$C_{1-4}$alkyl]-, —NH—C(O)—, —NH—$SO_2$—, —C(O)—O—, —C(O)—NH—, —O—C(O)—, —O—C(O)—NH—, —O—C(O)—O—, —NH—C(O)—NH—, —C(O)NH—, —C(O)N($C_{1-4}$alkyl), aryl, and —S(O)$_n$—, where n is 0, 1, or 2;

or $G^1R^2$, $G^2R^4$, $G^3R^5$ and/or $G^4R^7$ may together be a hydrogen atom or hydroxyl;

$Z^1$ and $Z^2$ are each independently selected from —OP(O)(OH)$_2$, —P(O)(OH)$_2$, —OP(O)(OR$^8$)(OH) {where $R^8$ is a $C_{1-4}$alkyl}, —OS(O)$_2$OH, —S(O)$_2$OH—, —CO$_2$H, —OB(OH)$_2$, —OH, —CH$_3$, —NH$_2$, and —N(R$^9$)$_2$ {where $R^9$ is a $C_{1-4}$alkyl};

$R^{12}$ is H or a $C_{1-4}$ straight or branched alkyl; and

M is independently selected from a hydrogen atom and a pharmaceutically acceptable cation {a monovalent cation will take the place of one M, while a divalent cation will take the place of two M variables};

and/or a pharmaceutically acceptable salt, stereoisomer, amorphous solid thereof, or any combination thereof.

2. The method of claim 1, wherein the subject individual suffers from asthma, atopic dermatitis, or allergic rhinitis.

3. A method of reducing ischemic damage in a subject individual in need thereof, the method comprising administering to the subject an effective amount of one or more compounds of the formulae (II), (III), (IV), and (V):

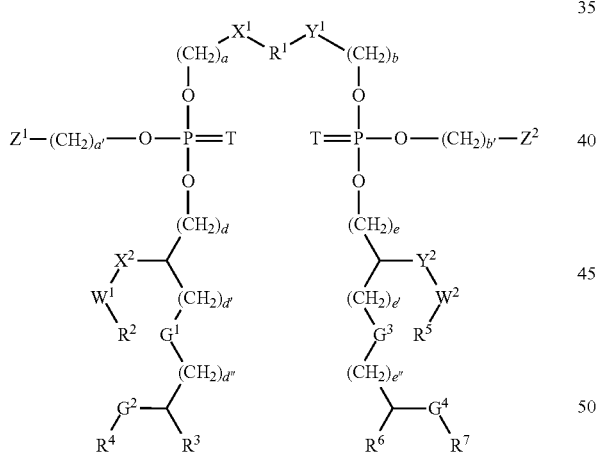

(II)

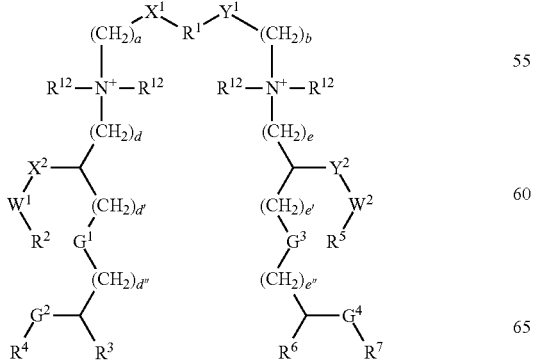

(III)

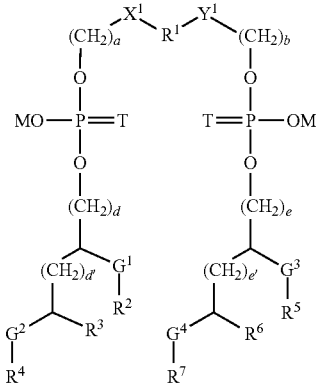

(IV)

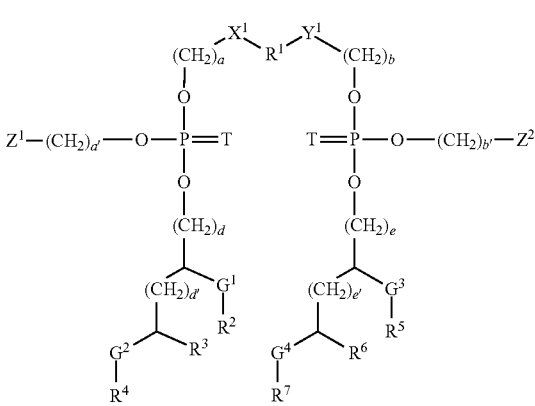

(V)

wherein:
$R^1$ is:
(a) —C(O)—;
(b) —C(O)—$C_{1-14}$alkyl-C(O)— or —C(O)—$C_{1-14}$alkenyl-C(O)—;
wherein the —$C_{1-14}$alkyl- or —$C_{1-14}$alkenyl- is optionally substituted with one or more substituents selected from hydroxy, $C_{1-6}$alkoxy, $C_{1-6}$alkyldioxy, $C_{1-5}$ alkylamino, carboxy, $C_{1-6}$ alkoxycarbonyl, $C_{1-6}$ carbamoyl, $C_{1-6}$ acylamino, and/or (aryl)$C_{1-6}$alkyl; and
wherein the aryl moiety of the (aryl)$C_{1-6}$-alkyl is optionally substituted with one or more substituents selected from $C_{1-6}$alkyl, $C_{1-6}$alkoxy, $C_{1-6}$alkylamino, $C_{1-6}$alkoxyamino, $C_{1-6}$alkylamino-$C_{1-6}$alkoxy, —O—$C_{1-6}$alkylamino-C(O)—$C_{1-6}$alkyl-C(O)OH, —O—$C_{1-6}$alkylamino-C(O)—$C_{1-6}$alkyl-C(O)—$C_{1-6}$alkyl, —O—$C_{1-6}$alkyl-NH—$C_{1-6}$alkyl-O—$C_{1-6}$ alkyl, —O—$C_{1-6}$alkyl-NH—C(O)—$C_{1-6}$alkyl-C(O)OH, and/or —O—$C_{1-6}$alkyl-NH—C(O)—$C_{1-6}$alkyl-C(O)—$C_{1-6}$alkyl;
(c) a $C_2$ to $C_{15}$ straight or branched chain alkyl group optionally substituted with one or more hydroxy and/or alkoxy groups; or
(d) —C(O)—$C_{6-12}$aryl-C(O)— wherein the aryl is optionally substituted with one or more hydroxy, halo, nitro, amino, $C_{1-6}$alkyl and/or $C_{1-6}$alkoxy groups;
a and b are each independently 0, 1, 2, 3 or 4;
a' and b' are independently 2, 3, 4, 5, 6, 7 or 8;
d and e are each independently 1, 2, 3, 4, 5 or 6;
d' and e' are each independently 0, 1, 2, 3 or 4;
d" and e" are each independently 0, 1, 2, 3 or 4;

T is oxygen or sulfur;

$X^1$ and $Y^1$ are each independently oxygen, NH, —N(C(O)$C_{1-4}$alkyl)-, or —N($C_{1-4}$alkyl)-;

$X^2$ and $Y^2$ are each independently null, oxygen, NH, —N(C(O)$C_{1-4}$alkyl)-, or —N($C_{1-4}$alkyl)-;

$W^1$ and $W^2$ are each independently carbonyl, methylene, sulfone or sulfoxide;

$R^2$, $R^3$, $R^4$, $R^5$, $R^6$ and $R^7$ are each independently:
(a) $C_2$ to $C_{20}$ straight chain or branched chain alkyl, which is optionally substituted with one or more oxo, halo, hydroxy and/or alkoxy groups;
(b) $C_2$ to $C_{20}$ straight chain or branched chain alkenyl, which is optionally substituted with one or more of oxo, halo, hydroxy and/or alkoxy groups;
(c) $C_2$ to $C_{20}$ straight chain or branched chain alkoxy, which is optionally substituted with one or more oxo, halo, hydroxy and/or alkoxy groups;
(d) —NH—$C_{2-20}$ straight chain or branched chain alkyl, wherein the alkyl group is optionally substituted with one or more oxo, halo, hydroxy and/or alkoxy groups;
(e) —C(O)—$C_{2-20}$ straight chain or branched chain alkyl or alkenyl, wherein the alkyl or alkenyl is optionally substituted with one or more oxo, halo, hydroxy and/or alkoxy groups;

(f)

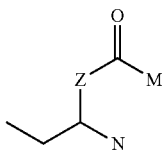

Z is O or NH; and M and N are each independently $C_2$ to $C_{20}$ straight chain or branched chain alkyl, alkenyl, alkoxy, acyloxy, alkylamino, or acylamino;

(g)

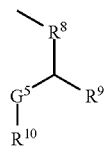

$R^8$ is $C_{1-6}$ straight or branched chain alkyl or $C_{2-6}$ straight or branched chain alkenyl or alkynyl;

$R^9$ and $R^{10}$ are independently selected from the group consisting of
(i) $C_1$ to $C_{20}$ straight chain or branched chain alkyl, which is optionally substituted with one or more halo, oxo, hydroxy and/or alkoxy; and
(ii) $C_2$ to $C_{20}$ straight chain or branched chain alkenyl or alkynyl which is optionally substituted with one or more halo, oxo, hydroxy and/or alkoxy;

$G^1$, $G^2$, $G^3$, $G^4$ and $G^5$ are each independently oxygen, methylene, —NH—, thiol, —N($C_{1-4}$alkyl)-, —N[C(O)—$C_{1-4}$alkyl]-, —NH—C(O)—, —NH—SO$_2$—, —C(O)—O—, —C(O)—NH—, —O—C(O)—, —O—C(O)—NH—, —O—C(O)—O—, —NH—, —C(O)—NH—, —C(O)NH—, —C(O)N($C_{1-4}$alkyl), aryl, and —S(O)$_n$—, where n is 0, 1, or 2;

or $G^1R^2$, $G^2R^4$, $G^3R^5$ and/or $G^4R^7$ may together be a hydrogen atom or hydroxyl;

$Z^1$ and $Z^2$ are each independently selected from —OP(O)(OH)$_2$, —P(O)(OH)$_2$, —OP(O)(OR$^8$)(OH) {where $R^8$ is a $C_{1-4}$alkyl}, —OS(O)$_2$OH, —S(O)$_2$OH—, —CO$_2$H, —OB(OH)$_2$, —OH, —CH$_3$, —NH$_2$, and —N($R^9$)$_2$ {where $R^9$ is a $C_{1-4}$alkyl};

$R^{12}$ is H or a $C_{1-4}$ straight or branched alkyl; and

M is independently selected from a hydrogen atom and a pharmaceutically acceptable cation {a monovalent cation will take the place of one M, while a divalent cation will take the place of two M variables};

and/or a pharmaceutically acceptable salt, stereoisomer, amorphous solid thereof, or any combination thereof prior to performing surgery on the individual.

4. A method of ameliorating or delaying asthma in a subject individual in need thereof, the method comprising administering to the subject an effective amount of one or more compounds of the formulae (II), (III), (IV), and (V):

(II)

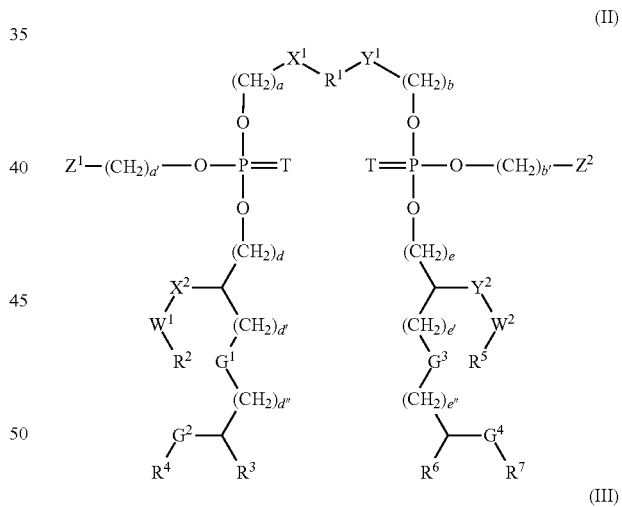

(III)

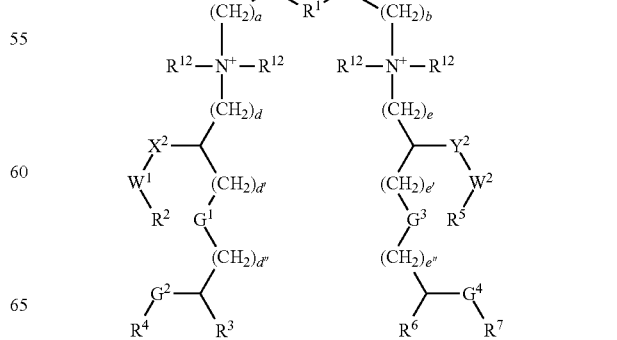

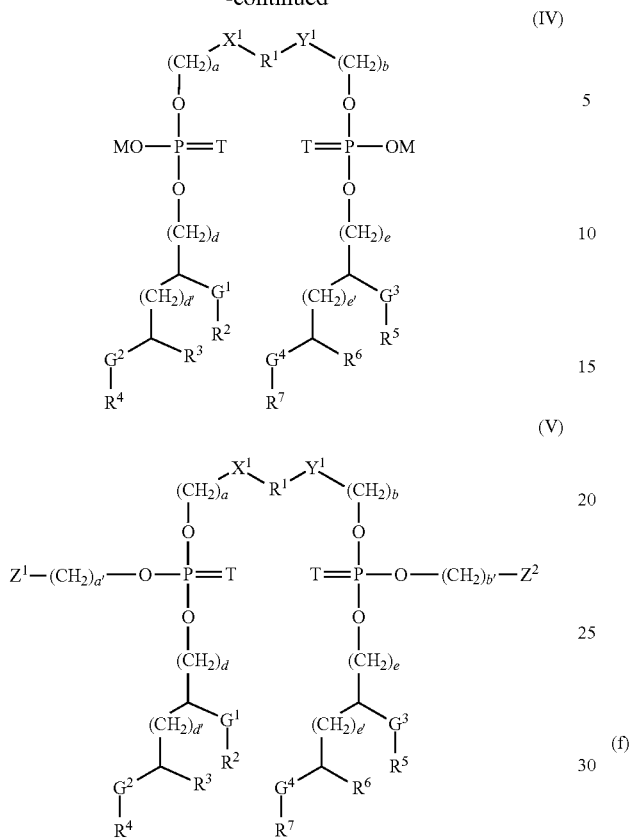

(IV)

(V)

wherein:

R$^1$ is:
(a) —C(O)—;
(b) —C(O)—C$_{1-14}$alkyl-C(O)— or —C(O)—C$_{1-14}$alkenyl-C(O)—;
  wherein the —C$_{1-14}$alkyl- or —C$_{1-14}$alkenyl- is optionally substituted with one or more substituents selected from hydroxy, C$_{1-6}$alkyl, C$_{1-6}$alkoxy, C$_{1-6}$alkyldioxy, C$_{1-5}$ alkylamino, carboxy, C$_{1-6}$ alkoxycarbonyl, C$_{1-6}$ carbamoyl, C$_{1-6}$ acylamino, and/or (aryl)C$_{1-6}$alkyl; and
  wherein the aryl moiety of the (aryl)C$_{1-6}$-alkyl is optionally substituted with one or more substituents selected from C$_{1-6}$alkyl, C$_{1-6}$alkoxy, C$_{1-6}$alkylamino, C$_{1-6}$alkoxyamino, C$_{1-6}$alkylamino-C$_{1-6}$alkoxy, —O—C$_{1-6}$alkylamino-C$_{1-6}$alkoxy, —O—C$_{1-6}$alkylamino-C(O)—C$_{1-6}$alkyl-C(O)OH, —O—C$_{1-6}$alkylamino-C(O)—C$_{1-6}$alkyl-C(O)—C$_{1-6}$alkyl, —O—C$_{1-6}$alkyl-NH—C$_{1-6}$alkyl-O—C$_{1-6}$ alkyl, —O—C$_{1-6}$alkyl-NH—C(O)—C$_{1-6}$ alkyl-C(O)OH, and/or —O—C$_{1-6}$alkyl-NH—C(O)—C$_{1-6}$alkyl-C(O)—C$_{1-6}$alkyl;
(c) a C$_2$ to C$_{15}$ straight or branched chain alkyl group optionally substituted with one or more hydroxy and/or alkoxy groups; or
(d) —C(O)—C$_{6-12}$aryl-C(O)— wherein the aryl is optionally substituted with one or more hydroxy, halo, nitro, amino, C$_{1-6}$alkyl and/or C$_{1-6}$alkoxy groups;

a and b are each independently 0, 1, 2, 3 or 4;
a' and b' are independently 2, 3, 4, 5, 6, 7 or 8;
d and e are each independently 1, 2, 3, 4, 5 or 6;
d' and e' are each independently 0, 1, 2, 3 or 4;

d" and e" are each independently 0, 1, 2, 3 or 4;
T is oxygen or sulfur;
X$^1$ and Y$^1$ are each independently oxygen, NH, —N(C(O)C$_{1-4}$alkyl)-, or —N(C$_{1-4}$alkyl)-;
X$^2$ and Y$^2$ are each independently null, oxygen, NH, —N(C(O)C$_{1-4}$alkyl)-, or —N(C$_{1-4}$alkyl)-;
W$^1$ and W$^2$ are each independently carbonyl, methylene, sulfone or sulfoxide;
R$^2$, R$^3$, R$^4$, R$^5$, R$^6$ and R$^7$ are each independently:
(a) C$_2$ to C$_{20}$ straight chain or branched chain alkyl, which is optionally substituted with one or more oxo, halo, hydroxy and/or alkoxy groups;
(b) C$_2$ to C$_{20}$ straight chain or branched chain alkenyl, which is optionally substituted with one or more of oxo, halo, hydroxy and/or alkoxy groups;
(c) C$_2$ to C$_{20}$ straight chain or branched chain alkoxy, which is optionally substituted with one or more oxo, halo, hydroxy and/or alkoxy groups;
(d) —NH—C$_{2-20}$ straight chain or branched chain alkyl, wherein the alkyl group is optionally substituted with one or more oxo, halo, hydroxy and/or alkoxy groups;
(e) —C(O)—C$_{2-20}$ straight chain or branched chain alkyl or alkenyl, wherein the alkyl or alkenyl is optionally substituted with one or more oxo, halo, hydroxy and/or alkoxy groups;

(f)

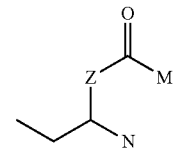

Z is O or NH; and M and N are each independently C$_2$ to C$_{20}$ straight chain or branched chain alkyl, alkenyl, alkoxy, acyloxy, alkylamino, or acylamino;

(g)

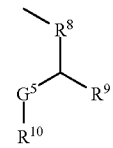

R$^8$ is C$_{1-6}$ straight or branched chain alkyl or C$_{2-6}$ straight or branched chain alkenyl or alkynyl;
R$^9$ and R$^{10}$ are independently selected from the group consisting of
(i) C$_1$ to C$_{20}$ straight chain or branched chain alkyl, which is optionally substituted with one or more halo, oxo, hydroxy and/or alkoxy; and
(ii) C$_2$ to C$_{20}$ straight chain or branched chain alkenyl or alkynyl which is optionally substituted with one or more halo, oxo, hydroxy and/or alkoxy;
G$^1$, G$^2$, G$^3$, G$^4$ and G$^5$ are each independently oxygen, methylene, —NH—, thiol, —N(C$_{1-4}$alkyl)-, —N[C(O)—C$_{1-4}$alkyl]-, —NH—C(O)—, —NH—SO$_2$—, —C(O)—O—, —C(O)—NH—, —O—C(O)—, —O—C(O)—NH—, —O—C(O)—O—, —NH—C(O)—NH—, —C(O)NH—, —C(O)N(C$_{1-4}$alkyl), aryl, and —S(O)$_n$—, where n is 0, 1, or 2;

or $G^1R^2$, $G^2R^4$, $G^3R^5$ and/or $G^4R^7$ may together be a hydrogen atom or hydroxyl;

$Z^1$ and $Z^2$ are each independently selected from —OP(O)(OH)$_2$, —P(O)(OH)$_2$, —OP(O)(OR$^8$)(OH) {where $R^8$ is a $C_{1-4}$alkyl}, —OS(O)$_2$OH, —S(O)$_2$OH—, —CO$_2$H, —OB(OH)$_2$, —OH, —CH$_3$, —NH$_2$, and —N(R$^9$)$_2$ {where $R^9$ is a $C_{1-4}$alkyl};

$R^{12}$ is H or a $C_{1-4}$ straight or branched alkyl; and

M is independently selected from a hydrogen atom and a pharmaceutically acceptable cation {a monovalent cation will take the place of one M, while a divalent cation will take the place of two M variables};

and/or a pharmaceutically acceptable salt, stereoisomer, amorphous solid thereof, or any combination thereof.

5. A method of inducing or stimulating an immune response in a subject individual, comprising administering an effective amount of one or more compounds of formula (I):

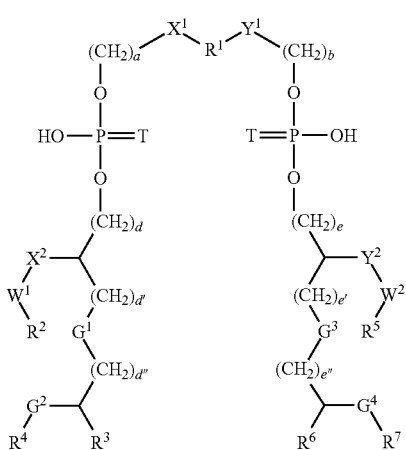

(I)

wherein:
R$^1$ is selected from the group consisting of:
(a) —C(O)—;
(b) C(O)—C$_{2-15}$ alkyl-C(O)—, optionally substituted with hydroxy or alkoxy;
(c) a C$_2$ to C$_{15}$ straight or branched chain alkyl optionally substituted with hydroxy or alkoxy;
a and b are independently 2, 3 or 4;
d and e are independently an integer from 1 to 4;
d' and e' are 1;
d" and e" are 2;
T is oxygen;
X$^1$ and Y$^1$ are NH;
X$^2$ and Y$^2$ are independently selected from the group consisting of oxygen and NH;
W$^1$ and W$^2$ are carbonyl,
R$^2$ and R$^5$ are each independently:
(a) C$_2$ to C$_{20}$ straight chain or branched chain alkyl which is optionally substituted with hydroxy or alkoxy;
(b) C$_2$ to C$_{20}$ straight chain or branched chain alkenyl which is optionally substituted with hydroxy or alkoxy;
(c) CH$_2$-alkyl carbonyl;
(d) CH$_2$-alkenyl carbonyl;

(e)

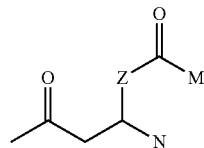

wherein Z is selected from the group consisting of O and NH, and M and N are independently selected from the group consisting of C$_2$ to C$_{20}$ straight chain or branched chain alkyl, alkenyl, alkoxy, acyloxy, alkylamino, and acylamino;

R$^3$ and R$^6$ are independently selected from the group consisting of C$_2$ to C$_{20}$ straight chain or branched chain alkyl or alkenyl;

R$^4$ and R$^7$ are independently selected from the group consisting of hydrogen, C$_2$ to C$_{20}$ straight chain or branched chain alkyl or alkenyl; C$_2$ to C$_{20}$ straight chain or branched chain alkyl carbonyl; C$_2$ to C$_{20}$ straight chain or branched chain alkenyl carbonyl; optionally substituted with hydroxy or alkoxy;

G$^1$, G$^2$, G$^3$, and G$^4$ are oxygen
or a pharmaceutically acceptable salt, thereof.

6. A method for upregulation of the immune system in a subject individual, comprising administering a therapeutically effective amount of one or more compounds of formula (I):

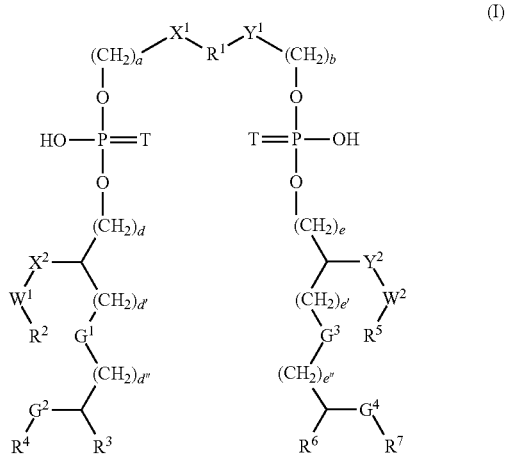

(I)

wherein:
R$^1$ is selected from the group consisting of:
(a) —C(O)—;
(b) C(O)—C$_{2-15}$ alkyl-C(O)—, optionally substituted with hydroxy or alkoxy
(c) a C$_2$ to C$_{15}$ straight or branched chain alkyl optionally substituted with hydroxy or alkoxy;
a and b are independently 2, 3 or 4;
d and e are independently an integer from 1 to 4;
d' and e' are 1;
d" and e" are 2;
T is oxygen;
X$^1$ and Y$^1$ are NH;
X$^2$ and Y$^2$ are independently selected from the group consisting of oxygen and NH;
W$^1$ and W$^2$ are carbonyl;

$R^2$ and $R^5$ are each independently:
(a) $C_2$ to $C_{20}$ straight chain or branched chain alkyl which is optionally substituted with hydroxy or alkoxy;
(b) $C_2$ to $C_{20}$ straight chain or branched chain alkenyl which is optionally substituted with hydroxy or alkoxy;
(c) $CH_2$-alkyl carbonyl;
(d) $CH_2$-alkenyl carbonyl;

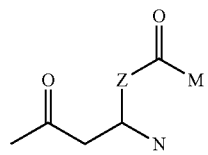

(e)

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;
$R^3$ and $R^6$ are independently selected from the group consisting of $C_2$ to $C_{20}$ straight chain or branched chain alkyl or alkenyl;
$R^4$ and $R^7$ are independently selected from the group consisting of hydrogen, $C_2$ to $C_{20}$ straight chain or branched chain alkyl or alkenyl; $C_2$ to $C_{20}$ straight chain or branched chain alkyl carbonyl; $C_2$ to $C_{20}$ straight chain or branched chain alkenyl carbonyl; optionally substituted with hydroxy or alkoxy;
$G^1$, $G^2$, $G^3$, and oxygen
or a pharmaceutically acceptable salt, thereof.

7. A method of desensitizing a subject individual in need thereof against the occurrence of an allergic reaction in response to contact with a particular antigen or allergen, comprising administering to the subject an effective amount of one or more compounds of formula (I):

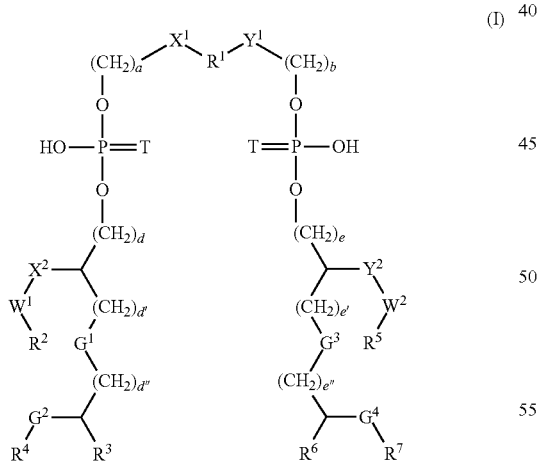

(I)

wherein:
$R^1$ is selected from the group consisting of:
(a) —C(O)—;
(b) —C(O)—$C_{1-14}$ alkyl-C(O)—, wherein said —$C_{1-14}$ alkyl- is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-5}$-alkyl-aryl is optionally substituted with $C_{1-5}$ alkoxy, $C_{1-5}$ alkylamino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl-C(O)OH, —O—$C_{1-5}$ alkylamino-C(O)—$C_{1-5}$ alkyl-C(O)—$C_{1-5}$ alkyl;
(c) a $C_2$ to $C_{15}$ straight or branched chain alkyl optionally substituted with hydroxy or alkoxy; and
(d) —C(O)—$C_{6-12}$ arylene-C(O)— wherein said arylene is optionally substituted with hydroxy, halogen, nitro or amino;
a and b are independently 0, 1, 2, 3 or 4;
d, d', d", e, e', and e" e are independently an integer from 1 to 4;
T is oxygen;
$X^1$, $X^2$, $Y^1$, and $Y^2$ are independently selected from the group consisting of a null, oxygen, NH, $N(C(O)C_{1-4}$ alkyl), and $N(C_{1-4}$ alkyl$)_2$;
$W^1$ and $W^2$ are independently selected from the group consisting of carbonyl, methylene, sulfone and sulfoxide;
$R^2$ and $R^5$ are each independently:
(a) $C_2$ to $C_{20}$ straight chain or branched chain alkyl which is optionally substituted with oxo, hydroxy or alkoxy;
(b) $C_2$ to $C_{20}$ straight chain or branched chain alkenyl or dialkenyl which is optionally substituted with oxo, hydroxy or alkoxy;
(c) $C_2$ to $C_{20}$ straight chain or branched chain alkoxy which is optionally substituted with oxo, hydroxy or alkoxy;
(d) —NH—$C_2$ to $C_{20}$ straight chain or branched chain alkyl, wherein said alkyl group is optionally substituted with oxo, hydroxy or alkoxy;

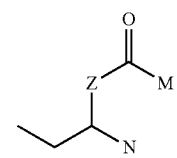

(e)

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;
$R^3$ and $R^6$ are independently selected from the group consisting of $C_2$ to $C_{20}$ straight chain or branched chain alkyl or alkenyl optionally substituted with oxo or fluoro;
$R^4$ and $R^7$ are independently selected from the group consisting of $C(O)C_2$ to $C_{20}$ straight chain or branched chain alkyl or alkenyl; $C_2$ to $C_{20}$ straight chain or branched chain alkoxy;
$C_2$ to $C_{20}$ straight chain or branched chain alkenyl; wherein said alkyl, alkenyl, or alkoxy groups can be independently and optionally substituted with hydroxy, fluoro or $C_1$ to $C_5$ alkoxy;
$G^1$, $G^2$, $G^3$, and $G^4$ are independently selected from the group consisting of oxygen, methylene, amino, thiol, —NHC(O)—, and —NC(O)$C_{1-4}$alkyl)-;
or $G^2R^4$ or $G^4R^7$ may together be a hydrogen atom or hydroxyl;
or a pharmaceutically acceptable salt, stereoisomer, amorphous solid thereof, or any combination thereof.

8. The method of claim 7, wherein the subject individual suffers from asthma, atopic dermatitis, or allergic rhinitis.

9. An immunostimulatory remedy containing, as the active ingredient, one or more compounds of formula (I):

$$\text{(I)}$$

[chemical structure of formula (I)]

wherein:
R$^1$ is selected from the group consisting of:
  (a) —C(O)—;
  (b) C(O)—C$_{2-15}$ alkyl-C(O)—, optionally substituted with hydroxy or alkoxy;
  (c) a C$_2$ to C$_{15}$ straight or branched chain alkyl optionally substituted with hydroxy or alkoxy;
a and b are independently 2, 3 or 4;
d and e are independently an integer from 1 to 4;
d' and e' are 1;
d" and e" are 2;
T is oxygen;
X$^1$ and Y$^1$ are NH;
X$^2$ and Y$^2$ are independently selected from the group consisting of oxygen and NH;
W$^1$ and W$^2$ are carbonyl;
R$^2$ and R$^5$ are each independently:
  (a) C$_2$ to C$_{20}$ straight chain or branched chain alkyl which is optionally substituted with hydroxy or alkoxy;
  (b) C$_2$ to C$_{20}$ straight chain or branched chain alkenyl which is optionally substituted with hydroxy or alkoxy;
  (c) CH$_2$-alkyl carbonyl;
  (d) CH$_2$-alkenyl carbonyl;
  (e)

[chemical structure]

wherein Z is selected from the group consisting of O and NH, and M and N are independently selected from the group consisting of C$_2$ to C$_{20}$ straight chain or branched chain alkyl, alkenyl, alkoxy, acyloxy, alkylamino, and acylamino;
R$^3$ and R$^6$ are independently selected from the group consisting of C$_2$ to C$_{20}$ straight chain or branched chain alkyl or alkenyl;
R$^4$ and R$^7$ are independently selected from the group consisting of hydrogen, C$_2$ to C$_{20}$ straight chain or branched chain alkyl or alkenyl; C$_2$ to C$_{20}$ straight chain or branched chain alkyl carbonyl; C$_2$ to C$_{20}$ straight chain or branched chain alkenyl carbonyl; optionally substituted with hydroxy or alkoxy;
G$^1$, G$^2$, G$^3$, and G$^4$ are oxygen;
or a pharmaceutically acceptable salt, thereof.

10. A method of reducing ischemic damage in a subject individual in need thereof, the method comprising administering to the subject an effective amount of one or more compounds of formula (I):

$$\text{(I)}$$

[chemical structure of formula (I)]

wherein:
R$^1$ is selected from the group consisting of:
  (a) —C(O)—;
  (b) —C(O)—C$_{1-14}$ alkyl-C(O)—, wherein said —C$_{1-14}$ alkyl- is optionally substituted with hydroxy, C$_{1-5}$ alkoxy, C$_{1-5}$ alkylenedioxy, C$_{1-5}$ alkylamino, or C$_{1-5}$-alkyl-aryl, wherein said aryl moiety of said C$_{1-5}$-alkyl-aryl is optionally substituted with C$_{1-5}$ alkoxy, C$_{1-5}$ alkylamino, C$_{1-5}$ alkoxy-amino, C$_{1-5}$ alkylamino-C$_{1-5}$ alkoxy, —O—C$_{1-5}$ alkylamino-C$_{1-5}$ alkoxy, —O—C$_{1-5}$ alkylamino-C(O)—C$_{1-5}$ alkyl-C(O)OH, —O—C$_{1-5}$ alkylamino-C(O)—C$_{1-5}$ alkyl-C(O)—C$_{1-5}$ alkyl;
  (c) a C$_2$ to C$_{15}$ straight or branched chain alkyl optionally substituted with hydroxy or alkoxy; and
  (d) —C(O)—C$_{6-12}$ arylene-C(O)— wherein said arylene is optionally substituted with hydroxy, halogen, nitro or amino;
a and b are independently 0, 1, 2, 3 or 4;
d, d', d", e, e', and e" e are independently an integer from 1 to 4;
T is oxygen;
X$^1$, X$^2$, Y$^1$, and Y$^2$ are independently selected from the group consisting of a null, oxygen, NH, N(C(O)C$_{1-4}$ alkyl), and N(C$_{1-4}$ alkyl)$_2$;
W$^1$ and W$^2$ are independently selected from the group consisting of carbonyl, methylene, sulfone and sulfoxide;
R$^2$ and R$^5$ are each independently:
  (a) C$_2$ to C$_{20}$ straight chain or branched chain alkyl which is optionally substituted with oxo, hydroxy or alkoxy;
  (b) C$_2$ to C$_{20}$ straight chain or branched chain alkenyl or dialkenyl which is optionally substituted with oxo, hydroxy or alkoxy;
  (c) C$_2$ to C$_{20}$ straight chain or branched chain alkoxy which is optionally substituted with oxo, hydroxy or alkoxy;

(d) —NH—$C_2$ to $C_{20}$ straight chain or branched chain alkyl, wherein said alkyl group is optionally substituted with oxo, hydroxy or alkoxy;

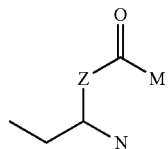

(e)

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with oxo or fluoro;

$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkoxy;

$C_2$ to $C_{20}$ straight chain or branched chain alkenyl; wherein said alkyl, alkenyl, or alkoxy groups can be independently and optionally substituted with hydroxy, fluoro or $C_1$ to $C_5$ alkoxy;

$G^1$, $G^2$, $G^3$, and $G^4$ are independently selected from the group consisting of oxygen, methylene, amino, thiol, —NHC(O)—, and —NC(O)$C_{1-4}$alkyl)-;

or $G^2R^4$ or $G^4R^7$ may together be a hydrogen atom or hydroxyl;

or a pharmaceutically acceptable salt, stereoisomer, amorphous solid thereof, or any combination thereof.

11. A method of ameliorating or delaying asthma in a subject individual in need thereof, the method comprising administering to the subject an effective amount of one or more compounds of formula (I):

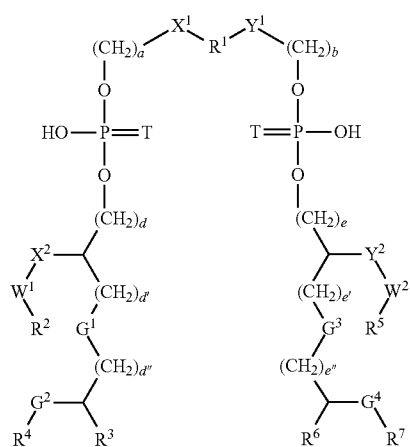

(I)

wherein:
$R^1$ is selected from the group consisting of:
(a) —C(O)—;
(b) —C(O)—$C_{1-14}$ alkyl-C(O)—, wherein said —$C_{1-14}$ alkyl- is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-5}$-alkyl-aryl is optionally substituted with $C_{1-5}$ alkoxy, $C_{1-5}$ alkylamino, $C_{1-5}$ alkoxy-amino, $C_{1-5}$ alkylamino-$C_{1-5}$ alkoxy, —O—$C_{1-5}$ alkylamino-$C_{1-5}$ alkoxy, alkylamino-C(O)—$C_{1-5}$ alkyl-C(O)OH, —O—$C_{1-5}$ alkylamino-C(O)—$C_{1-5}$ alkyl-C(O)—$C_{1-5}$ alkyl;

(c) a $C_2$ to $C_{15}$ straight or branched chain alkyl optionally substituted with hydroxy or alkoxy; and (d) —C(O)—$C_{6-12}$ arylene-C(O)— wherein said arylene is optionally substituted with hydroxy, halogen, nitro or amino;

a and b are independently 0, 1, 2, 3 or 4;
d, d', d", e, e', and e" e are independently an integer from 1 to 4;
T is oxygen;
$X^1$, $X^2$, $Y^1$, and $Y^2$ are independently selected from the group consisting of a null, oxygen, NH, N(C(O)$C_{1-4}$ alkyl), and N($C_{1-4}$ alkyl)$_2$;
$W^1$ and $W^2$ are independently selected from the group consisting of carbonyl, methylene, sulfone and sulfoxide;
$R^2$ and $R^5$ are each independently:
(a) $C_2$ to $C_{20}$ straight chain or branched chain alkyl which is optionally substituted with oxo, hydroxy or alkoxy;
(b) $C_2$ to $C_{20}$ straight chain or branched chain alkenyl or dialkenyl which is optionally substituted with oxo, hydroxy or alkoxy;
(c) $C_2$ to $C_{20}$ straight chain or branched chain alkoxy which is optionally substituted with oxo, hydroxy or alkoxy;
(d) —NH—$C_2$ to $C_{20}$ straight chain or branched chain alkyl, wherein said alkyl group is optionally substituted with oxo, hydroxy or alkoxy;

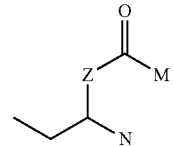

(e)

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with oxo or fluoro;

$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkoxy;

$C_2$ to $C_{20}$ straight chain or branched chain alkenyl; wherein said alkyl, alkenyl, or alkoxy groups can be independently and optionally substituted with hydroxy, fluoro or $C_1$ to $C_5$ alkoxy;

$G^1$, $G^2$, $G^3$, and $G^4$ are independently selected from the group consisting of oxygen, methylene, amino, thiol, —NHC(O)—, and —NC(O)$C_{1-4}$alkyl)-;

or $G^2R^4$ or $G^4R^7$ may together be a hydrogen atom or hydroxyl;

or a pharmaceutically acceptable salt, stereoisomer, amorphous solid thereof, or any combination thereof.

* * * * *

UNITED STATES PATENT AND TRADEMARK OFFICE
CERTIFICATE OF CORRECTION

PATENT NO. : 7,915,238 B2
APPLICATION NO. : 11/411564
DATED : March 29, 2011
INVENTOR(S) : Hawkins et al.

It is certified that error appears in the above-identified patent and that said Letters Patent is hereby corrected as shown below:

In the Patent:
Column 19, Line 30: Please correct: "–C(O) –$C_{1-14}$alkyl–C(O)"
to read -- –C(O) –$C_{1-14}$alkyl–C(O) – --

Line 35: Please correct "($C_{1-6}$alkylamino)$C_{1-4}$alkoxy,"
to read -- ($C_{1-6}$alkylamino)$C_{1-6}$alkoxy, --

Line 36: Please correct "-NH– C-alkyl"
to read -- -NH– $C_{1-6}$alkyl --

Line 37: Please correct: "alkyl-NH–C(O)$C_{1-6}$alkyl"
to read -- alkyl-NH–C(O) –$C_{1-6}$alkyl --

Line 38: Please correct "alkyl-C(O)$C_{1-6}$alkyl"
to read -- alkyl-C(O) –$C_{1-6}$alkyl --

Column 25, No. 112044, lower portion of structure: Please correct

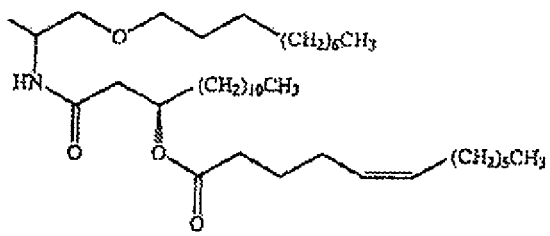

to read

Signed and Sealed this
Twentieth Day of December, 2011

David J. Kappos
*Director of the United States Patent and Trademark Office*

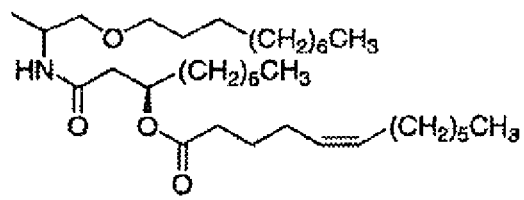
Column 29, No. 112063: Please correct
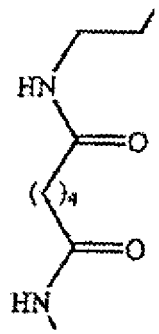
to read
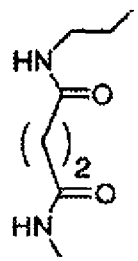
Column 33, No. 112091: Please correct
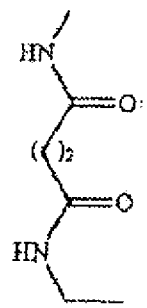
to read

Column 69, No. 804130: Please correct
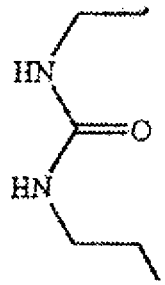
to read
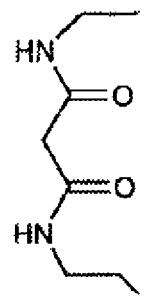
Column 73, No. 804313: Please correct
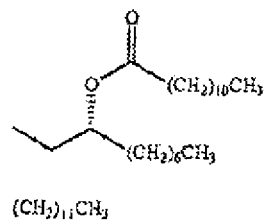
to read
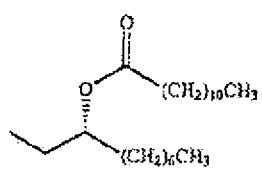

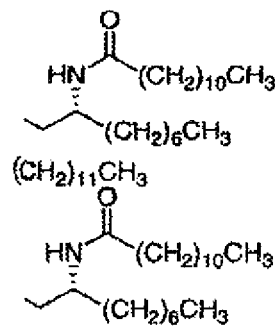
Column 76, No. 804596: Please correct
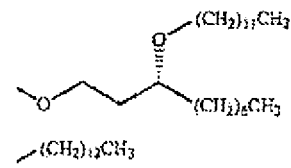
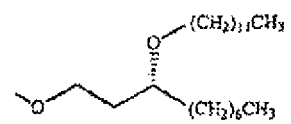
to read
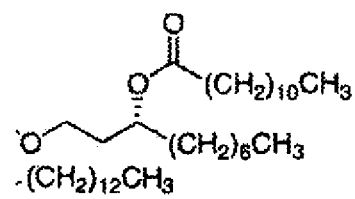
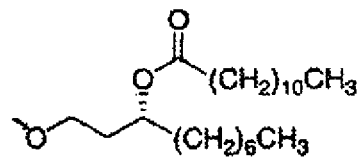

CERTIFICATE OF CORRECTION (continued)
U.S. Pat. No. 7,915,238 B2

Column 77, Item 804678: Please correct

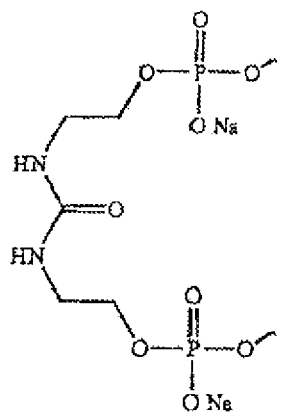

to read

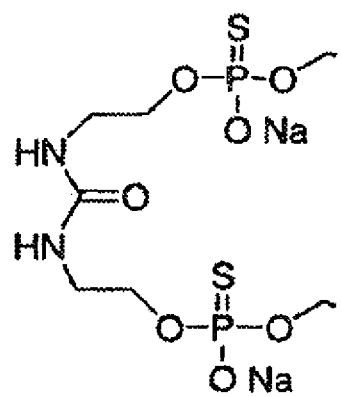

Column 77, No. 804679: Please correct

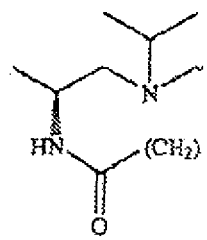

to read

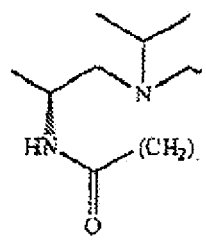

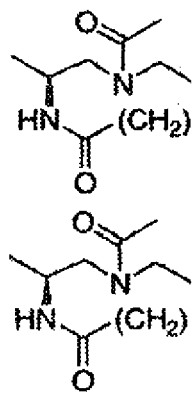

In the Claims:

Column 104, Claim 3, Line 50:
        Please correct by inserting -- –O–$C_{1-6}$alkylamino-$C_{1-6}$alkoxy, --
        immediately before "–O–$C_{1-6}$alkylamino-C(O) –$C_{1-6}$alkyl-"

Column 106, Claim 3, Line 5: Please correct "–NH–," to read -- –NH– --

Column 110, Claim 6, Line 56: Please correct "hydroxyl or alkoxy"
        to read -- hydroxyl or alkoxy; --

Column 111, Claim 6, Line 32: Please correct "$G^3$, and oxygen"
        to read -- $G^3$, and $G^4$ are oxygen --

Column 116, Claim 11, Line 3: Please correct "alkoxy, alkylamino-C(O) –$C_{1-5}$"
to read -- alkoxy, –O–$C_{1-5}$alkylamino-C(O) –$C_{1-5}$ --